United States Patent [19]

Weith et al.

[11] Patent Number: 4,946,861
[45] Date of Patent: Aug. 7, 1990

[54] 1,3-DITHIAN-2-YLIDENES, THEIR OXIDES, PHARMACEUTICAL COMPOSITIONS, AND METHODS OF USE THEREOF

[75] Inventors: André J. Weith, Signy; Philippe M. Narld, Prangins, both of Switzerland

[73] Assignee: Zyma SA, Nyon, Switzerland

[21] Appl. No.: 271,125

[22] Filed: Nov. 14, 1988

Related U.S. Application Data

[60] Division of Ser. No. 13,164, Feb. 11, 1987, Pat. No. 4,818,765, which is a continuation of Ser. No. 717,481, Mar. 28, 1985, abandoned, which is a continuation of Ser. No. 504,714, Jun. 15, 1983, abandoned.

[30] Foreign Application Priority Data

Jun. 25, 1982 [GB] United Kingdom ............. 8218472

[51] Int. Cl.$^5$ ............... C07D 339/08; A61K 31/385
[52] U.S. Cl. ............... 514/436; 549/20; 549/21; 546/284
[58] Field of Search ............. 549/20, 21; 514/436

[56] References Cited

U.S. PATENT DOCUMENTS

| | | | |
|---|---|---|---|
| 3,525,751 | 8/1970 | Fried | 549/19 |
| 3,725,394 | 4/1973 | Donche et al. | 549/32 |
| 3,781,281 | 4/1970 | Hartzler | 546/284 |

FOREIGN PATENT DOCUMENTS

| | | | |
|---|---|---|---|
| 2398745 | 2/1979 | France | 549/19 |
| 1604739 | 12/1981 | United Kingdom | 540/222 |

OTHER PUBLICATIONS

Chem. Abstr., 77:61914n (1972).
Corey et al., Tetrahedron Letters, No. 33, pp. 3201–3204 (1967).
CA 84:175153p (1976).
CA 83:10035t (1975).
Robbins et al., Pathologic Basis of Disease, 3rd Ed., pp. 892–894 (1984).
Loeb, Textbook of Medicine, 13th Ed., pp. 1390–1398 (1971).
CA 72:66955h (1970).
CA 68:73303q (1968).

*Primary Examiner*—Alan L. Rotman
*Attorney, Agent, or Firm*—JoAnn Villamizar; Irving M. Fishman

[57] ABSTRACT

The invention relates to the use of ketenethioacetals of the formula

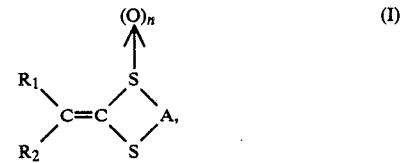

in which $R_1$ represents aryl or heteroaryl, $R_2$ represents hydrogen, an optionally substituted hydrocarbon radical, heteroaryl, an acyl radical, a group of the formula —S(O)$_m$—R$_a$, wherein m is 0, 1 or 2 and R$_a$ is an optionally substituted hydrocarbon radical; or optionally functionally modified sulpho, A represents an optionally substituted bivalent aliphatic hydrocarbon radical and n is 0 or 1, and pharmaceutically acceptable salts of such compounds that contains a salt-forming group, for the treatment of liver diseases, respiratory tract diseases and vascular diseases pharmaceutical preparations containing compounds of the formula I and novel compounds of the formula I. The compounds have liver-protecting and immunomodulating properties.

28 Claims, No Drawings

1,3-DITHIAN-2-YLIDENES, THEIR OXIDES, PHARMACEUTICAL COMPOSITIONS, AND METHODS OF USE THEREOF

This is a divisional of application Ser. No. 013,164, filed Feb. 11, 1988 now U.S. Pat. No. 4,818,765 which is a continuation of Ser. No. 771,481 filed on Mar. 28, 1985 abandoned, which is a continuation of Ser. No. 504,714, filed June 15, 1983, abandoned.

The invention relates to the use of dithio compounds for the treatment of liver diseases, pharmaceutical preparations containing such compounds, novel dithio compounds and processes for their manufacture. These compounds have valuable pharmaceutical properties.

The invention relates to the use of ketenethioacetals of the formula

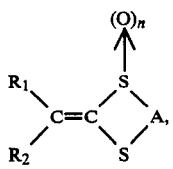

in which $R_1$ represents aryl or heteroaryl, $R_2$ represents hydrogen, an optionally substituted hydrocarbon radical, heteroaryl, an acyl radical, a group of the formula —$S(O)_m$—$R_a$, wherein m is 0, 1 or 2 and $R_a$ is an optionally substituted hydrocarbon radical; or optionally functionally modified sulpho, A represents an optionally substituted bivalent aliphatic hydrocarbon radical and n is 0 or 1, and pharmaceutically acceptable salts of such compounds that contain a salt-forming group, for the treatment of liver diseases, respiratory tract diseases and vascular diseases.

The definitions used hereinbefore and hereinafter have, within the scope of the present description, preferably the following meanings: An aryl radical $R_1$ is, for example, a monocyclic or polycyclic, such as bicyclic, aryl radical, especially having up to 20 carbon atoms, such as the phenyl or the naphthyl radical. These radicals may be, for example, mono- or poly-substituted, for example di- or tri-substituted, by hydroxy, etherified hydroxy, such as lower alkoxy which is optionally substituted by carboxy, esterified carboxy, disubstituted amino, halogen, sulpho or hydroxy, for example lower alkoxy, carboxy-lower alkoxy, lower alkoxycarbonyl-lower alkoxy, di-lower alkylamino-lower alkoxy, halo-lower alkoxy, sulpho-lower alkoxy or hydroxy-lower alkoxy; esterified hydroxy, for example halogen, lower alkanoyloxy or di-lower alkylamino-lower alkanoyloxy; alkyl having up to 20 carbon atoms, especially up to 14 carbon atoms; lower alkyl which is substituted by hydroxy, esterified hydroxy, etherified hydroxy or disubstituted amino, such as halo-lower alkyl, lower alkoxy-lower alkyl or di-lower alkylamino-lower alkyl; loweralkanoyl; carboxy; lower alkoxycarbonyl optionally substituted by disubstituted amino, such as lower alkoxycarbonyl or di-lower alkylamino-lower alkoxycarbonyl; phenyl optionally substituted by lower alkyl, lower alkoxy, halogen and/or nitro; nitro and/or by optionally substituted amino, such as amino, lower alkylamino, di-lower alkylamino, lower alkyleneamino, lower alkyleneamino that is interrupted by an optionally lower alkylated nitrogen atom or an oxygen or sulphur atom, and/or acylamino, such as lower alkanoylamino or carboxy-lower alkanoylamino.

Heteroaryl $R_1$ is, for example, a bicyclic or, especially, a monocyclic radical, which is preferably bonded by a ring carbon atom to the carbon atom of the double bond. As a corresponding monocyclic radical, $R_1$ contains especially one, two or three nitrogen atoms and/or an oxygen or sulphur atom and is, for example, an aza, oxa-, thia-, diaza-, oxaza- or thiaza-cyclic radical having 5 ring members, or a monoaza- or diaza-cyclic radical having 6 ring members. Corresponding bicyclic radicals $R_1$ consist, for example, of a 5-membered hetero ring of aromatic character having two nitrogen atoms or having one nitrogen atom and/or an oxygen or sulphur atom as ring members and a fused benzene ring, or of a 6-membered hetero ring of aromatic character having 2 or, especially, 1 nitrogen atom as ring members and a fused benzene ring. These radicals may be, for example, mono- or polysubstituted, for example di- or trisubstituted, by hydroxy, etherified hydroxy, such as lower alkoxy, esterified hydroxy, such as halogen, lower alkyl, halo-lower alkyl and/or nitro.

An optionally substituted hydrocarbon radical $R_2$ is, for example, a corresponding aliphatic, cycloaliphatic, cycloaliphatic-lower aliphatic, aromatic, aromatic-lower aliphatic or heteroaromatic-lower aliphatic radical having up to 20 carbon atoms, especially up to 12 carbon atoms.

An aliphatic radical $R_2$, which may optionally be substituted, is lower alkenyl, lower alkynyl or, especially, lower alkyl. Substituents of lower alkenyl, lower alkynyl and, especially, lower alkyl radicals $R_2$ are, for example, hydroxy, esterified hydroxy, such as hydroxy esterified by a lower alkanecarboxylic acid, by benzoic acid optionally substituted by nitro, halogen, lower alkyl and/or lower alkoxy, or by hydrohalic acid, for example lower alkanoyloxy, correspondingly substituted benzoyloxy or halogen, etherified hydroxy, such as lower alkoxy or lower alkenyloxy, etherified mercapto, such as lower alkylthio or phenylthio, lower alkylsulphinyl, phenylsulphinyl, lower alkylsulphonyl, nitro, carboxy, functionally modified carboxy, such as lower alkoxycarbonyl, cyano or optionally N-mono-or N,N-di-lower alkylated carbamoyl, or optionally substituted amino, such as amino, lower alkyl- or di-lower alkylamino, amino-lower alkylamino, wherein the terminal amino group is optionally substituted by lower alkyl, lower alkylene or lower alkylene that is interrupted by an optionally lower alkylated nitrogen atom or an oxygen or sulphur atom, lower alkyleneamino, or lower alkyleneamino that is interrupted by an optionally lower alkylated nitrogen atom or an oxygen or sulphur atom.

A cycloaliphatic radical $R_2$ is, for example, cycloalkyl.

A cycloaliphatic-lower aliphatic radical $R_2$ is especially cycloalkyl-lower alkyl.

Cycloaliphatic and cycloaliphatic-lower aliphatic radicals $R_2$ may be substituted one or more times in the cycloaliphatic or lower aliphatic moiety by, for example, lower alkyl, hydroxy, etherified hydroxy, for example lower alkoxy, esterified hydroxy, for example halogen, carboxy, or esterified carboxy, such as lower alkoxycarbonyl.

An optionally substituted aromatic radical R is, for example, one of the aryl radicals mentioned in the definition of $R_1$.

An aromatic-lower aliphatic radical $R_2$ is one of the mentioned lower aliphatic radicals, especially lower alkyl, which may be substituted by from 1 to 3 aromatic radicals, especially by one of the aryl radicals mentioned in the definition of $R_1$. These radicals may be mono- or polysubstituted in the aromatic moiety in the manner indicated above. Such a radical is, for example, phenyl-lower alkyl optionally substituted by lower alkyl, etherified hydroxy, such as lower alkoxy, esterified hydroxy, such as halogen, or nitro.

A heteroaromatic-lower aliphatic radical R is a lower aliphatic radical, especially lower alkyl, which is substituted, preferably mono-substituted, by one of the optionally substituted monocyclic heteroaryl radicals mentioned in the definition of $R_1$ which contain one, two or three nitrogen atoms and/or an oxygen or sulphur atom, for example by furyl, such as 2- or 3-furyl, thienyl, such as 2- or 3-thienyl, or pyridyl, such as 2-, 3- or 4-pyridyl and is, for example, corresponding furyl-, thienyl- or pyridyl-lower alkyl, especially methyl. The heteroaryl radicals are optionally substituted, for example, by lower alkyl, lower alkoxy, halogen or halo-lower alkyl.

A heteroaryl radical R is a monocyclic heteroaryl radical containing one, two or three nitrogen atoms and/or an oxygen or a bicyclic heteroaryl radical consisting of a 5-membered hetero ring of aromatic character having 2 nitrogen atoms or having one nitrogen atom and/or an oxygen or sulphur atom as ring members and a fused benzene ring, or consisting of a 6-membered hetero ring of aromatic character having one or two nitrogen atoms as ring members and a fused benzene ring. Such heteroaryl radicals are, for example, the heteroaryl radicals listed in the definition of the radical $R_1$.

An acyl radical $R_2$ is, for example, the acyl radical of an optionally substituted lower aliphatic, cycloaliphatic, aromatic, aromatic-lower aliphatic or heteroaromatic carboxylic acid, especially having up to 20 carbon atoms, and represents, for example, optionally substituted lower alkanoyl, cycloalkanoyl, aroyl, aryl -lower alkanoyl or heteroaroyl, or heteroanalogous derivatives thereof, such as the corresponding thio- or imino-acyl radicals. Suitable substituents of these radicals are, for example, hydroxy, esterified hydroxy, such as halogen, etherified hydroxy, such as lower alkoxy, lower alkyl, halo-lower alkyl, lower alkenyl, carboxy, esterified carboxy, such as lower alkoxycarbonyl, cyano, nitro and/or phenyl optionally substituted, for example, by lower alkyl. Further acyl radicals $R_2$ are, for example, the acyl radicals of optionally functionally modified carbonic acid, for example carboxy, functionally modified carboxy, such as esterified carboxy, especially alkoxycarbonyl, for example having up to 20 carbon atoms, preferably up to 9 carbon atoms, cyano or amidated carboxy, especially carbamoyl, mono- or di-lower alkylated carbamoyl, or carbamoyl substituted by lower alkylene, lower alkenyl, lower alkanoyl or benzoyl; or the acyl radical of functionally modified thiocarbonic acid, for example amidated thiocarboxy, such as thiocarbamoyl optionally mono- or disubstituted by, for example, lower alkyl, or substituted by lower alkylene.

In a group of the formula $-S(O)_m-R_a$, the optionally substituted hydrocarbon radical $R_a$ is, for example, one of those mentioned above in the definition of an optionally substituted hydrocarbon radical $R_2$, for example lower alkyl, or aryl or aryl-lower alkyl, such as phenyl- or phenyl-lower alkyl each optionally substituted by lower alkyl, etherified hydroxy, such as lower alkoxy, esterified hydroxy, for example halogen, and/or nitro. Groups of the formula $-S(O)_m-R_a$ are, for example, lower alkylthio, phenylthio, phenyl-lower alkylthio, phenylsulphinyl, phenyl-lower alkylsulphinyl, lower alkylsulphonyl, phenylsulphonyl or phenyl-lower alkylsulphonyl wherein the phenyl radicals are optionally substituted as described above.

Optionally functionally modified sulpho $R_2$ is, for example, sulpho, esterified sulpho, especially lower alkoxysulphonyl or phenyl-lower alkoxysulphonyl, or especially amidated sulpho, such as optionally lower alkylated or phenylated aminosulphonyl.

An optionally substituted bivalent aliphatic hydrocarbon radical A is, for example, a corresponding lower alkylene, lower alkylidene or lower alkenylene radical, which separates the sulphur atoms by from 1 to 5, especially from 2 to 4 carbon atoms, and which may optionally be substituted one or more times. Substituents of such radicals are, for example, oxo, hydroxy, esterified hydroxy, such as halogen, lower alkanoyloxy, halo-lower alkanoyloxy, or benzoyloxy optionally substituted by, for example, nitro, lower alkyl and/or lower alkoxy, or etherified hydroxy, such as lower alkoxy, phenyl-lower alkoxy optionally substituted in the phenyl moiety by, for example, nitro, halogen, lower alkyl and/or lower alkoxy, or phenoxy optionally substituted, for example, by nitro, lower alkyl, lower alkoxy and/or halogen. Other substituents are, for example, etherified mercapto, such as lower alkylthio, phenylthio or phenyl-lower alkylthio, optionally functionally modified carboxy, such as carboxy, lower alkoxycarbonyl, cyano, carbamoyl or mono- or di-lower alkylated carbamoyl, amino or substituted amino, such as lower alkylamino, di-lower alkylamino, lower alkyleneamino, lower alkenylamino, anilino, phenyl-lower alkylamino, lower alkanoylamino or organic sulphonylamino, such as lower alkanesulphonylamino, or benzenesulphonylamino optionally substituted by, for example, lower alkyl or halogen. Further, these radicals A may be substituted, for example, by nitro, cycloalkyl, aryl, such as one of the optionally substituted aryl radicals described in the definition of aryl $R_1$, or by heteroaryl, such as one of the optionally substituted heteroaryl radicals described in the definition of heteroaryl $R_1$.

In the present description, the term "lower" used in connection with the definitions of substituents or compounds means that, unless expressly defined to the contrary, the corresponding substituents or compounds contain up to 7, preferably up to 4, carbon atoms.

Lower alkoxy is, for example, methoxy, ethoxy, n-propoxy, isopropoxy, n-butoxy or tert-butoxy.

Carboxy-lower alkoxy is, for example, carboxmethoxy or 2-carboxyethoxy.

Lower alkoxycarbonyl-lower alkoxy is, for example, methoxycarbonylmethoxy or ethoxycarbonylmethoxy.

Di-lower alkylamino-lower alkoxy is, for example, 2-(N,N-dimethylamino)-ethoxy or 2-(N,N-diethylamino)-ethoxy.

Halo-lower alkoxy is, for example, trifluoromethoxy.
Sulpho-lower alkoxy is, for example, sulphomethoxy or 2-sulphoethoxy.

Hydroxy-lower alkoxy is, for example, 2-hydroxyethoxy, 2-hydroxypropoxy or 2,3-dihydroxypropoxy.

Halogen is, for example, fluorine, chlorine, bromine or iodine.

Lower alkanoyloxy is, for example, formyloxy, acetoxy, propionyloxy, butyryloxy, isobutyryloxy, pivaloyloxy or valeroyloxy.

Di-lower alkylamino-lower alkanoyloxy is, for example, N,N-dimethylglycyloxy, N,N-diethylglycyloxy, N,N-dimethylalanyloxy or N,N-dimethy-$\beta$-alanyloxy.

Alkyl is, for example, lower alkyl, such as methyl, ethyl, n-propyl, isopropyl, n-butyl, isobutyl, sec-butyl, tert-butyl, n-pentyl, n-hexyl or n-heptyl, or alkyl having from 8 to 20 carbon atoms, such as n-octyl, n-nonyl, n-decyl, n-dodecyl or n-tetradecyl, furthermore n-hexadecyl or n-octadecyl.

Halo-lower alkyl is, for example, trifluoromethyl.

Lower alkoxy-lower alkyl is, for example, methoxymethyl, methoxyethyl, ethoxymethyl or ethoxyethyl.

Di-lower alkylamino-lower alkyl is, for example, dimethylaminomethyl, 2-dimethylaminoethyl or 2-diethylaminoethyl.

Lower alkanoyl is, for example, formyl acetyl, propionyl, n-butyryl, pivaloyl or valeroyl.

Lower alkoxycarbonyl is, for example, methoxycarbonyl, ethoxycarbonyl, n-propoxycarbonyl, isopropoxycarbonyl, n-butoxycarbonyl, sec-butoxycarbonyl, tert-butoxycarbonyl, n-pentoxycarbonyl, n-hexyloxycarbonyl or n-heptyloxycarbonyl.

Di-lower alkylamino-lower alkoxycarbonyl is, for example, 2-(N,N-dimethylamino)- or 2-(N,N-diethylamino)-ethoxycarbonyl.

Lower alkylamino is, for example, methylamino, ethylamino, n-propylamino, isopropylamino or n-butylamino, whilst di-lower alkylamino is, for example, dimethylamino, diethylamino, di-n-propylamino, diisopropylamino, or methyl-diisopropylamino.

Lower alkyleneamino has especially from 4 to 6 carbon chain members and is, for example, pyrrolidin-1-yl or piperidino.

Lower alkyleneamino that is interrupted by an optionally lower alkylated nitrogen atom or an oxygen or sulphur atom has, for example, from 4 to 6 chain members and is, for example piperazino, 4-lower alkyl-piperazino, such as 4-methyl- or 4-ethyl-piperazino, morpholino or thiomorpholino.

Lower alkanoylamino is, for example, formylamino, acetylamino, propionylamino or butyrylamino.

Carboxy-lower alkanoylamino is, for example, malonyl- or succinylamino.

Monocyclic 5-membered heteroaryl $R_1$ is, for example, 1H-pyrrolyl, such as 1H-pyrrol-2-yl or -3-yl, furyl, such as 2- or 3-furyl, thienyl, such as 2- or 3-thienyl, 1H-pyrazolyl, such as 1H-pyrazol-3-yl or -4-yl, 1H-imidazolyl, such as 1H-imidazol-2-yl, oxazolyl, such as 2-oxazolyl, isoxazolyl, such as 3- or 5-isoxazolyl, or thiazolyl, such as 2- or 4-thiazolyl. Monocyclic 6-membered heteroaryl $R_1$ is, for example, pyridyl, such as 2-, 3- or 4-pyridyl, pyridazinyl, such as 3-pyridazinyl, pyrazinyl, such as 2-pyrazinyl, or pyrimidinyl, such as 2-, 4- or 5-pyrimidinyl. Bicyclic heteroaryl $R_1$ is, for example, 1H-indolyl, such as 1H-indol-2-yl, -3-yl or -4-yl, 1H-indazolyl, such as 1H-indazol-3-yl, 1H-benzimidazolyl, such as 1H-benzimidazol-2-yl, benzofuranyl, such as 2-, 3- or 5-benzofuranyl, benzothienyl, such as 2-, 3- or 4-benzothienyl, benzoxazolyl, such as 2-benzoxazolyl, benzothiazolyl, such as 2-benzothiazolyl, or corresponding quinolinyl, such as 2-, 4-, 5- or 6-quinolinyl, isoquinolinyl, such as 1- or 4-isoquinolinyl, quinazolinyl, such as 2-, 4or 6-quinazolinyl, or quinoxalinyl, such as 2- or 6-quinoxalinyl. These radicals may be unsubstituted or substituted as defined above.

Lower alkenyl is, for example, vinyl, allyl, 1-propenyl, isopropenyl, 2- or 3-methylallyl or 3-butenyl.

Lower alkynyl is, for example, propargyl or 2-butynyl.

Lower alkenyloxy is, for example, vinyloxy or allyloxy.

Lower alkylthio is, for example, methylthio, ethylthio, n-propylthio, isopropylthio, n-butylthio or tert-butylthio.

Lower alkylsulphinyl is, for example, methylsulphinyl, ethylsulphinyl, n-propylsulphinyl, n-butylsulphinyl or tert-butylsulphinyl.

Lower alkylsulphonyl is, for example, methylsulphonyl, ethylsulphonyl, n-propylsulphonyl, isopropylsulphonyl, n-butylsulphonyl, isobutylsulphonyl or tert-butylsulphonyl.

N-Mono-lower alkylated carbamoyl is, for example, N-methyl-, N-ethyl-or N-propyl-carbamoyl, whilst N,N-di-lower alkylated carbamoyl is, for example, N,N-dimethyl- or N,N-diethyl-carbamoyl.

Amino-lower alkylamino wherein the terminal amino group is optionally substituted by lower alkyl, lower alkylene or lower alkylene that is interrupted by an optionally lower alkylated nitrogen atom or an oxygen or sulphur atom, is, for example, di-lower alkylamino-lower alkylamino, such as 2-(N,N-dimethylamino)- or 2-(N,N-diethylamino)ethylamino, lower alkyleneamino, such as 2-(pyrrolidin-1-yl)- or 2-piperidino-ethylamino, 2-morpholino-ethylamino or 2-(4-lower alkylpiperazino)-lower alkylamino, such as 2-(4-methylpiperazino)-ethylamino.

Substituted lower alkyl groups $R_2$ are, for example, hydroxy-lower alkyl, for example hydroxymethyl, 2-hydroxyethyl or 2,3-dihydroxypropyl, halo-lower alkyl, for example trifluoromethyl, lower alkanoyloxy-lower alkyl, for example 2-acetoxymethyl, optionally substituted benzoyloxy-lower alkyl, for example benzoyloxymethyl or 4-methoxybenzoyloxymethyl, lower alkoxy-lower alkyl, for example ethoxymethyl, lower alkenyloxy-lower alkyl, for example 2-allyloxyethyl, lower alkylthio-lower alkyl, for example n-butylthiomethyl, phenylthio-lower alkyl, for example phenylthiomethyl or 1-phenylthioethyl, phenylsulphinyl-lower alkyl, for example phenylsulphinylmethyl or 2-phenylsulphinylethyl, lower alkylsulphonyl-lower alkyl, for example methylsulphonylmethyl or 2-methylsulphonylethyl, cyano-lower alkyl, for example cyanomethyl or cyanoethyl, carboxy-lower alkyl, for example carboxymethyl, 2-carboxy- or 1,2-dicarboxyethyl, lower alkoxycarbonyl-lower alkyl, for example ethoxycarbonylmethyl or 2-isopropoxycarbonylethyl, optionally mono- or di-lower alkylated carbamoyl-lower alkyl, for example carbamoylmethyl or N,N-diethylcarbamoylmethyl, lower alkylamino- or di-lower alkylamino-lower alkyl, for example ethylaminoethyl, dimethylaminomethyl, 2-dimethylaminoethyl or methyl-isopropylaminomethyl, lower alkyleneamine-lower alkyl, for example pyrrolidinomethyl or 2-piperidinoethyl, morpholino-lower alkyl, for example morpholinomethyl, or morpholino-lower alkylamino-lower alkyl, for example 2-morpholinoethylaminomethyl.

Substituted lower alkenyl groups $R_2$ are, for example, lower alkoxycarbonyl-lower alkenyl, for example 2-ethoxycarbonyl vinyl, or lower alkylsulphinyl-lower alkenyl, for example 2-ethylsulphinylvinyl.

Cycloalkyl contains, for example, from 3 to 8, but especially 5 or 6, ring members and is especially cyclopentyl or cyclohexyl, or also cyclopropyl or cycloheptyl.

Cycloalkyl-lower alkyl is, for example, cyclopropylmethyl, cyclopentylmethyl, cyclohexylmethyl or 2-cyclohexylethyl.

Phenyl-lower alkyl is, for example, benzyl, diphenylmethyl, triphenylmethyl or 2-phenylethyl.

Cycloalkanoyl is, for example, cyclopentanoyl, cyclohexanoyl or cycloheptanoyl.

Aroyl is, for example, benzoyl or naphthoyl each optionally mono-, di- or trisubstituted by lower alkyl, hydroxy, esterified hydroxy, such as halogen, etherified hydroxy, such as lower alkoxy, optionally mono- or disubstituted amino, such as amino, lower alkylamino, di-lower alkylamino or lower alkanoylamino, carboxy, functionally modified carboxy, such as lower alkoxycarbonyl or optionally mono- or di-lower alkylated carbamoyl, and/or nitro.

Aryl-lower alkanoyl is, for example, phenyl-lower alkanoyl, for example phenylacetyl or phenylpropionyl.

Heteroaroyl is, for example, the acyl radical of a monocyclic 5-membered heteroarenecarboxylic acid that contains a nitrogen, sulphur and/or oxygen atom and is optionally substituted, for example, by lower alkyl or esterified hydroxy, for example halogen, such as furoyl, for example 2- or 3-furoyl, or thenoyl, for example 2- or 3-thenoyl, or the acyl radical of a monocyclic 6-membered heteroarenecarboxylic acid containing 1 or 2 nitrogen atoms, especially pyridoyl, such as 2-, 3- or 4-pyridoyl, or corresponding pyridoyl substituted, for example, by hydroxy, etherified hydroxy, such as lower alkoxy, halo-lower alkyl and/or cyano.

A thioacyl radical $R_2$ is a radical of the formula $R_3-C(=S)-$ in which $R_3$ represents for example, hydrogen, lower alkyl, phenyl or phenyl-lower alkyl.

An iminoacyl radical $R_2$ is, for example, a group of the formula $R_3-C(=NR_4)-$ in which $R_3$ has the meaning given above and $R_4$ represents, for example, lower alkyl, phenyl or phenyl-lower alkyl.

Alkoxycarbonyl having up to 20 carbon atoms as the radical $R_2$ is, for example, lower alkoxycarbonyl as defined above, n-octyloxycarbonyl, n-nonyloxycarbonyl or n-decyloxycarbonyl, furthermore n-dodecyloxycarbonyl or cetyloxycarbonyl.

Lower alkylene in amidated carboxy or thiocarbamoyl radicals has, for example, from 4 to 6 chain members, and is, for example, 1,4-butylene, 1,5-pentylene or 1,6-hexylene.

Lower alkylene in radicals A is, for example, ethylene, 1,2- and 1,3-propylene, 1,2-, 1,3,1,4- and 2,3-butylene, 1,4- 2,3- or 2,4-pentylene and the like.

Lower alkylthio is, for example, methylthio, ethylthio, n-propylthio, isopropylthio, n-butylthio, isobutylthio or tert-butylthio.

Phenyl-lower alkylthio is, for example, benzylthio or 2-phenylethylthio.

Phenyl-lower alkylsulphinyl is, for example, benzylsulphinyl or 2-phenylethylsulphinyl.

Lower alkylsulphonyl is, for example, methylsulphonyl, ethylsulphonyl, n-propylsulphonyl, isopropylsulphonyl or n-butylsulphonyl.

Phenyl-lower alkylsulphonyl is, for example, benzylsulphonyl or 2-phenylethylsulphonyl.

Lower alkoxysulphonyl is, for example, methoxysulphonyl or ethoxysulphonyl, whilst phenyl-lower alkoxysulphonyl is, for example, benzyloxysulphonyl.

Lower alkylated aminosulphonyl is, for example, N-lower alkyl-, such as N-methyl- or N-ethyl-aminosulphonyl, or N,N-di-lower alkyl-, for example, N,N-dimethyl- or N,N-diethyl-aminosulphonyl, whilst phenylated aminosulphonyl is, for example, N-phenylaminosulphonyl.

Lower alkylidene radicals A, which can also be unsaturated, are, for example, methylene, ethylidene, 1- or 2-propylidene, 2-butylidene, vinylidene or 1-propen-1-ylidene.

Lower alkenylene radicals A in which the double bond can be located either inside the dithiaheterocycle or exocyclically are, for example, vinylene, 1,2- and 1,3-propenylene, 1,2-, 1,3- and 1,4-but-1-enylene, 1,3- and 2,3-but-2-enylene or 2-methylene-1,3-propylene.

Halo-lower alkanoyloxy is, for example, chloroacetoxy or trifluoroacetoxy.

Phenyl-lower alkoxy is, for example, benzyloxy, 2-phenylethoxy or diphenylmethoxy.

Lower alkenylamino is, for example, allylamino or 2-methylallylamino.

Phenyl-lower alkylamino is, for example, benzylamino or 2-phenylethylamino.

Lower alkanesulphonylamino is, for example, methanesulphonylamino or ethanesulphonylamino.

Salts of compounds of the formula (I) are especially pharmaceutically acceptable non-toxic salts, such as those of compounds of the formula I with acidic groups, for example with a free carboxyl or sulpho group. Such salts are especially metal or ammonium salts, such as alkali metal or alkaline earth metal salts, for example sodium, potassium, magnesium or calcium salts, as well as ammonium salts, which are formed with ammonia or suitable organic amines. There come into consideration for the salt formation especially aliphatic, cycloaliphatic, cycloaliphatic-aliphatic or araliphatic primary, secondary or tertiary mono-, di or poly-amines, as well as heterocyclic bases, such as lower alkylamines, for example di- or tri-ethylamine, hydroxy-lower alkylamines, for example 2-hydroxyethylamine, bis-(2-hydroxyethyl)-amine or tris-(2-hydroxyethyl)-amine, basic aliphatic esters or carboxylic acids, for example 4-aminobenzoic acid, 2-diethylaminoethyl ester, lower alkyleneamines, for example 1-ethylpiperidine, cycloalkylamines, for example dicyclohexylamine, or benzylamines, for example N,N'-dibenzylethylenediamine.

Compounds of the formula I having a basic group may form acid addition salts, for example with inorganic acids, such as hydrochloric acid, sulphuric acid or phosphoric acid, or with suitable organic carboxylic or sulphonic acids, for example acetic acid, succinic acid, fumaric acid, tartaric acid, methanesulphoric acid and p-toluenesulphonic acid. In the presence of several acidic or basic groups, mono- or poly-salts may be formed. Compounds of the formula I having an acidic group, for example a free carboxy group, and a basic group, for example an amino group, may also be present in the form of inner salts, i.e. in zwitterionic form, or a part of the molecule may be present in the form of an inner salt and another part in the form of a normal salt.

For isolation or purification it is also possible to use other salts than the pharmaceutically acceptable salts. Compounds of the formula (I) in which the radicals $R_1$ and $R_2$ are different and A represents an asymmetric or asymmetrically substituted bivalent aliphatic hydrocarbon radical may be in the form of cis-trans isomers. Furthermore, compounds of the formula (I) having one or more asymmetric carbon atoms may be in the form of an individual stereoisomer, for example enantiomer, or a mixture of at least two stereoisomers, for example in the form of a diastereoisomeric mixture or enantiomeric mixture, such as a racemate.

The compounds of the formula I possess various valuable pharmacological properties which are quite surprisingly associated in the same molecules.

In particular these compounds show an interesting activity in the prevention of hepatic necrosis and hepatic fibrosis. They also possess immunomodulating properties. These compounds modify the viscoelasticity of mucus secretion, stimulate the mucociliary transport and relax the smooth muscles in bronchi. These compounds possess also anti-inflammatory and vasculotropic protective effects.

The hepatic antinecrotic properties of these compounds are demonstrated by the galactosamine hepatitis test in the rat, which is a well-known model for faithful reproduction of the morphological and biochemical changes of human viral hepatitis. Rats treated intraperitoneally or orally with these substances in doses varying from 10 to 200 mg/kg are protected from hepatic necrosis induced with galactosamine. The hepatic effect is assessed by measuring the plasma level of transaminases and by histological examination of the liver.

The antifibrotic hepatic properties of these substances are demonstrated in the model of chronic intoxication of the rat with carbon tetrachloride. The administration of carbon tetrachloride to the rat in a dose of 0.5 ml/kg (twice a week for 9 weeks) causes toxic hepatitis linked with intense hepatic fibrosis. The preventive treatment (during the 9 weeks of intoxication) or the curative treatment (from the 6th to the 9th week of intoxication) with these compounds in doses varying from 50 to 200 mg/kg decreases the alterations of the hepatic functions as well as the hepatic fibrosis associated with that chronic intoxication. The hepatic functions are assessed at the end of the experiment by the following tests: BSP (bronchosulphophthalein) test, plasma level of bilirubin and plasma level of transaminases. The severity of the hepatic fibrosis is assessed by measuring the hepatic hydroxyproline content, which reflects the amount of collagen, and by the histological examination of the liver. All of these parameters are favourably influenced by the treatment with these substances.

The decrease of hepatic fibrosis during curative treatment with these substances suggests that they are able to modify the collagen metabolism. The direct action on the collagen metabolism can be demonstrated by studying the effect of these substances on in vivo cultures of fibroblasts of animal or human origin. The addition of these substances, in concentrations varying from 1 to 10 μg/ml of culture medium, results in a decrease of the incorporation of $^{14}$C-proline in the collagen synthesized by the fibroblasts. This activity occurs without the biosynthesis of non-collagenous proteins being modified, which corresponds to a specific inhibition of the collagen biosynthesis influenced by the compounds.

The immunomodulating properties of these compounds are demonstrated by a test battery normally used in immunology:

(a) Humoral immunity test: production of antibodies against bovine albumin in the mouse. The compounds of the present invention administered in a dose of 10 to 100 mg/kg, 15 minutes after the antigen (bovine albumin), stimulate antibody production against this antigen, as measured 15 to 28 days later by the passive haemagglutination technique.

(b) Cellular immunity test: delayed hypersensitivity reaction to the bovine albumin in the guinea-pig. The compounds of the present invention administered subcutaneously in a dose of 10 to 100 mg/kg at the delayed hypersensitivity reaction triggered off by subcutaneous injection of the antigen 21 days later.

(c) Cytotoxicity test of mice macrophages against tumoral cells: the macrophages, collected from mice treated by doses of 10 to 100 mg/kg of the compounds of the present invention, have a stimulated cytotoxicity against tumoral target cells.

These tests establish that the three main processes involved in the immunological defense (humoral immunity, cellular immunity and macrophages) are modified by the action of these substances, and demonstrate their immunomodulating properties.

The compounds of the formula I can accordingly be used for the treatment of acute and chronic diseases induced by viruses, toxics or alcohol. The impairment of hepatic functions which results essentially from hepatic necrosis and fibrosis is diminished by these compounds.

Owing to their inhibition of collagen biosynthesis, these compounds are of particular interest in the treatment of chronic liver diseases and, above all, of hepatic cirrhosis.

The stimulation of the immunological defenses induced by these compounds is useful in the treatment of acute and chronic viral hepatitis but also in the treatment of all cases where there is an alteration of immunological defense reactions, such as in the case of repeated bacterial or viral infections or carcinogenous diseases. In the latter case, the importance of the substances is specifically demonstrated by the activation of the cytotoxic effect of macrophages for tumoral cells.

These compounds modify the viscoelasticity of mucus secretion, they stimulate the mucociliary transport in bronchi and they relax smooth muscles of bronchi. These properties make the compounds useful for the treatment of diseases of the respiratory tract, as for example chronic bronchitis.

The modification of viscoelasticity of mucus samples by these compounds is measured with a microrheometer.

The mucus is obtained from fresh pig's stomach scrapings and is purified biochemically before use. The test compounds are dissolved in specific solvents, distilled water, phosphate butter, methanol aqueous mixture, or in DMSO (dimethylsulphoxide). 50 mg aliquotes of mucus with 5–10 μl of the test solution are added. The samples are mixed, centrifuged and incubated for 30 min. for interaction to take place. The samples are then loaded into the cell of an oscillating sphere magnetic microrheometer and a 200 μm iron sphere is placed centrally in the sample which is allowed 5 minutes for relaxation to take place. The rheological behaviour is evaluated at 25° C. over the frequency range of 0.1 to 20 Hz.

The stimulation of mucociliary transport is demonstrated with pharmacological model of frog palate. In this system, the speed of transport of particles by the ciliated epithelium of frog palate is measured. By adding solutions of compounds to be tested (0.1–1 mg/ml) on the frog palate an increase in the speed of transport is measured.

The relaxing effect of these compounds on the smooth muscles of bronchi is demonstrated by the protection afforded by these compounds against the bronchospasm induced by histamine aerosol in Guinea-pigs. Pretreatment of Guinea-pigs by i.p. route with the new compounds (10–100 mg/kg) allows the animals to resist more than 5 minutes to the histamine aerosol; control animals do not resist more than 1 min. and 30 sec.

These compounds are also useful for the treatment of venous or arterial circulatory diseases.

The antiinflammatory, vasculotropic and protective properties of the compounds may be demonstrated in the following studies:

(1) At doses varying between 100 and 500 mg/kg. by parenteral or oral administration, they are able to reduce edema caused by galactosamine, by heat and by stasis. Even more important, these beneficial effects are seen in the absence of any central haemodynamic activity. The compounds favourably modify vascular reactivity in terms of both micro- and macro-circulation. They are also capable of improving peripheral blood circulation (legs). Finally, these substances counteract the toxic effects of histamine in cultures of endothelial cells.

(2) Hypercholesterolemia is an aggravating factor of vascular diseases. Therefore the effect of the new compounds on the serum cholesterol level of mice fed a high cholesterol-cholic acid diet for 7 days was investigated. It was found that the new compounds at doses varying between 100 and ~500 mg/kg orally reduced significantly the serum cholesterol level. Moreover it could be demonstrated that this reduction resulted from a decrease cf cholesterol linked to low and very low density lipoproteins.

The invention relates especially to the use of compounds of the formula I in which $R_1$ represents a monocyclic or polycyclic aryl radical having up to 20 carbon atoms which is optionally substituted by hydroxy, lower alkoxy, carboxy-lower alkoxy, lower alkoxycarbonyl-lower alkoxy, di-lower alkylamino-lower alkoxy, halo-lower alkoxy, sulpho-lower alkoxy, hydroxy-lower alkoxy, halogen, lower alkanoyloxy, di-lower alkylamino-lower alkanoyloxy, alkyl having up to 20 carbon atoms, lower alkyl substituted by hydroxy, halogen lower alkoxy or di-lower alkylamino, lower alkanoyl, carboxy, lower alkoxycarbonyl optionally substituted by di-lower alkylamino, phenyl optionally substituted by lower alkyl, lower alkoxy, halogen and/or nitro, nitro, amino, lower alkylamino, di-lower alkylamino, lower alkyleneamino, lower alkyleneamino that is interrupted by an optionally lower alkylated nitrogen atom or an oxygen or sulphur atom, lower alkanoylamino and/or carboxy-lower alkanoylamino; or represents a monocyclic 5- or 6-membered heteroaryl radical containing one, two or three nitrogen atoms and/or an oxygen or sulphur atom, or a bicyclic heteroaryl radical consisting of a 5-membered hetero ring of aromatic character having two nitrogen atoms or having one nitrogen atom and/or an oxygen or sulphur atom as ring members and a fused benzene ring, or of a 6-membered hetero ring of aromatic character having one or two nitrogen atoms as ring members and a fused benzene ring, the heteroaryl radicals being bonded by a ring carbon atom to the carbon atom of the double bond and optionally being substituted by hydroxy, lower alkoxy halogen, lower alkyl, halo-lower alkyl and/or nitro; $R_2$ has the meaning of $R_1$ or represents hydrogen; lower alkyl, lower alkenyl or lower alkynyl each optionally substituted by hydroxy, lower alkanoyloxy, benzoyloxy optionally substituted by nitro, halogen lower alkyl and/or lower alkoxy, halogen, lower alkoxy, lower alkenyloxy, lower alkylthio, phenylthio, lower alkylsulphinyl, phenylsulphinyl, lower alkylsulphonyl, nitro, carboxy, cyano, lower alkoxycarbonyl, optionally moro- or di-lower alkylated carbamoyl, amino, lower alkylamino, amino-lower alkylamino wherein the terminal amino group is optionally substituted by lower alkyl, lower alkylene or lower alkylene that is interrupted by an optionally lower alkylated nitrogen atom or an oxygen or sulphur atom, di-lower alkylamino, lower alkyleneamino or lower alkyleneamino that is interrupted by an optionally lower alkylated nitrogen atom or an oxygen or sulphur atom; cycloalkyl or cycloalkyl-lower alkyl each optionally substituted by lower alkyl, hydroxy, lower alkoxy, halogen, carboxy or lower alkoxycarbonyl; phenyl-lower alkyl optionally substituted by loweralkyl, lower alkoxy, halogen or nitro; furyl-, thienyl- or pyridyl-lower alkyl each optionally substituted by lower alkyl, lower alkoxy, halogen or halo-lower alkyl; lower alkanoyl optionally substituted by hydroxy, halogen, lower alkoxy, carboxy, lower alkoxycarbonyl, cyano and/or phenyl optionally substituted by lower alkyl; cycloalkanoyl; benzoyl or naphthoyl each optionally substituted by lower alkyl, hydroxy, halogen, lower alkoxy, amino, lower alkylamino, di-lower alkylamino, lower alkanoylamino, carboxy, lower alkoxycarbonyl, optionally mono- or di-lower alkylated carbamoyl and/or nitro; phenyl-lower alkanoyl; furoyl or thenoyl each optionally substituted by lower alkyl or halogen; pyridoyl optionally substituted by hydroxy, lower alkoxy, halo-lower alkyl and/or cyano; a thioacyl radical of the formula $R_3$—C(=S)— or an iminoacyl radical of the formula $R_3$—C(=NR$_4$)— in which $R_3$ is hydrogen, lower alkyl, phenyl or phenyl-lower alkyl and $R_4$ is lower alkyl, phenyl or phenyl-lower alkyl; carboxy; alkoxycarbonyl having up to 20 carbon atoms; cyano; optionally mono- or di-lower alkylated carbamoyl or carbamoyl substituted by lower alkylene, lower alkenyl, lower alkanoyl or benzoyl; thiocarbamoyl optionally substituted by lower alkyl or lower alkylene; lower alkylthio, phenylthio, phenyl-lower alkylthio, phenylsulphinyl, phenyl-lower alkylsulphinyl, lower alkylsulphonyl, phenylsulphonyl or phenyl-lower alkylsulphonyl wherein the phenyl radicals are optionally substituted by lower alkyl, lower alkoxy, halogen and/or nitro; sulpho; lower alkoxysulphonyl; phenyl-lower alkoxysulphonyl or optionally lower alkylated or phenylated aminosulphonyl; A represents a lower alkylene, lower alkylidene or lower alkenylene radical each of which separates the sulphur atoms by from 1 to 5 carbon atoms and each of which is optionally substituted by oxo, hydroxy, halogen, lower alkanoyloxy, halo-lower alkanoyloxy, benzoyloxy optionally substituted by nitro, loweralkyl and/or lower alkoxy, lower alkoxy, phenyl-lower alkoxy optionally substituted in the phenyl moiety by nitro, halogen, lower alkyl and/or lower alkoxy, phenoxy optionally substituted by nitro, lower alkyl, lower alkoxy and/or halogen, lower alkylthio, phenylthio, phenyl-lower alkylthio, carboxy, lower alkoxycarbonyl, cyano, optionally mono- or di-lower alkylated carbamoyl, amino, lower alkylamino, di-lower alkylamino, lower alkyleneamino, lower alkenylamino, anilino, phenyl-lower alkylamino, lower alkanoylamino, lower alkanesulphonylamino, benzenesulphonylamino optionally substituted by lower alkyl or halogen, cycloalkyl, nitro or phenyl that is optionally substituted by hydroxy, lower alkoxy, halogen, lower alkyl, carboxy, lower alkoxycarbonyl or dilower alkylamino; and n 0 or 1, and pharmaceutically acceptable salts of such compounds that contain a salt-forming group for the treatment of liver diseases.

The invention relates more especially to the use of compounds of the formula I in which $R_1$ represents phenyl or naphthyl each optionally substituted by hydroxy, lower alkoxy, carboxy-lower alkoxy, di-lower alkylamino-lower alkoxy, sulpho-lower alkoxy, hydroxy-lower alkoxy, halogen, lower alkanoyloxy, di-lower alkylamino-lower alkanoyloxy, alkyl having up to 14 carbon atoms, halolower alkyl, di-lower alkylamino-lower alkyl, lower alkanoyl, carboxy, lower alkoxycarbonyl, amino, lower alkylamino, di-lower alkylamino, lower alkyleneamino, lower alkyleneamino that is interrupted by an optionally lower alkylated nitrogen atom or an oxygen or sulphur atom, lower alkanoylamino and/or carboxy-lower alkanoylamino; or represents furyl, thienyl, pyrazolyl, imidazolyl, oxazolyl, isoxazolyl, thiazolyl, pyridyl, pyrimidinyl, indolyl, benzimidazolyl, benzofuranyl, benzothienyl, benzoxazolyl, benzothiazolyl or quinolinyl, said heteroaryl radicals being bonded by a ring carbon atom to the carbon atom of the double bond and optionally being substituted by hydroxy, lower alkoxy, halogen, lower alkyl and/or halo-lower alkyl; $R_2$ has the meaning of $R_1$ or represents hydrogen; lower alkyl; hydroxylower alkyl; halo-lower alkyl; lower alkoxy-lower alkyl; lower alkylthio-lower alkyl: phenylthio-lower alkyl; phenylsulphinyl-lower alkyl; lower alkylsulphonyl-lower alkyl; carboxy-lower alkyl; lower alkoxycarbonyl-lower alkyl; optionally mono- or di-lower alkylated carbamoyl-lower alkyl; di-lower alkylamino-lower alkyl; lower-alkyleneamino-lower-alkyl, wherein the lower alkylene radical is optionally interrupted by an optionally lower alkylated nitrogen atom or an oxygen or sulphur atom; amino-lower alkylamino-lower alkyl wherein the terminal amino group is optionally substituted by lower alkyl or lower alkylene that is optionally interrupted by an optionally lower alkylated nitrogen atom or an oxygen or sulphur atom; lower alkenyl; cycloalkyl; phenyl-lower alkyl optionally substituted by lower alkyl, lower alkoxy or halogen; furyl-, thienyl- or pyridyl-lower alkyl each optionally substituted by lower alkyl or halogen; lower alkanoyl optionally substituted by halogen, carboxy, cyano and/or phenyl; benzoyl optionally substituted by lower alkyl, hydroxy, halogen, lower alkoxy, di-lower alkylamino, lower alkanoylamino, carboxy and/or optionally mono- or di-lower alkylated carbamoyl; phenyl-lower alkanoyl; a thioacyl radical of the formula $R_3$—C(=S) in which $R_3$ represents lower alkyl or phenyl; carboxy; alkoxycarbonyl having up to 20 carbon atoms; cyano; optionally mono- or di-lower alkylated carbamoyl or carbamoyl substituted by lower alkylene or lower alkenyl; thiocarbamoyl optionally substituted by lower alkyl; lower alkylthio, phenylthio, phenyl-lower alkylthio, phenylsulphinyl, lower alkylsulphonyl or phenylsulphonyl wherein the phenyl radicals are optionally substituted by lower alkyl or halogen; sulpho·or optionally lower alkylated or phenylated aminosulphonyl; A represents a lower alkylene, lower alkenylene or lower alkylidene radical each of which separates the sulphur atoms by from 1 to 5 carbon atoms and each of which is optionally substituted by oxo, hydroxy, lower alkanoyloxy, halo-lower alkanoyloxy, benzoyloxy optionally substituted by lower alkyl, carboxy, cyano or optionally mono- or di-lower alkylated carbamoyl; and n is 0 or 1, and pharmaceutically acceptable salts of such compounds that contain a salt-forming group for the treatment of liver diseases.

The invention relates most especially to the use of compounds of the formula I in which $R_1$ represents phenyl optionally substituted by hydroxy, lower alkoxy, for example methoxy, carboxy-lower alkoxy, for example carboxymethoxy, sulpho-lower alkoxy, for example 2-sulphoethoxy, di-lower alkylamino-lower alkoxy, for example 2-di-methylaminoethoxy, halogen, for example fluorine or chlorine, lower alkanoyl, for example valeroyl, lower alkyl, for example methyl, halo-lower alkyl, for example trifluoromethyl, carboxy, amino, di-lower alkylamino, for example dimethylamino, 4-lower alkylpiperazino, for example 4-methylpiperazino, lower alkanoylamino, for example acetylamino and/or carboxy-lower alkanoylamino, for example succinylamino; pyridyl, for example 2- or 3-pyridyl; or thienyl, for example 2-thienyl; $R_2$ represents hydrogen; phenyl optionally substituted by hydroxy, lower alkoxy, for example methoxy, halogen, for example fluorine or chlorine, halo-lower alkyl, for example trifluoromethyl, and/or di-lower alkylamino, for example dimethylamino; lower alkyl, for example methyl; halo-lower alkyl, for example trifluoromethyl; carboxy-lower alkyl, for example carboxymethyl; lower alkoxycarbonyl-lower alkyl, for example ethoxycarbonylmethyl; di-lower alkylamino-lower alkyl, for example dimethylaminomethyl, 2-dimethylaminoethyl or methyl-isopropylaminomethyl; lower alkyl substituted by lower alkyleneamino that is interrupted by an optionally lower alkylated nitrogen atom or an oxygen or sulphur atom, for example pyrrolidinomethyl or morpholinomethyl; phenyl-lower alkyl, for example benzyl; lower alkanoyl, for example acetyl; benzoyl substituted by hydroxy or lower alkoxy, for example methoxy; carboxy; alkoxy-carbonyl having up to 9 carbon atoms, for example methoxycarbonyl, isopropoxycarbonyl or n-octyloxycarbonyl; cyano or di-lower alkylaminosulphonyl, for example dimethylaminosulphonyl; A represents a lower alkylene or lower alkenylene radical each of which separates the sulphur atoms by from 2 to 4 carbon atoms, for example ethylene, 1,3-propylene or 1,4-butylene each of which is optionally substituted by oxo or hydroxy, or vinylene; and n is 0 or 1, and pharmaceutically acceptable salts of such compounds that contain a salt-forming group, for the treatment of liver diseases.

The invention relates especially to the use of compounds of the formula I in which $R_1$ represents phenyl substituted by halogen, for example fluorine, di-lower alkylamino, for example dimethylamino, lower alkoxy, for example methoxy, or halo-lower alkyl, for example trifluoromethyl; or pyridyl, for example 2-pyridyl; $R_2$ represents hydrogen; phenyl optionally substituted by halogen, for example fluorine; lower alkyl, for example methyl; benzoyl substituted by lower alkoxy, for example methoxy; or alkoxycarbonyl having up to 9 carbon atoms, for example isopropoxycarbonyl or n-octyloxycarbonyl; A represents lower alkylene or lower alkenylene each of which separates the sulphur atoms by from 2 to 4 carbon atoms, for example ethylene, 1,3-propylene, 1,4-butylene or vinylene; and n is 0, and pharmaceutically acceptable salts of such compounds that contain a salt-forming group, for the treatment of liver diseases.

The invention relates also to pharmaceutical preparations containing ketenethioacetals of the formula I in which $R_1$ represents aryl or heteroaryl, $R_2$ represents hydrogen, an optionally substituted hydrocarbon radical, heteroaryl, an acyl radical, a group of the formula $-S(O)_m-R_a$ wherein m is 0, 1 or 2 and $R_a$ is an optionally substituted hydrocarbon radical, or represents optionally functionally modified sulpho, A represents an optionally substituted bivalent aliphatic hydrocarbon radical and n is 0 or 1, and pharmaceutically acceptable salts of such compounds that contain a salt-forming group, with the proviso that A is other than 1,3-propylene, 2-phenyl- or 2-lower alkyl-1,3-propylene when $R_1$ and $R_2$ are the same and each represents a phenyl radical optionally substituted in the 4-position by hydroxy or lower alkoxy optionally substituted by lower alkoxy or di-substituted amino and n is 0, with the further proviso that A is other than 3-pyridylvinylene when $R_1$ represents 3-pyridyl, $R_2$ represents hydrogen and n is 0, and with the third proviso that A is other than phenylvinylene when $R_1$ represents phenyl, $R_2$ represents benzoyl and n is 0.

The invention relates especially to pharmaceutical preparations containing compounds of the formula I in which $R_1$ represents a monocyclic or polycyclic aryl radical having up to 20 carbon atoms which is optionally substituted by hydroxy, lower alkoxy, carboxy-lower alkoxy, lower alkoxycarbonyl-lower alkoxy, di-lower alkylamino-lower alkoxy, halo-lower alkoxy, sulpho-lower alkoxy, hydroxy-lower alkoxy, halogen, lower alkanoyloxy, di-lower alkylamino-lower alkanoyloxy, alkyl having up to 20 carbon atoms, lower alkyl substituted by hydroxy, halogen, lower alkoxy or di-lower alkylamino, lower alkanoyl, carboxy, lower alkoxycarbonyl optionally substituted by di-lower alkylamino, phenyl optionally substituted by lower alkyl, lower alkoxy, halogen and/or nitro, amino, lower alkylamino, di-lower alkylamino, lower alkyleneamino, lower alkyleneamino that is interrupted by an optionally lower alkylated nitrogen atom or an oxygen or sulphur atom, lower alkanoylamino and/or carboxy-lower alkanoylamino or represents a monocyclic 5- or 6-membered heteroaryl radical containing one, two or three nitrogen atoms and/or an oxygen or sulphur atom, or a bicyclic heteroaryl radical consisting of a 5-membered hetero ring of aromatic character having two nitrogen atoms or having one nitrogen atom and/or an oxygen or sulphur atom as ring members and a fused benzene ring, or of a 6-membered hetero ring of aromatic character having one or two nitrogen atoms as ring members and a fused benzene ring, the heteroaryl radicals being bonded by a ring carbon atom to the carbon atom of the double bond and optionally being substituted by hydroxy, lower alkoxy, halogen, lower alkyl, halo-lower alkyl and/or nitro; $R_2$ has the meaning of $R_1$ or represents hydrogen; lower alkyl, lower alkenyl or lower alkynyl each optionally substituted by hydroxy, lower alkanoyloxy, benzoyloxy optionally substituted by nitro, halogen, lower alkyl and/or lower alkoxy, halogen, lower alkoxy, lower alkenyloxy, lower alkylthio, phenylthio, lower alkylsulphinyl, phenylsulphinyl, lower alkylsulphonyl, nitro, carboxy, cyano, lower alkoxycarbonyl, optionally mono- or di-lower alkylated carbamoyl, amino, lower alkylamino, amino-lower alkylamino wherein the terminal amino group is optionally substituted by lower alkyl, lower alkylene or lower alkylene that is interrupted by an optionally lower alkylated nitrogen atom or an oxygen or sulphur atom; di-lower alkylamino, lower alkyleneamino or lower alkyleneamino that is interrupted by an optionally lower alkylated nitrogen atom or an oxygen or sulphur atom; cycloalkyl or cycloalkyl-lower alkyl each optionally substituted by lower alkyl, hydroxy, lower alkoxy, halogen, carboxy or lower alkoxycarbonyl; phenyl-lower alkyl optionally substituted by lower alkyl, lower alkoxy, halogen or nitro; furyl-, thienyl- or pyridyl-lower alkyl each optionally substituted by lower alkyl, lower alkoxy, halogen or halo-lower alkyl; lower alkanoyl optionally substituted by hydroxy, halogen, lower alkoxy, carboxy, lower alkoxycarbonyl, cyano and/or phenyl optionally substituted by lower alkyl; cycloalkanoyl; benzoyl or naphthoyl each optionally substituted by lower alkyl, hydroxy, halogen, lower alkoxy, amino, lower alkylamino, di-lower alkylamino, lower alkanoylamino, carboxy, lower alkoxycarbonyl, optionally mono- or di-lower alkylated carbamoyl and/or nitro; phenyl-lower alkanoyl; furoyl or thenoyl each optionally substituted by lower alkyl or halogen; pyridoyl optionally substituted by hydroxy, lower alkoxy, halo-lower alkyl and/or cyano; a thioacyl radical of the formula $R_3-C(=S)-$ or an iminoacyl radical of the formula $R_3-C(=NR_4)-$ in which $R_3$ is hydrogen, lower alkyl, phenyl or phenyl-lower alkyl and $R_4$ is lower alkyl, phenyl or phenyl-lower alkyl; carboxy; alkoxycarbonyl having up to 20 carbon atoms; cyano; optionally mono- or di-lower alkylated carbamoyl or carbamoyl substituted by lower alkylene, lower alkenyl, lower alkanoyl or benzoyl; thiocarbamoyl optionally substituted by lower alkyl or lower alkylene; lower alkylthio, phenylthio, phenyl-lower alkylthio, phenylsulphinyl, phenyl-lower alkylsulphinyl, lower alkylsulphonyl, phenylsulphonyl or phenyl-lower alkylsulphonyl wherein the phenyl radicals are optionally substituted by lower alkyl, lower alkoxy, halogen and/or nitro; sulplo; lower alkoxysulphonyl; phenyl-lower alkoxysulphonyl or optionally lower alkylated or phenylated aminosulphcnyl; A represents a lower alkylene, lower alkylidene or lower alkerylene radical each of which separates the sulphur atoms by from 1 to 5 carbon atoms and each of which is optionally substituted by oxo, hydroxy, halogen, lower alkanoyloxy, halo-lower alkanoyloxy, benzoyloxy optionally substituted by nitro, lower alkyl and/or lower alkoxy, lower alkoxy, phenyllower alkoxy optionally substituted in the phenyl moiety by nitro, halogen, lower alkyl and/or lower alkoxy, phenoxy optionally substituted by nitro, lower alkyl, lower alkoxy and/or halogen, lower alkylthio, phenylthio, phenyl-lower alkylthio, carboxy, lower alkoxycarbonyl, cyano, optionally mono- or di-lower alkylated carbamoyl, amino, lower alkylamino, di-lower alkylamino, lower alkyleneamino, lower alkenylamino, anilino, phenyl-lower alkylamino, lower alkanoylamino, lower alkanesulphonylamino, benzenesulphonylamino optionally substituted by lower alkyl or halogen, cycloalkyl, nitro or phenyl that is optionally substituted by hydroxy, lower alkoxy, halogen, lower alkyl, carboxy, lower alkoxycarbonyl or dilower alkylamino; and n 0 or 1 and pharmaceutically acceptable salts of such compounds that contain a salt-forming group, with the proviso that A is other than 1,3-propylene, 2-phenyl- or 2-lower alkyl-1,3-propylene when $R_1$ and $R_2$ are the same and each represents a phenyl radical optionally substituted in the 4-position by hydroxy or lower alkoxy optionally substituted by lower alkoxy or di-substituted amino and n is 0 and with the further proviso that A is other than phenylvinylene when $R_1$ represents phenyl, $R_2$ represents benzoyl and n is 0.

The invention relates more especially to pharmaceutical preparations containing compounds of the formula I in which $R_1$ represents phenyl or naphthyl each optionally substituted by hydroxy, lower alkoxy, carboxy-lower alkoxy, di-lower alkylamino-lower alkoxy, sulpho-lower alkoxy, hydroxy-lower alkoxy, halogen, lower alkanoyloxy, di-lower alkylamino-lower alkanoyloxy, alkyl having up to 14 carbon atoms, halo-lower alkyl, di-lower alkylamino-lower alkyl, lower alkanoyl, carboxy, lower alkoxycarbonyl, amino, lower alkylamino, di-lower alkylamino, lower alkyleneamino, lower alkyleneamino that is interrupted by an optionally lower alkylated nitrogen atom or an oxygen or sulphur atom, lower alkanoylamino and/or carboxy-lower alkanoylamino; or represents furyl, thie.yl, pyrazolyl, imidazolyl, oxazolyl, isoxazolyl, thiazolyl, pyridyl, pyrimidinyl, indolyl, benzimidazolyl, benzofuranyl, benzothienyl, benzoxazolyl, benzothiazolyl or quinolinyl, said heteroaryl radicals being bonded by a ring carbon atom to the carbon atom of the double bond and optionally being substituted by hydroxy, lower alkoxy, halogen, lower alkyl and/or halo-lower alkyl; $R_2$ has the meaning of $R_1$ or represents hydrogen; lower alkyl; hydroxy-lower alkyl; halo-lower alkyl; lower alkoxy-lower alkyl; lower alkylthio-lower alkyl; phenylthio-lower alkyl; phenylsulphinyl-lower alkyl; lower alkylsulfonyl-lower alkyl; carboxy-lower alkyl; lower alkoxycarbonyl-lower alkyl; optionally mono- or di-lower alkylated carbamoyl-lower alkyl; di-lower alkylamino-lower alkyl; lower-alkyleneamino-lower-alkyl, wherein the lower alkylene radical is optionally interrupted by an optionally lower alkylated nitrogen atom or an oxygen or sulphur atom; amino-lower alkylamino-lower alkyl wherein the terminal amino group is optionally substituted by lower alkyl or lower alkylene that is optionally interrupted by an optionally lower alkylated nitrogen atom or an oxygen or sulphur atom; lower alkenyl; cycloalkyl; phenyl-lower alkyl optionally substituted by lower alkyl, lower alkoxy or halogen; furyl-, thienyl- or pyridyl-lower alkyl each optionally substituted by lower alkyl or halogen; lower alkanoyl optionally substituted by halogen, carboxy, cyano and/or phenyl; benzoyl optionally substituted by lower alkyl, hydroxy, halogen, lower alkoxy, di-lower alkylamino, lower alkanoylamino, carboxy and/or optionally mono- or di-lower alkylated carbamoyl; phenyl-lower alkanoyl; a thioacyl radical of the formula $R_3$—C(=S) in which $R_3$ represents lower alkyl or phenyl; carboxy; alkoxycarbonyl having up to 20 carbon atoms; cyano; optionally mono- or dilower alkylated carbamoyl or carbamoyl substituted by lower alkylene or lower alkenyl; thiocarbamoyl optionally substituted by lower alkyl; lower alkylthio, phenylthio, phenyl-lower alkylthio, phenylsulphinyl, lower alkylsulphonyl or phenylsulphonyl wherein the phenyl radicals are optionally substituted by lower alkyl or halogen; sulpho or optionally lower alkylated or phenylated aminosulphonyl; A represents a lower alkylene, lower alkenylene or lower alkylidene radical each of which separates the sulphur atoms by from 1 to 5 carbon atoms and each of which is optionally substituted by oxo, hydroxy, lower alkanoyloxy, halo-lower alkanoyloxy, benzoyloxy optionally substituted by lower alkyl, carboxy, cyano or optionally mono- or di-lower alkylated carbamoyl; and n is 0 or 1, and pharmaceutically acceptable salts of such compounds that contain a salt-forming group, with the proviso that A is other than 1,3-propylene or 2-lower alkyl-1,3-propylene when $R_1$ and $R_2$ are the same and each represents a phenyl radical optionally substituted in the 4-position by hydroxy or lower alkoxy optionally substituted by di-substituted amino and n is 0.

The invention relates most especially to pharmaceutical preparations containing compounds of the formula I in which $R_1$ represents phenyl optionally substituted by hydroxy, lower alkoxy, for example methoxy, carboxy-lower alkoxy, for example carboxymethoxy, sulpho-lower alkoxy, for example 2-sulphoethoxy, di-lower alkylamino-lower alkoxy, for example 2-dimethylaminoethoxy, halogen, for example fluorine or chlorine, lower alkanoyl, for example valeroyl, lower alkyl, for example methyl, halo-lower alkyl, for example trifluoromethyl, carboxy, amino, di-lower alkylamino, for example dimethylamino, 4-lower alkylpiperazino, for example 4-methylpiperazino, lower alkanoylamino, for example acetylamino and/or carboxy-lower alkanoylamino, for example succinylamino; pyridyl, for example 2- or 3-pyridyl; or thienyl, for example 2-thienyl; $R_2$ represents hydrogen; phenyl optionally substituted by hydroxy. lower alkoxy, for example methoxy, halogen, for example fluorine or chlorine, halo-lower alkyl, for example trifluoromethyl, and/or di-lower alkylamino, for example dimethylamino; lower alkyl, for example methyl; halo-lower alkyl, for example trifluoromethyl; carboxy-lower alkyl, for example carboxymethyl; lower alkoxycarbonyl-lower alkyl, for example ethoxycarbonylmethyl; di-lower alkylamino-lower alkyl, for example dimethylaminomethyl, 2-dimethylaminoethyl or methyl-isopropylaminomethyl; lower alkyl substituted by lower alkyleneamino, that is interrupted by an optionally lower alkylated nitrogen atom or an oxygen or sulphur atom, for example pyrrolidinomethyl or morpholinomethyl; phenyl-lower alkyl, for example benzyl; lower alkanoyl, for example acetyl; benzoyl substituted by hydroxy or lower alkoxy, for example methoxy; alkoxycarbonyl having up to 9 carbon atoms, for example methoxycarbonyl, isopropoxycarbonyl or n-octyloxycarbonyl; cyano or di-lower alkylaminosulphonyl, for example dimethylaminosulphonyl; A represents a lower alkylene or lower alkenylene radical each of which separates the sulphur atoms by from 2 to 4 carbon atoms, for example ethylene, 1,2-propylene or 1,4-butylene each of which is optionally substituted by oxo or hydroxy, or vinylene; and n is 0 or 1, and pharmaceutically acceptable salts of such compounds that contain a salt-forming group, with the proviso that A is other than 1,3-propylene or 2-lower alkyl-1,3-propylene when $R_1$ and $R_2$ are the same and each represents a phenyl radical optionally substituted in the 4-position by hydroxy or lower alkoxy and n is 0.

The invention relates especially to pharmaceutical preparations containing compounds of the formula I in which $R_1$ represents phenyl substituted by halogen, for example fluorine, di-lower alkylamino, for example dimethylamino, lower alkoxy, for example methoxy, or halo-lower alkyl, for example trifluoromethyl; or pyridyl, for example 2-pyridyl; $R_2$ represents hydrogen; phenyl optionally substituted by halogen, for example fluorine; lower alkyl, for example methyl; benzoyl substituted by lower alkoxy, for example methoxy; or alkoxycarbonyl having up to 9 carbon atoms, for example isopropoxycarbonyl or n-octyloxycarbonyl; A represents lower alkylene or lower alkenylene each of which separates the sulphur atoms by from 2 to 4 carbon atoms, for example ethylene, 1,3-propylene, 1,4-butylene or vinylene; and n is 0, and pharmaceutically acceptable salts of such compounds that contain a salt-forming group.

The invention relates also to novel compounds of the formula I in which $R_1$ represents aryl or heteroaryl, $R_2$ represents substituted phenyl, an optionally substituted polycyclic aryl radical, monocyclic heteroaryl containing one, two or three nitrogen atoms and/or an oxygen atom, bicyclic heteroaryl, an optionally substituted aliphatic, cycloaliphatic, cycloaliphatic-lower aliphatic, aromatic-lower aliphatic or heteroaromatic-lower aliphatic hydrocarbon radical, a group of the formula —S(O)$_m$-R$_a$ wherein m is 0, 1 or 2 and R$_a$ is an optionally substituted hydrocarbon radical, the acyl radical of an optionally substituted lower aliphatic, cycloaliphatic, aromatic, aromatic-lower aliphatic or heteroaromatic carboxylic acid, thiocarboxylic acid or iminocarboxylic acid, optionally esterified or amidated carboxy, thiocarbamoyl optionally substituted by lower alkyl or lower alkylene, or optionally functionally modified sulpho, A represents an optionally substituted bivalent aliphatic hydrocarbon radical and n is 0 or 1; or in which $R_1$ represents phenyl disubstituted by optionally etherified or esterified hydroxy, $R_2$ represents hydrogen and A and n have the meanings each given above, with the provisos that A is other than 1,3-propylene, 2-phenyl- or 2-lower alkyl-1,3-propylene or oxalyl when $R_1$ and $R_2$ are the same and each represents a phenyl radical substituted in the 4-position by hydroxy or lower alkoxy optionally substituted by disubstituted amino or lower alkoxy and n is 0, that A is other than carboxymethylene or lower alkoxycarbonylmethylene when $R_1$ represents aryl or heteroaryl, $R_2$ represents optionally esterified or amidated carboxyl and n is 0, that A is other than 1,3-propylene, dibenzoylvinylene or 2-phenyl-2-tert.-butylethylidene when $R_1$ represents phenyl, $R_2$ represents methyl, tert.-butyl or phenylthiomethyl and n is 0, that A is other than 1-(2-tolyl)-2-(4-methoxyphenyl)-vinylene when $R_1$ represents 2-tolyl, $R_2$ represents 4-methoxyphenyl and n is 0, that A is other than mono- or di-substituted vinylene, 2,2-disubstituted ethylidene or 1,1-di-substituted 2-oxoethylene when $R_1$ represents phenyl optionally substituted in the 4-position by fluorine or bromine, $R_2$ represents benzoyl optionally substituted in the 4-position by fluorine or bromine, or formyl or acetyl and n is 0, that A is other than optionally methyl-esterified 1-phenyl1-carboxyethylidene or other than 1-phenyl-2-methoxycarbonylvinylene when $R_1$ represents phenyl-, $R_2$ represents carboxy or methoxycarbonyl and n is 0, that A is other than mono- or di-substituted vinylene or tetramethylethylene when $R_1$ represents phenyl optionally substituted in the 4-position by chlorine or methyl,$R_2$ represents thioformyl, thioacetyl, phenylthiocarbonyl, phenyliminomethyl, methyliminomethyl, N-phenylcarbamoyl or optionally substituted thiocarbamoyl and n is 0, that A is other than ethylene when $R_1$ represents phenyl or 2-pyridyl , $R_2$ represents benzoyl and n is 0, that A is other than 1,3-propylene when $R_1$ represents 2-pyridyl, $R_2$ represents isobutyryl or 3-methylbutyryl and n is 0, and that A is other than ethylene when $R_1$ represents phenyl,$R_2$ represents phenylsulphonyl, methylsulphonyl or benzylsulphonyl and n is 0, salts of such compounds that contain a salt-forming group and processes for their manufacture.

The invention relates especially to compounds of the formula I in which $R_1$ represents a monocyclic or polycyclic aryl radical having up to 20 carbon atoms which is optionally substituted by hydroxy, lower alkoxy, carboxy-lower alkoxy, lower alkoxycarbonyl-lower alkoxy, di-lower alkylamino-lower alkoxy, halo-lower alkoxy, sulpho-lower alkoxy, hydroxy-lower alkoxy, halogen, lower alkanoyloxy, di-lower alkylamino-lower alkanoyloxy, alkyl having up to 20 carbon atoms, lower alkyl substituted by hydroxy, halogen, lower alkoxy or di-lower alkylamino, lower alkanoyl, carboxy, lower alkoxycarbonyl optionally substituted by di-lower alkylamino, phenyl optionally substituted by lower alkyl, lower alkoxy, halogen and/or nitro, nitro, amino, lower alkylamino, di-lower alkylamino, lower alkyleneamino, lower alkyleneamino that is interrupted by an optionally lower alkylated nitrogen atom or an oxygen or sulphur atom, lower alkaroylamino and/or carboxy-lower alkanoylamino; or represents a monocyclic 5- or 6-membered heteroaryl radical consisting of a 5-membered hetero ring of aromatic character having two nitrogen atoms or having one nitrogen atom and/or an oxygen or sulphur atom as ring members and a fused benzene ring, or of a 6-membered hetero ring of aromatic character having one or two nitrogen atoms as ring members and a fused benzene ring, the heteroaryl-radicals being bonded by a ring carbon atom to the carbon atom of the double bond and optionally being substituted by hydroxy, lower alkoxy, halogen, lower alkyl, halo-lower alkyl and/or nitro; $R_2$ represents naphthyl; phenyl or naphthyl each substituted by hydroxy, lower alkoxy, carboxy-lower alkoxy, lower alkoxycarbonyl-lower alkoxy, di-lower alkylamino-lower alkoxy, halo-lower alkoxy, sulpho-lower alkoxy, hydroxy-lower alkoxy, halogen, lower alkanoyloxy, di-lower alkylamino-lower alkanoyloxy, alkyl having up to 20 carbon atoms, lower alkyl substituted by hydroxy, halogen, lower alkoxy, or di-lower alkylamino, lower alkanoyl, carboxy, lower alkoxycarbonyl optionally substituted by di-lower alkylamino, phenyl optionally substituted by lower alkyl, lower alkoxy, halogen and/or nitro, amino, lower alkylamino, di-lower alkylamino, lower alkyleneamino, lower alkyleneamino that is interrupted by an optionally lower alkylated nitrogen atom or an oxygen or sulphur atom, and/or lower alkanoylamino; a monocyclic 5- or 6-membered heteroaryl radical containing one, two or three nitrogen atoms and/or an oxygen atom, or a bicyclic heteroaryl radical consisting of a 5-membered hetero ring of aromatic character having two nitrogen atoms or having one nitrogen atom and/or an oxygen or sulphur atom as ring members and a fused benzene ring, or of a 6-membered hetero ring of aromatic character having one or two nitrogen atoms as ring members and a fused benzene ring, the heteroaryl radicals being bonded by a ring carbon atom to the carbon atom of the double bond and optionally being substituted by hydroxy, lower alkoxy, halogen, lower alkyl, halo-lower alkyl and/or nitro; lower alkyl, lower alkenyl or lower alkynyl each optionally substituted by hydroxy, lower alkanoyloxy, benzoyloxy optionally substituted by nitro, halogen, lower alkyl and/or lower alkoxy, halogen, lower alkoxy, lower alkenyloxy, lower alkylthio, phenylthio, lower alkylsulphinyl, phenylsulphinyl, lower alkylsulphonyl, nitro, carboxy, cyano, lower alkoxycarbonyl, optionally mono- or di-lower alkylated carbamoyl, amino, lower alkylamino, amino-lower alkylamino wherein the terminal amino group is optionally substituted by lower alkyl, lower alkylene or lower alkylene that is interrupted by an optionally lower alkylated nitrogen atom or an oxygen or sulphur atom, di-lower alkylamino, lower alkyleneamino or lower alkyleneamino that is interrupted by an optionally lower alkylated nitrogen atom or an oxygen or sulphur atom; cycloalkyl or cycloalkyl-lower alkyl each optionally substituted by lower alkyl, hydroxy, halogen, lower alkoxy, carboxy or lower alkoxycarbonyl; phenyl-lower alkyl optionally substituted by lower alkyl, halogen, lower alkoxy or nitro; furyl-, thienyl- or pyridyl-lower alkyl each optionally substituted by lower alkyl, lower alkoxy, halogen or halo-lower alkyl; lower alkylthio, phenylthio, phenyl-lower alkylthio, phenylsulphinyl, phenyl-lower alkylsulphinyl, lower alkylsulphonyl, phenylsulphonyl or phenyl-lower alkylsulphonyl wherein the phenyl radicals are optionally substituted by lower alkyl, lower alkoxy, halogen, and/or nitro; lower alkanoyl optionally substituted by hydroxy, halogen, lower alkoxy, carboxy, lower alkoxycarbonyl, cyano and/or phenyl optionally substituted by lower alkyl; cycloalkanoyl; benzoyl or naphthoyl each optionally substituted by lower alkyl, hydroxy, halogen, lower alkoxy amino, lower alkylamino, di-lower alkylamino, lower alkanoylamino, carboxy, lower alkoxycarbonyl, optionally mono- or di-lower alkylated carbamoyl and/or nitro; phenyl-lower alkanoyl; furoyl or thenoyl each optionally substituted by lower alkyl or halogen; pyridoyl optionally substituted by hydroxy, lower alkoxy, halo-lower alkyl and/or cyano; a thioacyl radical of the formula $R_3-C(=S)-$ or an iminoacyl radical of the formula $R_3-C(=NR_4)-$ in which $R_3$ is hydrogen, lower alkyl, phenyl or phenyl-lower alkyl and $R_4$ is lower alkyl, phenyl or phenyl-lower-alkyl; carboxy; alkoxycarbonyl having up to 20 carbon atoms; optionally mono- or di-lower alkylated carbamoyl or carbamoyl substituted by lower alkylene, lower alkenyl, lower alkanoyl or benzoyl; thiocarbamoyl optionally substituted by lower alkyl or lower alkylene; sulpho; lower alkoxysulphonyl; phenyl-lower alkoxysulphonyl or optionally lower alkylated or phenylated aminosulphonyl; A represents a lower alkylene, lower alkylidene or lower alkenylene radical each of which separates the sulphur atoms by from 1 to 5 carbon atoms and each of which is optionally substituted by oxo, hydroxy, halogen, lower alkanoyloxy, halo-lower alkanoyloxy, benzoyloxy optionally substituted by nitro, lower alkyl and/or lower alkoxy, lower alkoxy, phenyl-lower alkoxy optionally substituted in the phenyl moiety by nitro, halogen, lower alkyl and/or lower alkoxy, phenoxy optionally substituted by nitro, lower alkyl, lower alkoxy and/or halogen, lower alkylthio, phenylthio, phenyl-lower alkylthio, carboxy, lower alkoxycarbonyl,-cyano, optionally mono- or di-lower alkylated carbamoyl, amino, lower alkylamino, di-lower alkylamino, lower alkyleneamino, lower alkenylamino, anilino, phenyl-lower alkylamino, lower alkanoylanno, lower alkanesulphonylamino, benzenesulphonylamino optionally substituted by lower alkyl or halogen, cycloalkyl, nitro or phenyl that is optionally substituted by hydroxy, lower alkoxy, halogen, lower alkyl, carboxy, lower alkoxycarbonyl or di-lower alkylamino; and n 0 or 1; or in which $R_1$ represents phenyl disubstituted by hydroxy, lower alkoxy, carboxylower alkoxy, di-lower alkylamino-lower alkoxy, sulpho-lower alkoxy and/or halogen, $R_2$ represents hydrogen and A and n have the meanings each given above, with the provided that A is other than 1,3-propylene, 2-phenyl- or 2-lower alkyl-1,3-propylene or oxalyl when $R_1$ and $R_2$ are the same and each represents a phenyl radical substituted in the 4-position by hydroxy or lower alkoxy optionally substituted by disubstituted amino or lower alkoxy and n is 0, that A is other than carboxymethylene or lower alkoxycarbonylmethylene when $R_1$ represents aryl or heteroaryl $R_2$ represents carboxy, alkoxycarbonyl or optionally substituted carbamoyl and n is 0, that A is other than 1,3-propylene or 2-phenyl-2-tert.-butylethylidene when $R_1$ represents phenyl, $R_2$ represents methyl, tert.-butyl- or phenylthiomethyl and n is 0, that A is other than 1-(2-tolyl)-2-(4-methoxyphenyl)-vinylene when $R_1$ represents 2-tolyl, R2 represents 4-methoxyphenyl and n is 0, that A is other than vinylene mono- or di-substituted as indicated above, ethylidene 2,2-disubstituted or 2-oxoethylene 1,1-disubstituted as indicated above when $R_1$ represents phenyl optionally substituted in the 4-position by fluorine or bromine, $R_2$ represents benzoyl optionally substituted in the 4-position by fluorine or bromine, or formyl or acetyl and n is 0, that A is other than optionally methyl-esterified 1-phenyl-1-carboxyethylidene or other than 1-phenyl-2-methoxycarbonylvinylene when $R_1$ represents phenyl, $R_2$ represents carboxy or methoxycarbonyl and n is 0, that A is other than vinylene mono- or di-substituted as indicated above or tetramethylethylene when $R_1$ represents phenyl optionally substituted in the 4-position by chlorine or methyl, $R_2$ represents thioformyl, thioacetyl, phenylthiocarbonyl, phenyliminomethyl, methyliminomethyl or thiocarbamoyl optionally substituted as indicated above and n is 0, that A is other than ethylene when $R_1$ represents phenyl or 2-pyridyl, $R_2$ represents benzoyl and n is 0, that A is other than 1,3-propylene when $R_1$ represents 2-pyridyl, $R_2$ represents isobutyryl or 3-methylbutyryl and n is 0, and that A is other than ethylene when $R_1$ represents phenyl, $R_2$ represents phenylsulphonyl, methylsulphonyl or benzylsulphonyl and n is 0, salts of such compounds that contain a salt-forming group and processes for their manufacture.

The invention relates more especially to compounds of the formula I in which $R_1$ represents phenyl or naphthyl each optionally substituted by hydroxy, lower alkoxy, carboxy-lower alkoxy, di-lower alkylamino- lower alkoxy, sulpho- lower alkoxy, hydroxy-lower alkoxy, halogen, lower alkanoyloxy, di-lower alkylamino-lower alkanoyloxy, alkyl having up to 14 atoms, halo-lower alkyl, di-lower alkyl-amino-lower alkyl, lower alkanoyl, carboxy, lower alkoxycarbonyl, amino, lower alkylamino, di-lower alkylamino, lower alkyleneamino, lower alkyleneamino that is interrupted by an optionally lower alkylated nitrogen atom or an oxygen or sulphur atom, lower alkanoylamino and/or carboxy-lower alkanoylamino; or represents furyl, thienyl, pyrazolyl, imidazolyl, oxazolyl, isoxazolyl, thiazolyl, pyridyl, pyrimidinyl, indolyl, benzimidazolyl, benzofuranyl, benzothienyl, benzoxazolyl, benzothiazolyl or quinolinyl, said heteroaryl radicals being bonded by a ring carbon atom to the carbon atom of the double bond and optionally being substituted by hydroxy, lower alkoxy, halogen, lower alkyl and/or halo-lower alkyl; $R_2$ represents phenyl substituted by hydroxy, lower alkoxy, carboxy-lower alkoxy, di-lower alkylamino-lower alkoxy, sulpho-lower alkoxy, hydroxy-lower alkoxy, halogen, lower alkanoyloxy, di-lower alkylamino-lower alkanoyloxy, alkyl having up to 14 carbon atoms, halo-lower alkyl, di-lower aikylamino-lower alkyl, lower alkanoyl, carboxy, lower alkoxycarbonyl, amino, lower alkylamino, di-lower alkylamino, lower alkyleneamino, lower alkyleneamino that is interrupted by an optionally lower alkylated nitrogen atom or an oxygen or sulphur atom, and/or lower alkanoylamino; or represents furyl, pyrazolyl, imidazolyl, oxazolyl, isoxazolyl, pyridyl, pyrimidinyl, indolyl, benzimidazolyl, benzofuranyl, benzothienyl, benzoxazolyl, benzothiazolyl or quinolinyl, said heteroaryl radicals being bonded by a ring carbon atom to the carbon atom of the double bond and optionally being substituted by hydroxy, lower alkoxy, halogen, lower alkyl and/or halo-lower alkyl; lower alkyl; hydroxy-lower alkyl; halo-lower alkyl; lower alkoxy-lower alkyl; lower alkylthiolower alkyl; phenylthio-lower alkyl; phenylsulphinyl lower alkyl; lower alkylsulphonyl-lower alkyl; carboxy-lower alkyl; lower alkoxycarbonyl-lower alkyl; optionally mono- or di-lower alkylated carbamoyl-lower alkyl; di-lower alkylamino-lower alkyl; lower-alkyleneamino-lower alkyl wherein the lower alkylene radical is optionally interrupted by an optionally lower alkylated nitrogen atom or an oxygen or sulphur atom; amino-lower alkylamino-lower alkyl wherein the terminal amino group is optionally substituted by lower alkyl or lower alkylene that is optionally interrupted by an optionally lower alkylated nitrogen atom or an oxygen or sulphur atom; lower alkenyl; cycloalkyl; phenyl-lower alkyl optionally substituted by lower alkyl, lower alkoxy or halogen; furyl-, thienyl- or pyridyl-lower alkyl each optionally substituted by lower alkyl or halogen; lower alkylthio, phenylthio, phenyl-lower alkylthio, phenylsulphinyl, lower alkylsulphonyl or phenylsulphonyl wherein the phenyl radicals are optionally substituted by lower alkyl or halogen; lower alkanoyl optionally substituted by halogen, carboxy, cyano and/or phenyl; benzoyl optionally substituted by lower alkyl, hydroxy, halogen, lower alkoxy, di-lower alkylamino, lower alkanoylamino, carboxy and/or optionally mono- or di-lower alkylated carbamoyl; phenyl-lower alkanoyl; a thioacyl radical of the formula $R_3$—C(=S) in which $R_3$ represents lower alkyl or phenyl; carboxy; alkoxycarbonyl having up to 20 carbon atoms; optionally mono- or di-lower alkylated carbamoyl or carbamoyl substituted by lower alkylene or lower alkenyl; thiocarbamyl optionally substituted by lower alkyl; sulpho or optionally lower alkylated or phenylated aminosulphonyl; A represents a lower alkylene, lower alkenylene or lower alkylidene radical each of which separates the sulphur atoms by from 1 to 5 carbon atoms and each of which is optionally substituted by oxo, hydroxy, lower alkanoyloxy, halo-lower alkanoyloxy, benzoyloxy optionally substituted by lower alkyl, carboxy, cyano or optionally mono- or di-lower alkylated carbamoyl; and n is 0 or 1 or in which R represents phenyl disubstituted by hydroxy, lower alkoxy or halogen, $R_2$ represents hydrogen and A and n have the meanings each given above, with the provisos that A is other then 1,3-propylene, 2-lower alkyl-1,3-propylene or oxalyl when $R_1$ and $R_2$ are the same and each represents a phenyl radical substituted in the 4-position by hydroxy or lower alkoxy optionally substituted by disubstituted amino and n is 0, that A is other than carboxymethylene when $R_1$ represents aryl or heteroaryl $R_2$ represents carboxy, alkoxycarbonyl or optionally substituted carbamoyl and n is 0, that A is other than 1,3-propylene when $R_1$ represents phenyl, $R_2$ represents methyl, tert.-butyl or phenylthiomethyl and n is 0, that A is other than vinylen mono- or disubstituted as indicated above, ethylidene 2,2-di-substituted as indicated above or 2-oxoethylene 1,1di-substituted as indicated above when $R_1$ represents phenyl optionally substituted in the 4-position by fluorine or bromine, $R_2$ represents benzoyl optionally substituted in the 4-position by fluorine or bromine, or formyl or acetyl and n is 0, that A is other than vinylene mono- or di-substituted as indicated above or tetramethylethylene when $R_1$ represents phenyl optionally substituted in the 4-position by chlorine or methyl, $R_2$ represents thioacetyl, phenylthiocarbonyl, or thiocarbamoyl optionally substituted as indicated above and n is 0, that A is other than ethylene when $R_1$ represents phenyl or 2-pyridyl, $R_2$ represents benzoyl and n is 0, that A is other than 1,3-propylene when $R_1$ represents 2-pyridyl, $R_2$ represents isobutyryl or 3-methylbutyryl and n is 0, and that A is other than ethylene when $R_1$ represents phenyl, $R_2$ represents phenylsulphonyl or methylsulphonyl and n is 0, salts of such compounds that contain a salt-forming group and processes for their manufacture.

The invention relates above all to compounds of the formula I in which $R_1$ represents phenyl optionally substituted by hydroxy, lower alkoxy, for example methoxy, carboxy-lower alkoxy, for example carboxymethoxy, sulpho-lower alkoxy, for example 2-sulphoethoxy, di-lower alkylamino-lower alkoxy, for example 2-dimethylaminoethoxy, halogen, for example fluorine or chlorine, lower alkanoyl, for example valeroyl, lower alkyl, for example methyl, halo-lower alkyl, for example trifluoromethyl, carboxy, amino, di-lower alkylamino, for example dimethylamino, 4-lower alkylpiperazino, for example 4-methylpiperazino, lower alkanoylamino, for example acetylamino and/or carboxy-lower alkanoylamino, for example succinylamino; pyridyl, for example 2- or 3-pyridyl; or thienyl, for example 2-thienyl; $R_2$ represents phenyl substituted by hydroxy, lower alkoxy, for example methoxy, carboxy-lower alkoxy, for example carboxymethoxy, halogen, for example fluorine or chlorine, halo-lower alkyl, for example trifluoromethyl, carboxy and/or di-lower alkylamino, for example dimethylamino; lower alkyl, for example methyl; phenyl-lower alkyl, for example benzyl; halo-lower alkyl, for example trifluoromethyl; carboxy-lower alkyl, for example carboxymethyl; lower alkoxycarbonyl-lower alkyl, for example ethoxycarbonylmethyl; di-lower alkylamino-lower alkyl, for example dimetylaminomethyl, 2-dimethylaminoethyl or methyl-isopropylaminomethyl; lower alkyl substituted by lower alkyleneamino that is interrupted by an optionally lower alkylated nitrogen atom or an oxygen or sulphur atom, for example pyrrolidinomethyl or morpholinomethyl; benzoyl substituted by hydroxy or lower alkoxy, for example methoxy; carboxy; alkoxycarbonyl having up to 9 carbon atoms, for example methoxycarbonyl, isopropoxycarbonyl or n-octyloxycarbonyl; or di-lower alkylaminosulphonyl, for example dimethylaminosulphonyl; A represents a lower alkylene or lower alkenylene radical each of which separates the sulphur atoms by from 2 to 4 carbon atoms, for example ethylene, 1,3-propylene or 1,4-butylene each of which is optionally substituted by oxo or hydroxy, or vinylene; and n is 0 or 1, or in which $R_1$ represents phenyl disubstituted by lower alkoxy, for example methoxy, $R_2$ represents hydrogen and A and n have the meanings given above, with the provisos that A is other than 1,3-propylene, 2-lower alkyl-1,3-propylene or oxalyl when $R_1$ and $R_2$ are the same and each represents a phenyl radical substituted in the 4-position by hydroxy or lower alkoxy and n is 0, and that A is other than 1,3-propylene when $R_1$ represents phenyl, $R_2$ represents methyl or tert.-butyl and n is 0, pharmaceutically acceptable salts of such compounds that contain a salt-forming group and processes for their manufacture.

The invention relates especially to compounds of the formula I in which $R_1$ represents phenyl substituted by halogen, for example fluorine, or halo-lower alkyl, for example trifluoromethyl; or pyridyl, for example 2-pyridyl; $R_2$ represents phenyl substituted by halogen, for example fluorine; lower alkyl, for example methyl; phenyl-lower alkyl, for example benzyl; benzoyl substituted by lower alkoxy, for example methoxy; or alkoxycarbonyl having up to 9 carbon atoms, for example isopropoxycarbonyl or n-octyloxycarbonyl; A represents lower alkylene or alkenylene each of which separates the sulphur atoms by from 2 to 4 carbon atoms, for example ethylene, 1,3-propylene 1,4-butylene or vinylene; and n is 0; or in which $R_1$ represents phenyl, $R_2$ represents phenyl substituted by di-lower alkylamino, for example diemthylamino, and A and n have the meanings given above; or in which $R_1$ represents phenyl disubstituted by lower alkoxy, for example methoxy, $R_2$ represents hydrogen and A and n have the meanings given above, pharmaceutically acceptable salts of such compounds that contain a salt-forming group and processes for their manufacture.

The compounds of the present invention are obtained according to processes known per se.

Compounds of the formula I and salts of such compounds that have a salt-forming group are manufactured, for example, by (a) reacting a compound of the formula

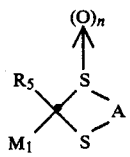
(II)

in which $R_5$ represents a leaving group, $M_1$ is a metal radical and A and n have the meanings given under formula I, with a compound of the formula $R_1$—C(= O)—$R_2$ (III) in which $R_1$ and $R_2$ have the meanings given under formula I, or (b) for the manufacture of a compound of the formula I in which n is 0, reacting a compound of the formula

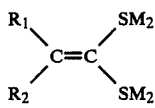
(IV)

in which $M_2$ is a metal radical and $R_1$ and $R_2$ have the meanings given under formula I, with an agent capable of introducing the radical A, or (c) treating a compound of the formula

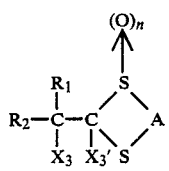
(V)

in which one of the radicals $X_3$ and $X_3'$ *is a leaving group and the other is hydrogen, and* $R_1$, $R_2$, A and n have the meanings given under formula I, with an eliminating agent, or (d) for the manufacture of a compound of the formula I, in which n is 0, treating a compound of the formula $R_1R_2C=R_6$ (VI) with a compound of the formula

(VII)

in which one of the radicals $R_6$ and $R_7$ is a phosphoranylidene group and the other is oxygen or sulphur, and in which $R_1$, $R_2$ and A have the meanings given under formula I, or (e) for the manufacture of a compound of the formula I, in which n is 0, reacting a compound of the formula

(VIII)

in which $X_4$ is a functionally modified hydroxy group or an etherified mercapto group, $Y_1$ represents the radical $R_2$ and $Y_2$ is a functionally modified hydroxy group or a disubstituted amino group or in which $Y_1$ and $Y_2$ together represent a carbon-carbon bond and $X_4$ is a functionally modified hydroxy group, and $R_1$ and $R_2$ have the meanings given under formula I, with a dithiol compound of the formula HS—A—SH (IX) in which A has the meaning given under formula I, or (f) for the manufacture of a compound of the formula I in which n is 0, reacting a nitrile of the formula

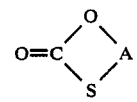
(X)

in which $R_1$ and $R_2$ have the meanings given under formula I, with a compound of the formula HS—A—SH (IX) in which A has the meaning given under formula I, or (g) for the manufacture of a compound of the formula I in which n is 0, treating a monothiocarbonate of the formula

(XI)

in which A has the meaning given under formula I, with a thioamide of the formula

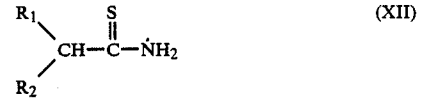
(XII)

in which $R_1$ and $R_2$ have the meanings given under formula I, or (h) treating a carbenium salt of the formula

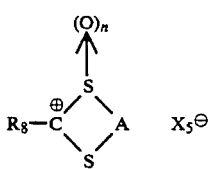

in which $R_8$ is an etherified mercapto group, $X_5^\ominus$ is an anion and A has the meaning given under formula I, with a methylene compound of the formula $R_1$—$CH_2$—$R_2$ (IVc) in which $R_1$ and $R_2$ have the meanings given under formula I, or (i) for the manufacture of a compound of the formula I in which n is 0, cyclising a compound of the formula

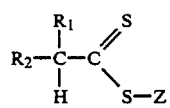

in which Z is a radical which is converted by cyclisation into the radical A, and $R_1$, $R_2$ and A have the meanings given under formula I, or (j) for the manufacture of a compound of the formula I in which is 0, treating a compound of the formula

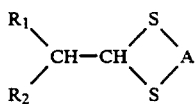

in which $R_1$, $R_2$ and A have the meanings given under formula I, with a dehydrogenating agent, or (k) for the manufacture of a compound of the formula I in which n is 0 and $R_2$ is other than acyl, treating a compound of the formula

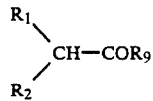

in which $R_9$ is an etherified hydroxy group and $R_1$ and $R_2$ have the meanings given under formula I, with an aluminium compound of the formula $A[-S-Al(R_{10})_2]_2$ (XVII) in which $R_{10}$ is lower alkyl and A has the meaning given under formula I, or (l) for the manufacture of a compound of the formula I in which $R_2$ is an optionally substituted hydrocarbon radical having at least one α-hydrogen atom and n, $R_1$ and A have the meanings given under formula I, isomerising a compound of the formula

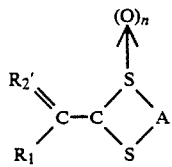

in which $R_2'$ is an optionally substituted hydrocarbylidene radical, or (m) for the manufacture of a compound of the formula I in which $R_2$ is a thioacyl radical of the formula $R_3$—C(=S)— or an iminoacyl radical of the formula $R_3$—C(=NR$_4$)— in which $R_3$ represents hydrogen, lower alkyl, phenyl or phenyl-lower alkyl and $R_4$ represents lower alkyl, phenyl or phenyl-lower alkyl, or a thiocarbamoyl group optionally substituted by lower alkyl, A represents a substituted ethylene or a substituted vinylene group, n is 0 and $R_1$ has the meaning given under formula I, treating a compound of the formula

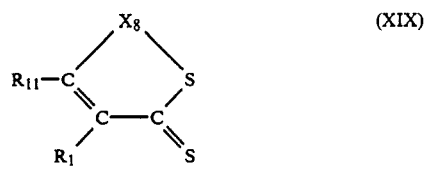

in which $R_{11}$ is synonymous with $R_3$, or represents amino optionally mono- or disubstituted by lower alkyl or substituted by lower alkylene, or is mercapto, and $X_8$ is a sulphur atom or an imino group optionally substituted by lower alkyl, with a bivalent alkylating agent capable of introducing the group A, or (n) for the manufacture of a compound of the formula I in which $R_2$ represents hydrogen, n is 0 and A and $R_1$ have the meanings given under formula I, treating a compound of the formula

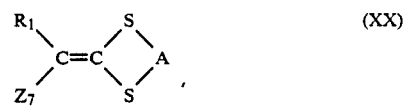

in which $Z_7$ is a phosphonium group, with a hydrolysing agent, or (o) for the manufacture of a compound of the formula I, in which $R_2$ is hydrogen, an optionally substituted hydrocarbon radical, aryl or heteroaryl, A is a vinylene radical of the formula —C($R_1$)=C($R_2$)—, n is 0 and $R_1$ has the meaning given under formula I, splitting off nitrogen from a thiadiazole of the formula

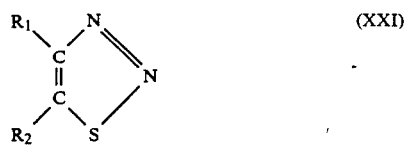

wherein the radicals $R_1$ and $R_2$ may be interchanged, or (p) for the manufacture of a compound of the formula I in which A is an oxoethylene radical of the formula —C($R_1$,$R_2$)—CO—, n is 0 and $R_1$ and $R_2$ have the meanings given under formula I, reacting a diazoketone of the formula $R_1$—C(=O)—C(=N$_2$)—$R_2$ (XXII), wherein the radicals $R_1$ and $R_2$ may be interchanged, with carbon disulphide, or (q) for the manufacture of a compound of the formula I, in which n is 0, treating a compound of the formula

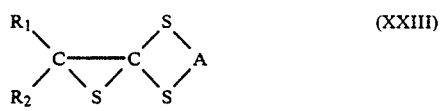

in which $R_1$, $R_2$ and A have the meanings given under formula I, with a desulphurizing agent, functional groups in the starting compounds of the formulae II -

XXIII if necessary being protected, and converting in a resulting compound of the formula I protected functional groups present into the free functional groups, and, if desired, converting a resulting compound of the formula I into another compound of the formula I, and/or, if desired, converting a resulting salt into the free compound or into a different salt, and/or, if desired, converting a resulting free compound of the formula I having a salt-forming group into a salt and/or, if desired, separating a resulting mixture of isomeric compounds of the formula I into the individual isomers.

Process (a)

In a compound of the formula II, a leaving group $R_5$ is, for example, an organic silyl or stannyl group or a boronic ester radical. An organic silyl group $R_5$ is especially a tri-substituted organic silyl group in which the silicon atom contains as substituents preferably lower alkyl, for example methyl, ethyl or tert.-butyl, aryl, for example phenyl, or aryl-lower alkyl, for example benzyl.

Corresponding silyl groups are especially tri-lower alkylsilyl, for example trimethylsilyl, or triarylsilyl, for example triphenylsilyl. An organic stannyl group $R_5$ is especially a tri-lower alkyl stannyl group, for example triethylstannyl, tri-n-butylstannyl or preferably trimethylstannyl. A boronic ester radical $R_5$ is a cyclic or acylic ester radical of the formula

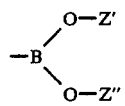

wherein Z' and Z" are the same or different lower alkyl groups, for example methyl, ethyl, isopropyl or isobutyl, or together represent a lower alkylene group, for example ethylene, 1,3-propylene or 2,2-dimethyl-1,3-propylene. A suitable metal radical $M_1$ is especially an alkali metal radical, preferably lithium.

The reaction of compounds of the formulae II and III is carried out in a conventional manner, advantageously in an inert solvent, such as an ether, for example diethyl ether, tetrahydrofuran or dimethoxyethane, or in a hydrocarbon, for example hexane or benzene, or mixtures thereof, at room temperature or at reduced or elevated temperatures, for example at about −80° to about 60° C., if necessary, under an inert gas atmosphere, for example under a nitrogen atmosphere.

The preferred embodiment of this process is, in particular, the reaction of a compound of the formula II in which $R_5$ is trimethylsilyl and M represents lithium, with an oxo compound of the formula III.

The starting materials of the formulae II and III are known or, if novel, can be prepared by methods known per se.

The organometallic compounds of the formula II are advantageously prepared in situ, for example by treating a compound of the formula

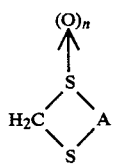 (IIa)

in an inert solvent, preferably the one used in the subsequent reaction, for example tetrahydrofuran, at low temperatures, for example at about −20° to about −80° C., with a metallating agent, such as a lower alkyl or phenyl alkalimetal compound, for example n-butyllithium and a silylating or stannylating agent of the formula $R_5$-Cl (IIb). If the boronic ester method is chosen, the compound of the formula IIa is treated with, for example, trimethylborate, subsequently with a mineral acid, for example hydrochloric acid, and then with an esterifying agent in order to introduce the groups Z' and Z", and by reacting the compound so obtained of the formula

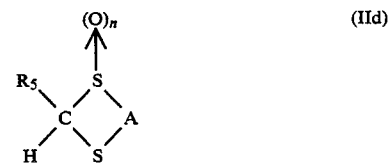 (IId)

with a second equivalent of the metallating agent, for example n-butyllithium, immediately afterwards. The resulting compound of the formula II can be used directly in the above process (a).

Process (b)

In a starting material of the formula IV a metal radical $M_2$ is, for example, a radical of the formula $M_2^+$ or $M_2^{2+}/2$ in which $M_2^+$ is especially an alkali metal cation, for example a lithium, sodium or potassium cation, and $M_2^{2+}/2$ is especially an alkaline earth metal cation, for example a calcium cation.

An agent which introduces the radical A is, for example, a compound of the formula $X_1-A-X_1'$ (IVa) in which $X_1$ and $X_1'$ represent the same or different radicals that can be replaced by nucleophilic substitution, or a compound of the formula $X_2-A'-X_2'$ (IVb) in which $X_2$ and $X_2'$ are radicals that are susceptible to thiol addition reactions and, after the thiol addition reaction has been performed, together with the group A' form a radical A, or in which one of the radicals $X_2$ and $X_2'$ is such a radical and the other is a radical that can be replaced by nucleophilic substitution.

In a starting material of the formula IVa or IVb radicals that can be replaced by nucleophilic substitution are, for example, reactive esterified hydroxy groups, in particular halogen, especially chlorine, bromine or iodine, aromatic or aliphatic sulphonyloxy, especially p-toluenesulphonyloxy or methanesulphonyloxy, or acyloxy, for example unsubstituted or substituted lower alkanoyloxy or benzoyloxy, especially acetoxy or trifluoroacetoxy. Further replaceable radicals are quaternary ammonium groups, especially tri-lower alkylammonium groups, for example triethylammonium groups, and sulphonium groups, especially di-lower alkylsulphonium groups, for example dimethylsulphonium groups. Radicals $X_2$ and/or $X_2'$ that are susceptible to thiol addition reactions contain, for example, oxo groups or carbon-carbon double or triple bonds, especially such that are adjacent to an electron-attracting substituent, for example a carbonyl group or a cyano group.

Suitable starting compounds of the formula IVb include, inter alia, α, β-unsaturated (olefinic or acetylenic) carbonyl compounds, α,β- or γ-halocarbonyl compounds and acetylene dicarboxylic acid derivatives.

The substitution and/or addition is effected in a conventional manner in an inert solvent, for example a loweralkanol, such as methanol or tert.-pentanol, an ether, such as diethyl ether or tetrahydrofuran, a dipolar aprotic solvent, such as dimethyl sulphoxide or dimethylformamide, water or mixtures therof, at room temperature or at elevated or reduced temperature, for example at about −50° to about 100° C., especially at about 20° to about 50° C.

The starting materials of the formulae IV, IVa and IVb are known or, if they are novel, can be prepared by methods known per se.

The dithiolate compounds of the formula IV are advantageously prepared in situ, for example by treating a methylene compound of the formula $R_1$—$CH_2$—$R_2$ (IVc) in an inert solvent, especially one of those mentioned above, with two equivalents of a basic condensation agent, such as a hydride, lower alkoxide, phenoxide, amide or hydroxide of an alkali or alkaline earth metal, for example sodium hydride, sodium methoxide, sodium tert.-pentanolate, lithium 2,6-di-tert.-butyl-4-methyl-phenoxide, sodium amide, lithium diisopropylamide, lithium dicyclohexylamide or potassium hydroxide, and carbon disulphide. The resulting dithiolate of the formula IV can be treated directly with the compound of the formula $X_1$—A—$X_1'$ (IVa) or $X_2$—A'—$X_2'$ (IVb) as described above.

In a further in situ procedure, a mixture consisting of the methylene compound of the formula (IVc), carbon disulphide and the compound of the formula IVa or IVb which have been dissolved in an inert solvent, for example methynechloride or in an excess of carbon disulphide, is treated with a strong aqueous base, for example with a 50% sodium hydroxide solution, in the presence of a phase transfer catalyst, for example tetrabutylammonium chloride. Alternatively, the above mixture dissolved in an inert solvent can be treated with an alkali metal carbonate, for example potassium carbonate, in the presence of a macrocyclic polyether ("crown ether").

Process (c)

In a starting material of the formula V, a leaving group $X_3$ or $X_3'$ is a radical which together with the hydrogen atom $X_3'$ and $X_3$, respectively, in the β-position is susceptible to α, β-elimination Such groups $X_3$ or $X_3'$ are, for example, hydroxy, reactive esterified hydroxy, etherified hydroxy, cyano, etherified mercapto or disubstituted amino, furthermore a quaternary ammonium group or a sulphonium group together with a customary anion, for example an inorganic anion, especially chloride or bromide, neutralizing the positive charge at the nitrogen atom and the sulphur atom, respectively. Suitable reactive esterified hydroxy groups, quaternary ammonium groups and sulphonium groups are especially those described above in connection with the definition of the radicals $X_1$, $X_1'$, $X_2$ and $X_2'$ in process (b). Etherified hydroxy is, for example, hydroxy etherified by aliphatic or araliphatic alcohols, such as lower alkoxy, for example methoxy or ethoxy, or benzyloxy. Etherified mercapto is, for example, mercapto substituted by aliphatic or araliphatic radicals, such as lower alkylthio, for example methylthio, ethylthio, n-propylthio or n-butylthio, or benzylthio. Di-substituted amino is, for example, di-lower alkylamino, such as dimethylamino or diethylamino, or lower alkyleneamino, such as pyrrolidin-l-yl or piperidino. In particular, $X_3$ or $X_3'$ represents hydroxy or halogen, for example chlorine.

An eliminating agent is an agent which facilitates the elimination of the radical $X_3$ or $X_3'$ together with the hydrogen atom in the β-position, for example an agent which facilitates the elimination of water, a compound of the formula H—$X_3$ in which $X_3$ represents, for example, cyano, reactive esterified hydroxy, etherified mercapto or etherified hydroxy, or a secondary amine, a tertiary amine or a sulphide together with the adjacent hydrogen atom. Suitable agents which give rise to the elimination of water are, for example, mineral acids, for example hydrochloric acid, sulphuric acid or phosphoric acid, alkali metal hydrogen sulphate, for example potassium hydrogen sulphate, or a strong organic acid, in particular p-toluene-sulphonic acid. Suitable agents which effect the elimination of a corresponding acid, a mercaptan, an alcohol or a secondary amine, or a tertiary amine or a sulphide together with the adjacent hydrogen atom are, for example, organic bases such as tertiary amines, for example pyridine, or a tri-lower alkylamine, for example triethylamine, or an alkali lower alkoxide, for example sodium ethoxide or, in particular, potassium tert.-butoxide.

The elimination is carried out in a conventional manner. If water is to be eliminated, the compound of the formula V is preferably treated with a catalytic amount of the eliminating agent, for example toluenesulphonic acid, in an inert solvent, for example a halogenated hydrocarbon, for example chloroform or carbon tetrachloride, or a hydrocarbon, for example hexane, benzene or toluene, at room temperature or at elevated temperature, for example at 20° to 110° C., especially at the boiling point of the solvent used, preferably with azeotropic removal of the water being produced. If an acid, an alcohol, a mercaptan or a secondary amine, or a tertiary amine or a sulphide together with the hydrogen atom in the β-position is to be eliminated, the compound of the formula V is treated with a molar amount of an organic base in an inert solvent, such as a lower alkanol, for example ethanol or tert.-butanol, an aliphatic ether, for example tetrahydrofuran or diethyl ether, a hydrocarbon, for example benzene, or a halogenated hydrocarbon, for example methylene chloride, or in mixtures thereof, at room temperature or, if necessary, at reduced or elevated temperature, for example at 0° to 120° C., advantageously at 20° to 60° C.

The starting materials of the formula V are known or, if novel, can be prepared in a manner known per se.

Compounds of the formula V in which $X_3$ represents hydroxy can be obtained, for example, by reacting a compound of the formula

(IIa)

with a metallating agent, for example n-butyllithium, and treating the resulting lithium salt with a carbonyl compound of the formula $R_1$—C(=O)—$R_2$ (III).

Compounds of the formula V in which $X_3$ represents a reactive esterified hydroxy group can be prepared, for example, by treating the corresponding hydroxy derivative with an esterifying agent, for example with thionyl chloride, phosphorus tribromide, acetyl chloride or methanesulphonyl chloride, in the presence of an organic base, for example one of those mentioned above. If two equivalents of the base are used, the resulting acylation product is converted in situ into the corresponding compound of the formula I.

Compounds of the formula V in which $X_3$ represents cyano, etherified hydroxy, etherified mercapto, a tertiary ammonium group or a sulphonium group can be prepared, for example, by treating the corresponding chloro or methanesulphonyloxy derivative with a cyanide, an alcohol, a mercaptan, a tertiary amine and a sulphide, respectively.

Compounds of the formula V in which $X_3'$ represents a di-substituted amino group can be prepared, for example, by reacting an ammonium compound of the formula

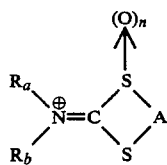

(Va)

wherein, for example, $R_a$ and $R_b$ together represent a lower alkylene group, with a reactive methylene compound of the formula $R_1$—$CH_2$—$R_2$ (IVc) in the presence of a base. The resulting intermediate of the formula V ($X_3'$: $R_a$, $R_b$-di-substituted amino) can be converted in situ into the compound of the formula I by heating in the presence of an excess amount of the base used.

Process (d)

A phosphoranylidene group is a group of the formula=$P(Z_1,Z_2,Z_3)$ in which $Z_1$, $Z_2$ and $Z_3$ represent the same or different lower alkoxy groups, for example methoxy, ethoxy or n-butoxy, lower alkyl groups, for example ethyl, n-propyl or n-butyl, or phenyl groups, or a group of the formula=$P(-O^-M_3^+)(Z_4)(Z_5)$ in which $M_3^+$ is the cation of a strong base, such as an alkali metal cation, for example lithium, sodium or potassium, and $Z_4$ and $Z_5$ represent lower alkoxy, for example methoxy, ethoxy, n-propoxy or n-butoxy, and/or phenyl groups. The preferred phosphoranylidene group is diethylphosphono together with an alkali metal ion, for example sodium.

The reaction is carried out in a manner known to be suitable for Wittig condensations, in the presence of an inert solvent, such as a hydrocarbon, for example hexane or toluene, a halogenated hydrocarbon, for example methylene chloride, an ether, for example diethyl ether or tetrahydrofuran, dimethylformamide, or a lower alkanol, for example methanol, or in a mixture thereof, in a temperature range of about −80° to about 130° C., depending on the reactivity of the reagents and on the choice of the reacting phosphonium compound, and, if necessary, in an inert gas atmosphere, for example an argon or nitrogen atmosphere.

With the exception of the corresponding tri-lower alkoxy phosphoranylidene compounds, the phosphoranylidene compounds of the formulae VI or VII are preferably prepared in situ, starting from the phosphoranes of the formula ($R_1$, $R_2$)CH-$Y_3$ (VIa) or

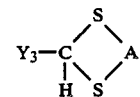

(VIIa)

in which $Y_3$ is a group of the formula —$P^⊖(Z_1Z_2 Z_3)$ $Z_6^⊖$ or a group of the formula —$P^⊕(—O^⊖)(Z_4)(Z_5)$ in which $Z_6^⊖$ is a customary anion, such as a halide, for example chloride or bromide anion. Upon treatment with a suitable basic reagent, the compounds of the formulae VIa and VIIa are converted into the phosphoranylidene compounds of the formulae VI and VII, respectively. A suitable basic reagent is, for example, an alkali carbonate or an alkali hydroxide, such as sodium carbonate or potassium hydroxide, an alkali lower alkoxide, for example potassium tert.-butoxide, an alkali metal hydride, for example sodium hydride, a metallated hydrocarbon or amine, for example butyl lithium, phenyl lithium or sodium amide, or a tertiary amine, such as a tri-lower alkylamine or a cyclic base of the amidine type, for example triethylamine or 1,5-diazabicyclo[5.4.0]undec5-ene. The conversion is carried out in the same reaction medium as the subsequent Wittig condensation described above.

In a preferred embodiment of the above process, the starting material used is a compound of the formula VIa or VIIa in which Y is a group of the formula —$P^⊕$ (—$O^⊖$)($OC_2H_5$)$_2$ which in an inert solvent, for example one of the above-mentioned ethers or hydrocarbons, is treated with a strong base for example butyl lithium or sodium hydride, at low temperatures, for example at approximately −80° to −20° C. and subsequently, without isolating the intermediate phosphoranylidene compound, with an oxo or thioxo compound of the formula ($R_1$, $R_2$)C=$Y_4$ (VIb) or

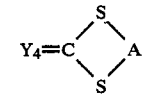

(VIIb)

in which $Y_4$ is oxygen or sulphur.

An alternative procedure, which circumvents the need for the prior generation of the phosphoranylidene compound and which can be carried out under very mild conditions, involves the treatment of the starting material of the formula VIa or VIIa in which, for example, $Y_3$ is a group of the formula —$P^⊕(—O^⊖)(OC_2H_5)_2$ with the suitable oxo or thioxo compounds at room temperature, using a two-phase system consisting of an organic water-immiscible solvent, for example methylene chloride, and an aqueous base solution, for example an aqueous solution of sodium hydroxide, containing an usual phase-transfer catalyst, for example triethylbenzylammonium chloride.

In a further alternative one-pot procedure, a compound of the formula $X_1$—A—$X_1'$(IVa) or $X_2$—A'—$X_2'$(IVb) wherein $X_1$, $X_1'$, $X_2$, $X_2'$, A and A' have the meanings given above (process b) is added to a mixture consisting of an aldehyde of the formula $R_1$—CHO (VIe), carbon disulphide and a tri-lower alkylphosphine in an inert solvent, for example diethyl ether, preferably at reduced temperature, for example at −50° to 0° C., yielding a compound of the formula I in which $R_2$ is hydrogen.

The starting materials of the formulae VI and VII are known or if novel, can be prepared in a manner known per se.

Compounds of the formulae VIa and VIIa can be prepared, for example, by treating the corresponding halide ($Y_3$ represents halogen) with a tri-substituted phosphine of the formula $P(Z_1,Z_2,Z_3)$.

Compounds of the formula VI (or VII) in which $R_6$ (or $R_7$) is a tri-lower alkoxy phosphoranylidene group can be prepared, for example, by reacting a compound of the formula VIb or VIIb with an excess of tri-lower alkoxyphosphine.

Process (e)

A functionally modified hydroxy group $X_4$ and/or $Y_2$ is an etherified or esterified hydroxy group. Etherified hydroxy groups are, for example, phenoxy groups which are unsubstituted or substituted by halogen and/or nitro, for example phenoxy or 4-nitrophenoxy, or especially lower alkoxy, for example methoxy, ethoxy or n-butoxy. Esterified hydroxy is in particular halogen, for example chlorine or bromine, or aliphatic or aromatic sulphonyloxy, for example methanesulphonyloxy, benzenesulphonyloxy or p-toluenesulphonyloxy. Further esterified hydroxy groups are lower alkanoyloxy groups, for example acetoxy, or benzoyloxy. An etherified mercapto group is, for example, lower alkylthio, such as methylthio, ethylthio, isopropylthio or n-butylthio, phenyl-lower alkylthio, such as benzylthio, or phenylthio. A di-substituted amino group is an amino group di-substituted by lower alkyl, for example dimethylamino or diethylamino, lower alkylene, for example pyrrolidin-1-yl or piperidino, or oxa- or thia-lower alkylene, for example morpholino or thio-morpholino.

The reaction is carried out in a conventional manner, for example by reacting the two reaction components in a suitable solvent, such as a lower alkanol, for example methanol, an ether, for example diethyl ether, a hydrocarbon, for example benzene, a halogenated hydrocarbon, for example methylene chloride, dimethyl sulphoxide or water or in mixtures thereof, in the presence of a catalysing agent, for example a catalytic amount of hydrogen chloride, or in particular in the presence of a base, such as an alkali hydroxide, for example potassium hydroxide, an alkali carbonate, for example potassium carbonate, an alkali lower alkoxide, for example sodium ethoxide or potassium tert.-butoxide, or a tertiary amine, for example triethylamine, if necessary while cooling or heating, for example in a temperature range of about $-20°$ to about $+120°$ C., and/or in an inert gas atmosphere, for example in a nitrogen atmosphere.

The starting materials of the formulae VIII and IX are known or, if novel, can be synthesised in a manner known per se.

For example, compounds of the formula VIII in which both $X_4$ and $Y_2$ are functionally modified hydroxy groups and $Y_1$ is a radical $R_2$ can be prepared by treating a compound of the formula $$\begin{array}{c} R_1 \quad X_4 \\ | \quad | \\ R_2-C-C-Y_2 \\ | \quad | \\ Cl \quad H \end{array} \quad \text{(VIIIa)}$$

with a basic agent.

Compounds of the formula VIIIa in which $R_2$ represents hydrogen can further be treated with a basic agent to yield compounds of the formula VIII in which $Y_1$ and $Y_2$ together represent a carbon-carbon bond and $X_4$ is a functionally modified hydroxy group.

Compounds of the formula VIII in which $X_4$ is an etherified mercapto group and $Y_2$ is a di-substituted amino group and $Y_1$ is the group $R_2$ are advantageously prepared in situ, for example, by treating a S-methylsulphonium salt of the formula

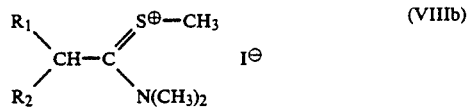

(VIIIb)

with a base, for example with potassium carbonate.

Process (f)

The reaction is carried out in a conventional manner under conditions which cause splitting off ammonia, preferably at elevated temperatures, for example at about 80° to about 200° C., especially at about 130° to about 180° C., preferably in the presence of a catalytic amount of a basic condensation agent, for example pyridine or a tertiary amine, especially an aliphatic tertiary amine, for example triethylamine, tri-n-propylamine or tri-n-butylamine, in an inert solvent having a correspondingly high boiling point, for example an ether, such as diphenyl ether or di-n-butyl ether, or a hydrocarbon, such as toluene, xylene or decalin, or especially without adding a solvent by directly heating the nitrile of the formula X with the dithiol of the formula IX in the presence of the basic condensation agent, if necessary under an inert gas, for example nitrogen.

Process (g)

The condensation is effected in a conventional manner under conditions which cause splitting off carbon dioxide and ammonia, preferably at elevated temperatures, for example at 100° to 250° C., especially at 130° to 170° C., in an inert solvent, for example one of those mentioned above (process f), or preferably without adding a solvent, if necessary under an inert gas atmosphere, for example a nitrogen atmosphere.

The starting materials of the formulae XI and XII are known or, if novel can be prepared in an manner known per se.

The monothiocarbonates of the formula XI can be obtained, for example, by carbonylating a compound of the formula HO—A—SH (XIa) with nickel tetracabonyl in the presence of oxygen or by reacting the compound XIa with phosgene.

Process (h)

An etherified mercapto group $R_8$ is, for example an optionally substituted lower alkylthio radical or an arylthio radical. An optionally substituted lower alkylthio radical $R_8$ represents, for example, lower alkyl or lower alkyl substituted by phenyl and is especially lower alkyl, for example methyl, ethyl, n-propyl, isopropyl, n-butyl, isobutyl or sec.-butyl, or phenyl-lower alkyl, for example benzyl. An arylthio radical is, for example, phenylthio.

An anion $X_5^-$ is the anion, such as the monovalent anion, of an inorganic or organic acid, such as a halide, for example chloride, bromide or iodide, perchlorate, a lower alkyl sulphate, for example methyl sulphate, a substituted or unsubstituted lower alkanesulphonate, for example methanesulphonate, a substituted or unsubstituted benzenesulphonate, for example p-toluenesulphonate, or tetrafluoroborate.

The condensation is carried out in a conventional manner, i.e. in the presence of a suitable base which converts the starting compound of the formula IVc into its anion, such as an alkali metal hydride, for example sodium hydride, an alkali metal hydroxide, for example potassium hydroxide, an alkalimetal lower alkoxide, for example sodium ethoxide or potassium tert.-butoxide, or an amine, for example pyridine, in an inert solvent, such as an ether, for example ethanol or tert.-butanol, dimethylformamide, dimethyl sulphoxide or, if pyridine is used as the base, for example acetic acid. The reaction may be conducted at room temperature or at reduced or elevated temperature, for example at 0° to 80° C. or in the vicinity of the boiling point of the solvent used, if necessary in an inert gas atmosphere, for example in a nitrogen atmosphere.

The starting materials of the formula XIII are known or, if novel, can be prepared in a manner known per se.

The carbenium compounds of the formula XIII can be prepared, for example, by treating a trithiocarbonate of the formula

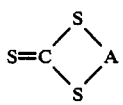

(XIIIa)

with an etherifying agent, for example with methyl iodide or dimethyl sulphate. The anion of the resulting carbenium salt, for example iodide or methyl sulphate, may be replaced by another anion in order to obtain a more stable and crystalline salt, for example by perchlorate. The carbenium salts of the formula XIII can likewise be used without isolation and purification.

Process (i)

A radical Z which is converted by cyclisation into the radical A is, for example, a radical of the formula —A"—X$_6$ wherein X$_6$ is a substituent which can be replaced by nucleophilic substitution and A" is synonymous with A or wherein X$_6$ is a radical that is susceptible to thiol addition reactions and that, after the thiol addition has been performed, together with the radical A" forms a radical A. Thus, in the second instance, A" is, for example, a lower alkylene radical having up to 4 carbon atoms which is substituted in the 1-position by the thio radical, in the ω-position by X$_6$ and which can further be substituted as detailed in the definition of A.

In the starting material of the formula XIV, groups X$_6$ that can be replaced by nucleophilic substitution or that are susceptible to thiol addition reactions are especially those mentioned in the definition of the radicals X$_1$, X$_1'$, X$_2$ and X$_2'$ in process (b).

The cyclisation is carried out in a conventional manner in an inert solvent, such as a lower alkanol, for example, ethanol an ether, for example diethyl ether, dimethylformamide, water or mixtures thereof, if necessary in the presence of a base, such as an alkali hydroxide, for example potassium hydroxide, a metal hydride, for example sodium hydride, an alkali metal lower alkoxide, for example sodium ethoxide or potassium tert.-butoxide, a metal amide, for example lithium amide, sodium amide or lithium diisopropylamide, or a tertiary amine, for example pyridine or triethylamine, at room temperature or at elevated or reduced temperature, for example within a temperature range of from approximately −20° to approximately +100° C., especially at 0° to 50° C., or alternatively in the absence of a solvent, at elevated temperatures, for example at 100° to 150° C., or especially at the boiling point of the starting material under reduced pressure, for example under water-pump vacuum.

The starting compounds of the formula XIV are known or, if novel, can be prepared in a manner known per se, for example by esterifying a dithiocarboxylic acid of the formula

(XIVa)

with an alkylating agent of the formula Z—X$_7$ (XIVb) wherein X is a reactive esterified hydroxy group, for example bromine, in the presence of a base.

Process (j)

The dehydrogenation is carried out in a conventional manner with the use of a dehydrogenating agent at room temperature or at elevated or reduced temperature, for example in a temperature range of from approximately −70° to approximately 200° C., in an inert solvent, such as an ether, for example diethyl ether, diphenyl ether or tetrahydrofuran, a lower alkanol, for example methanol or tert.butanol, a hydrocarbon, for example hexane or xylene, or a halogenated hydrocarbon, for example chlorobenzene, if necessary, in the presence of a base, for example a metallated hydrocarbon, for example butyl lithium, an alkali alkoxide:for example sodium methoxide or potassium tert.-butoxide, or an alkali hydroxide, for example potassium hydroxide, if necessary under pressure in a closed vessel and, if necessary, under an inert gas, for example nitrogen. Suitable dehydrogenating agents are, for example, transition metal catalysts,for example catalysts containing subgroup VIII metals, especially platinium-triphenylphosphine chloride, the catalysts optionally being supported on a suitable carrier, such as carbon, aluminium oxide or silicon dioxide. Further dehydrogenating agents are, for example, quinones, such as p -benzoquinones, for example tetrachloro-p-benzoquinone or 2,3-di -chloro-4,5-dicyano-p-benzoquinone, or phenanthrene-9,10-quinone, N-halogenated sulphonamides, such as N-halogenated aromatic sulphonamides, for example chloramine-T, or organic low-valency sulphur or selenium compounds, such as disulphides, for example diphenyl disulphide, 2,2'-dipyridyl disulphide or 2,2'-dithiobis(benzothiazole), or seleninic acids or derivatives thereof, for example benzeneseleninic anhydride.

Preferred dehydrogenating agents are the disulphides mentioned above which are used at low temperature for example at −70° to −10° C., in tetrahydrofuran or hexane in the presence of a strong base, for example butyl lithium, and in a nitrogen atmosphere. Another preferred dehydrogenating agent is chloramine-T. If this agent is used, the reaction is preferably carried out in two steps. First, the starting material of the formula XV is reacted with chloramine-T in a lower alkanol, for example methanol, in a temperature range of 0° to 20° C., then the resulting S-tosylimino compound of the formula

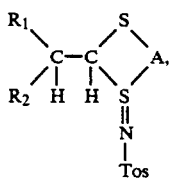

(XVa)

in which Tos represents the p-toluene sulphonyl ("tosyl") group, is treated with a base, such as an alkali hydroxide, for example potassium hydroxide, in a lower alkanol, for example tert.-butanol, at room temperature.

The starting materials of the formula XV can be produced in a manner known per se, for example by treating an aldehyde of the formula

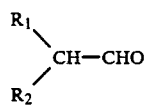

(XVb)

with a dithiol of the formula HS—A—SH (IX).

Process (k)

In a starting compound of the formula XVI an etherified hydroxy group $R_9$ is especially a lower alkoxy group or a phenyl-lower alkoxy group, for example methoxy, ethoxy, n-propoxy, isopropoxy, n-butoxy, isobutoxy, sec.-butoxy or benzyloxy.

In a starting compound of the formula XVII a lower alkyl group $R_{10}$ is, for example, methyl, ethyl, n-propyl, n-butyl or tert.butyl.

The reaction is carried out in a conventional manner in an inert solvent, such as a hydrocarbon, for example hexane, benzene or toluene, an ether, for example diethylether, dioxane or tetrahydrofuran, or a halogenated hydrocarbon, for example methylene chloride or carbon tetrachloride, or in a mixture thereof, advantageously with the exclusion of moisture, under an inert gas, for example argon or nitrogen, and at normal or moderately reduced temperature, for example at $-20°$ C. to $25°$ C.

The starting materials are known or, if novel, can be prepared in a manner known per se.

For example, the compounds of the formula XVII are advantageously prepared in situ, for example by reacting a dithiol of the formula HS—A—SH (IX) with two equivalents of trimethylaluminium.

Process (l)

An optionally substituted hydrocarbylidene radical $R_2'$ is a radical derived from an optionally substituted hydrocarbon radical $R_2$ having at least one hydrogen atom at the α carbon atom, this α carbon atom forming together with the adjacent carbon atom $C(R_1)$- a double bond.

The isomerisation is effected in a conventional manner, for example, by treating the compounds of the formula XVIII with a suitable isomerising agent in an inert solvent, such as a lower alkanol, for example ethanol or tert.-butanol, an ether, for example dimethoxyethane or tetrahydrofuran, an amide, for example dimethylformamide, or acetonitrile, at normal, reduced or elevated temperature, for example in a temperature range of about $-20°$ C. to about $100°$ C., if necessary under an inert gas, for example nitrogen. Suitable isomerising agents are especially inorganic or organic bases, such as an alkali metal hydroxide, for example potassium hydroxide, a tertiary amine, for example triethylamine, pyridine, or, in particular, an alkali metal lower alkoxide, for example sodium ethoxide or potassium tert.-butoxide.

The starting compounds of the formula XVIII are known or, if novel, can be prepared in a manner known per se, for example by treating a compound of the formula

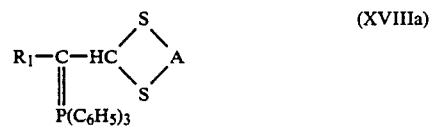

(XVIIIa)

with an oxo compound of the formula $R_2'$=O (XVIIIb).

The compounds of the formula XVIII can also prepared in situ, for example by treating a compound of the formula

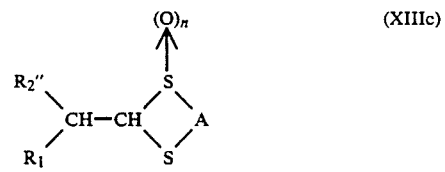

(XIIIc)

wherein $R_2''$ is a hydrocarbon radical $R_2$ in which the α carbon atom is substituted by a nucleofugic group, for example a chlorine atom, with potassium tert.-butoxide in tert.-butanol.

Process (m)

If in a starting compound of the formula XIX $X_8$ represents a sulphur atom, $R_{11}$ is preferably hydrogen, lower alkyl, phenyl, phenyl-lower alkyl or is an amino group optionally substituted by lower alkyl or lower alkylene.

If in a starting material of the formula XIX $X_8$ denotes especially an unsubstituted imino group, $R_{11}$ denotes a mercapto group. If in a starting material of the formula XIX $X_8$ represents an imino group substituted by lower alkyl, $R_{11}$ is especially hydrogen, lower alkyl, phenyl, phenyl-lower alkyl or a mercapto group.

A bivalent alkylating agent capable of introducing the group A is, for example, a halogenated oxo compound of the formula

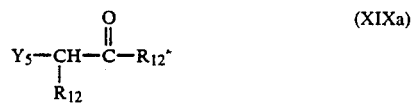

(XIXa)

wherein $R_{12}$ and $R_{12}'$ are hydrogen or are the same or different organic radicals, such as lower alkyl, for example methyl, ethyl, n-propyl or n-butyl, cycloalkyl, for example cyclopentyl or cyclohexyl, phenyl or phenyl-lower alkyl, for example benzyl, and $Y_5$ represents halogen, for example chlorine, bromine or iodine; or an ethylene derivative of the formula

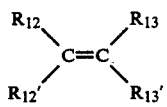
(XIXb)

wherein R₁₃ and R₁₃' for example have the same meanings as the radicals R₁₂ and R₁₂' mentioned above; or a substituted acetylene compound of the formula R₁₄—C≡C-R₁₄' (XIXc) wherein R₁₄ is a substituent activating the triple bond, such as an optionally substituted phenyl group, for example phenyl,p-chlorophenyl or p-methoxyphenyl, a tertiary amino group, for example dimethylamino, diethylamino or pyrrolidin-1-yl, phenyl-lower alkyl, for example benzyl, cyano, carboxy or lower alkoxycarbonyl, for example methoxycarbonyl or ethoxycarbonyl, and R₁₄' is hydrogen, lower alkyl, for example methyl, or has the meaning of R₁₄.

The reaction is conducted in a manner known per se and dependent on the nature of the bivalent alkylating agent.

If an oxo compound of the formula XIXa is chosen as the bivalent alkylating agent, the reaction is carried out in two steps. First the thiono compound of the formula XIX is treated in an inert solvent, such as a ketone, for example acetone, a lower alkanol, for example methanol or ethanol, acetonitrile or dimethylformamide, at normal or moderately reduced or elevated temperature, for example in a temperature range of about 0° to 40° C., with the alkylating agent of the formula XIXa. The resulting intermediate compound of the formula XIXd

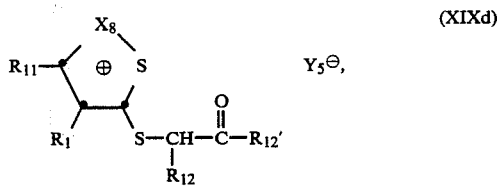
(XIXd)

optionally without being isolated, is then cyclised by treatment with a base, such as pyridine or a tertiary amine, for example triethylamine, and a sulphurizing agent, for example phosphorus pentasulphide, in an inert solvent, such as an ether, for example dimethoxyethane or tetrahydrofuran, an amide, for example dimethylformamide, or dimethyl sulphoxide, acetonitrile or in an excess of the liquid base being used for example pyridine, at normal or elevated temperatures, for example in a temperature range of from about 20° C. to about 120° C., preferably at the boiling point of the solvent.

If the ethylene compound of the formula XIXb is used as the bivalent alkylating agent, a mixture consisting of this agent and the compound of the formula XIX in an inert solvent, such as a hydrocarbon, for example hexane, benzene, toluene or xylene, or a halogenated hydrocarbon, for example methylene chloride, dichloroethane or chlorobenzene, is irradiated with ultraviolet light, for example with a high-pressure mercury lamp, at a temperature not exceeding 50° C., preferably at 0° to 20° C., if necessary under an inert gas, for example nitrogen.

The alkylation with the acetylenic compound of the formula XIXc is carried out in an inert solvent, such as a hydrocarbon, for example benzene, toluene or xylene, a halogenated hydrocarbon, for example methylene chloride or chloroform, an ether, for example dimethoxyethane or dioxane, dimethylformamide or acetonitrile, at normal or elevated temperature, for example in a temperature range of from about 20° to about 130° C., especially in the vicinity of the boiling point of the solvent used.

The starting materials of the formulae XIX, XIXa, XIXb and XIXc are known or, if novel, can be prepared in a manner known per se.

For example, compounds of the formula XIX in which X₈ is a sulphur atom are prepared by reacting a β-ketoester of the formula R₁₁—C(=O)—CH(—R₁)—COOC₂H₅ with phosphorus pentasulphide.

Compounds of the formula XIX wherein X₈ is an imino group optionally substituted by lower alkyl are prepared, for example, by reacting a compound of the formula

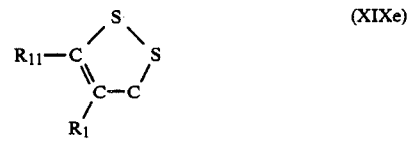
(XIXe)

with bromine and subsequently with ammonia or a lower alkyl amine.

Process (n)

A phosphonium group Z₇ is, for example, a phosphono group esterified twice or, especially, a phosphonio group substituted three times together with an anion neutralising the positively charged phosphorus atom. Suitable phosphono or phosphonio groups Z₇ are those customarily used in Wittig condensation reactions, for example a phosphono group esterifed twice by lower alkyl, for example methyl or ethyl, or phenyl-lower alkyl, for example benzyl, or a phosponio group substituted three times by lower alkyl, for example n-butyl, or, in particular, aryl, for example phenyl. Preferred as group Z₇ is triphenylphosphonio. An anion neutralising the positively charged phosphorus atom of a phosphonio group is especially the anion of a strong organic or inorganic acid, such as a sulphonate, for example benzenesulphonate, p-toluenesulphonate or methanesulphonate, or in particular a halide anion, for example chloride or bromide anion.

A hydrolysing agent is a basic agent, especially a strong inorganic base, such as an alkali metal carbonate, for example sodium carbonate, or in particular an alkali metal hydroxide, for example sodium hydroxide or potassium hydroxide.

The reaction is carried out in a suitable solvent, for example in water or in a solvent mixture containing water and an organic water-miscible solvent, for example a lower alkanol, for example methanol or ethanol, or a lower aliphatic diether, for example dimethoxyethane, especially at elevated temperature, preferably at the boiling point of the solvent or solvent mixture used, and, if necessary, in an inert gas atmosphere, for example in a nitrogen atmosphere.

The starting compounds of the formula XX are known or can be prepared in a manner known per se, for example by treating a phosphonium compound of the formula R₁CH⊖—Z₇ (XXa) wherein, if Z₇ is a phosphono group, the negative charge is neutralised by a conventional cation, for example sodium, with carbon disulphide and reacting the resulting dithiocarboxylate of the formula Z₇—CH(R₁)—CS₂⊖ (XXb) *in the presence of a* basic agent with a dihalide of the formula Y₅—A—Y₅ (XXc) wherein Y₅ is chlorine or bromine.

Process (o)

Agents which favour splitting off nitrogen from a compound of the formula XXI are, for example, ultraviolet irradiation or basic agents.

It is presumed that, when subjected to ultraviolet irradiation, the thiadiazole of the formula XXI is converted into the nitrogen-free di-radical of the formula XXIa which to some extent rearranges to give the thioketene of the formula XXIb. Subsequently, the supposed intermediates of the formulae XXIa and XXIb would combine to yield the compounds of the formula I (Scheme 1; cf. A. Shafiee, I. Lalezari, J. Heterocycl. Chem. 10, 11 (1973)).

Scheme 1

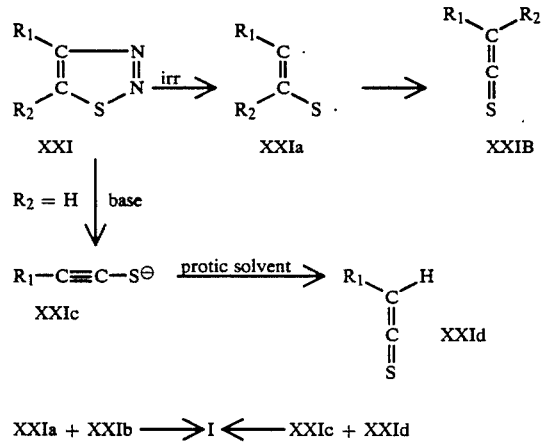

XXIa + XXIb ———>I<——— XXIc + XXId

The conversion of the starting material of the formula XXI into the compound of the formula I by means of a basic agent is assumed to proceed in an analogous manner, via the anion of the formula XXIc (Scheme 1; cf. A. Shafiee, I. Lalezari, supra). Is evident that this route is only operable if R₂ represents hydrogen and a hydrogen-donating solvent, i.e. a protic solvent, is used.

The conversion is carried out in a conventional manner. For example, the starting material of the formula XXI can be irradiated in an inert solvent, such as a lower alkanol, for example methanol or, preferably, in a hydrocarbon, for example benzene or hexane, by means of a suitable ultraviolet lamp, for example a quartz dipping lamp or a medium pressure mercury vapour lamp, at normal or elevated temperature, for example in a temperature range of from about 20° to about 80° C., if necessary under an inert gas, for example nitrogen.

If a basic agent, such as an alkali hydroxide, for example potassium hydroxide, an alkali lower alkoxide, for example sodium methoxide or potassium ethoxide, or a metallated hydrocarbon, for example a lower alkane or benzene metallated by an alkali or alkaline earth metal, such as butyl lithium or phenyl lithium, is used the reaction is carried out in a protic solvent or in a solvent mixture which contains at least one protic component, such as water or a lower alkanol, for example methanol or ethanol, or mixtures thereof, at normal, reduced or elevated temperature, for example in a temperature range of from −20° to +100° C., especially at 20° to 60°, if necessary under an inert gas, for example nitrogen. It is also possible to carry out the reaction in two steps. For example, the starting compound of the formula XXI can be treated with a strong basic agent, for example butyl lithium, in an inert solvent, such as an ether, for example dimethoxyethane or tetrahydrofuran, at low temperature, for example in a temperature range of from about −70° to about −20° C., and the resulting solution containing the metal salt, for example the lithium salt, of the intermediate XXIc can be transferred to the protic solvent, such as one of those mentioned above, at normal or elevated temperature, for example in a temperature range of from about 20° to about 100° C., especially at 20° to 60° C., if necessary under an inert gas, for example nitrogen.

The starting compounds of the formula XXI are known or, if novel, can be prepared in a manner known per se, for example by reacting a semicarbazone of the formula R₁—C(CH₂R₂)=NNHCONH₂ (XXIe) with thionyl chloride.

Process (p)

The reaction of the diazoketone of the formula XXII with carbon disulphide is carried out in a customary manner under conditions which cause splitting off carbon monoxide and nitrogen, for example in an inert solvent, such as an ether, for example, diethyl ether, tetrahydrofuran or dioxane, or, especially, in an excess of carbon disulphide, at normal or slightly elevated temperature, for example in a temperature range of from approximately 20° to approximately 50° C., preferably in the vicinity of the boiling point of carbon disulphide, if necessary under an inert gas, for example nitrogen.

The starting materials of the formula XXII are known or, if novel, can be prepared in a manner known per se, for example by reacting a compound of the formula R₁—CO—CO—R₂ (XXIIa) with tosyl hydrazine and cleaving the resulting hydrazone of the formula R₁—C(=O)—C(=N—NH—Tos)—R₂ (XXIIb) in which Tos denotes the tosyl group, with a basic agent.

Process (q)

A desulphurizing agent is, for example, a strong base, such as a metallated hydrocarbon, for example a lower alkane or benzene metallated by an alkali or alkaline earth metal, for example butyl lithium or phenyl lithium, or a metallated secondary amine, such as a metallated di-lower alkyl amine, for example lithium diisopropylamine, or a trivalent phosphorus compound, such as a phosphite, such as a tri-lower alkyl phosphite, for example triethylphosphite, or a tri-substituted phosphine, such as a trilower alkyl- or triarylphosphine, for example tri-n-butylphosphine, or a metal which is capable of desulphurizing under mild conditions, for example copper.

The desulphurization is carried out in a conventional manner, for example in an inert solvent, such as an aliphatic or aromatic hydrocarbon, for example hexane, benzene or xylene, an aliphatic or aromatic ether, for example diethyl ether, di-n-butyl ether or diphenyl ether, or a halogenated hydrocarbon, for example chloroform, at normal, reduced or elevated temperature, for example, if a strong base is used as the desulphurizing agent, in a temperature range of from −60° to 20° C. or, if a metal or trivalent phosphorus compound is used, in a temperature range of from 20° to 150° C., especially at the boiling point of the solvent used, if necessary in an inert gas atmosphere, for example in a nitrogen atmosphere.

The starting material of the formula XXIII is known or if novel, can be prepared in a manner known per se, for example by treating a diazo compound of the formula R$_1$—C(=N$_2$)—R$_2$ (XXIIIa) with a trithiocarbonate of the formula

(XXIIIb)

In the starting compounds of the formulae II–XXIII, functional groups present, especially carboxy, amino and hydroxy groups, and also sulpho groups, are optionally protected by conventional protecting groups that are customary in preparative organic chemistry. Protected carboxy, amino, hydroxy and sulpho groups are those that can be converted under mild conditions into free carboxy, amino, hydroxy and sulpho groups without the molecular framework being destroyed or other undesired side reactions taking place.

The purpose of introducing protecting groups is to protect the functional groups from undesired reactions with reaction components and thus prevent their being removed or converted into a derivative. On the other hand, reaction components can be consumed or bonded in an undesired manner by reaction with an unprotected functional group and are then no longer available for the actual reaction. The choice of protecting groups for a particular reaction depends on the nature of the functional group to be protected (carboxy group, amino group etc.), the structure and stability of the molecule of which the substituent is the functional group, and the reaction conditions.

Protecting groups that meet these conditions and their introduction and removal are known and are described, for example, in J. F. W. McOmie, "Protective Groups in Organic Chemistry", Plenum Press, London, New York 1973, T. W. Greene, "Protective Groups in Organic Synthesis", Wiley, New York 1981, and also in "The Peptides", Vol. I, Schroeder and Luebke, Academic Press, London, New York 1965, as well as in Houben-Weyl, "Methoden der Organischen Chemie", Vol. 15/1, Georg Thieme Verlag, Stuttgart, 1974.

Thus, carboxy groups are protected, for example, in esterified form, it being possible for such ester groupings to be removed easily under mild conditions, especially alkaline conditions. Such esterified carboxy groups contain as esterifying groups especially lower alkyl groups branched in the 1-position or suitably substituted in the 1- or 2-position. Preferred carboxy groups present in esterified form are, inter alia, lower alkoxycarbonyl, for example methoxycarbonyl, ethoxycarbonyl or isopropoxycarbonyl; arylmethoxycarbonyl having from 1 to 3 aryl radicals or a heteroaryl radical, these aryl moieties representing phenyl radicals optionally mono- or poly-substituted, for example by lower alkyl, such as tert.-lower alkyl, for example tert.-butyl, or by halogen, for example chlorine, and/or nitro, such as benzyloxycarbonyl optionally substituted, for example in the manner mentioned above, for example 4-nitrobenzyloxycarbonyl, diphenylmethoxycarbonyl optionally substituted, for example in the manner mentioned above, for example diphenylmethoxycarbonyl, or triphenylmethoxycarbonyl, or picolyloxycarbonyl radicals optionally substituted, for example in the manner mentioned above, for example 4-picolyloxycarbonyl, 1-lower alkoxycarbonyl, such as methoxymethoxycarbonyl, 1-methoxyethoxycarbonyl or ethoxymethoxycarbonyl; aroylmethoxycarbonyl in which the aroyl group represents benzoyl optionally substituted, for example, by halogen, such as bromine, for example phenacyloxycarbonyl; halo-lower alkoxycarbonyl, such as 2-halo-lower alkoxycarbonyl, for example 2,2,2-trichloroethoxycarbonyl, 2-bromoethoxycarbonyl or 2-iodoethoxycarbonyl; or ω-halo-lower alkoxycarbonyl in which lower alkoxy contains from 4 to 7 carbon atoms, for example 4-chlorobutoxycarbonyl; phthalimidomethoxycarbonyl or 2-(trisubstituted silyl)-ethoxycarbonyl in which the substituents, independently of each other, represent an aliphatic, araliphatic, cycloaliphatic or aromatic hydrocarbon radical having, for example, up to 15 carbon atoms that is unsubstituted or substituted, for example, by lower alkyl, lower alkoxy, aryl, halogen and/or nitro, such as corresponding optionally substituted lower alkyl, phenyl-lower alkyl, cycloalkyl or phenyl, for example 2-tri-lower alkylsilylethoxycarbonyl, such as 2-trimethylsilylethoxycarbonyl or 2-(di-n-butyl-methyl-silyl)-ethoxycarbonyl, or 2-triarylsilylethoxycarbonyl, such as 2-triphenylsilylethoxycarbonyl.

Other protected carboxy groups present in esterified form are corresponding silyloxycarbonyl groups, especially organic silyloxycarbonyl groups, and also corresponding stannyloxycarbonyl groups. In these, the silicon or tin atom, respectively, contains preferably lower alkyl, especially methyl or ethyl, also lower alkoxy, for example methoxy, as substituents. Suitable silyl and stannyl protecting groups are especially tri-lower alkylsilyl, especially trimethylsilyl or dimethyl-tert.-butylsilyl, or correspondingly substituted stannyl groups, for example tri-n-butylstannyl.

A protected amino group may be present, for example, in the form of a readily cleavable acylamino, silylamino or stannylamino group.

In a corresponding acylamino group acyl is, for example, the acyl radical of an organic carboxylic acid having, for example, up to 18 carbon atoms, especially of an alkanecarboxylic acid optionally substituted, for example, by halogen, cyano or aryl, or of a carbonic acid semi-ester. Such acyl groups are, for example, lower alkanoyl, such as formyl, acetyl or propionyl, halo-lower alkanoyl, such as 2-haloacetyl, especially 2-chloro-, 2-bromo-, 2-iodo-, 2,2,2-trifluoro- or 2,2,2-trichloroacetyl, phenoxycarbonyl, lower alkoxycarbonyl, for example methoxycarbonyl, isobutoxycarbonyl or tert.-butoxycarbonyl, aryl-lower alkoxycarbonyl, for example benzyloxycarbonyl or diphenylmethoxycarbonyl each optionally substituted by nitro, or lower alkoxycarbonyl optionally branched in the 1-position and/or substituted in the 1- or 2-position by organic silyl, sulphonyl, phosphonio, cyano or aryl, such as 2-trilower alkylsilylethoxycarbonyl, for example 2-trimethylsilylethoxycarbonyl, 2-sulphonylethoxycarbonyl, for example 2-methylsulphonylethoxycarbonyl, 2-phosphonioethoxycarbonyl, for example 2-trimethylphosphonioethoxycarbonyl, 2-cyano-lower alkoxycarbonyl, for example 1,1-dimethyl-2-cyanoethoxycarbonyl, or fluorenylmethoxycarbonyl. A silylamino or stannylamino group is especially an organic silylamino or stannylamino group in which the silicon or tin atom, respectively, preferably contains lower alkyl, especially methyl or ethyl, also lower alkoxy, for example methoxy, as substituent(s). Corresponding silyl or stannyl groups are especially tri-lower alkylsilyl, especially trimethylsilyl, further dimethyl-tert.-butylsilyl, or correspondingly substituted stannyl, for example tri-n-butylstannyl. Hydroxy-protecting groups that can be removed under mild conditions are, for example, acyl radicals, such as lower alkanoyl optionally substituted by halogen or etherified hydroxy, such as lower alkanoyl, for example formyl, acetyl or pivaloyl, halo-lower alkanoyl, for example chloroacetyl, dichloroacetyl, trichloroacetyl or trifluoroacetyl, lower alkoxy-lower alkanoyl, for example methoxyacetyl, aryl-lower alkoxy-lower alkanoyl, for example triphenylmethoxyacetyl, or aryloxy-lower alkanoyl, for example phenoxyacetyl, benzoyl, lower alkoxycarbonyl, for example methoxycarbonyl, ethoxycarbonyl or tert.-butoxycarbonyl, aryl-lower alkoxycarbonyl, for example benzyloxycarbonyl or diphenylmethoxycarbonyl each optionally substituted by nitro, or organic silyl, such as one of the silyl groups mentioned in connection with a protected carboxy or amino group, especially tri-lower alkylsilyl groups.

A protected sulpho group is especially an esterified sulpho group, such as a sulpho group esterified by an aliphatic, cycloaliphatic, cycloaliphatic-aliphatic, aromatic or araliphatic alcohol, for example a lower alkanol, or by a silyl or stannyl radical, such as tri-lower alkylsilyl. In a sulpho group the hydroxy group may be protected, for example, in the same manner as the hydroxy group in an esterified carboxy group.

In a resulting compound of the formula (I) in which one or more functional groups are protected, these, for example protected carboxy, amino, hydroxy and/or sulpho groups, may be freed in a manner known per se by means of solvolysis, such as hydrolysis, or alcoholysis. Thus, an acyl radical used as an amino- or hydroxy-protecting group can be removed in a manner known per se, especially by alcoholysis, or also by hydrolysis. Removal by alcoholysis of an acyl radical can be carried out, for example, in the presence of a strongly basic agent. In this process there is used especially a lower alkanol, for example ethanol or n-butanol and, as strong base, an alkali metal alkoxide, for example sodium or potassium lower alkoxide, for example sodium or potassium ethoxide or n-butoxide, or an alkali metal hydroxide, for example sodium or potassium hydroxide. The protecting groups used within the scope of the present invention can also be removed by hydrolysis. The hydrolysis can be carried out especially in the presence of a strong base, such as one of those mentioned above or a nitrogen base, such as a tri-lower alkylamine, for example ethyldiisopropylamine, pyridine or a quaternary ammonium compound, for example benzyltrimethylammonium hydroxide. Lower alkoxycarbonyl groups used as amino-protecting groups, such as ethoxycarbonyl, can also be removed under mild conditions by acidolysis, for example by treatment with trifluoroacetic acid. Furthermore, a 2-substituted silylethoxycarbonyl group used as amino or carboxy-protecting group can also be removed by treatment with a salt of hydrofluoric acid that yields the fluoride anion, such as an alkali metal fluoride, for example sodium fluoride, in the presence of a macrocyclic polyether, or with a fluoride of an organic quaternary base, such as tetra-n-butylammonium fluoride. A functional group protected by an organic silyl or stannyl group, such as tri-lower alkyl-silyl or -stannyl, can be freed in customary manner by solvolysis, for example by treatment with water or an alcohol, such as lower alkanol, for example methanol.

The compounds of the formula (I) obtainable according to the invention can be converted into different compounds of the formula (I) in a manner known per se.

For example, in compounds of the formula (I) in which $R_1$ and/or $R_2$ represent an aryl radical substituted by hydroxy, hydroxy may be etherified in customary manner. The reaction to form the corresponding lower alkyl-aryl ethers is carried out, for example, in the presence of bases, such as alkali metal hydroxides or carbonates, for example sodium hydroxide or potassium carbonate, by means of di-lower alkyl sulphates or lower alkyl halides or in the presence of a dehydrating agent, for example dicyclohexylcarbodiimide, by means of lower alkanols.

In compounds of the formula I in which an aliphatically or cycloaliphatically bonded hydroxy group is present, for example as substituent of the radical $R_1$, $R_2$ or A, this hydroxy group may be etherified in customary manner. Suitable etherifying agents are e.g. diazo compounds, such as unsubstituted or substituted diazo-lower alkanes, for example diazomethane, diazoethane, diazo-n-butane or diazoacetic acid esters. These reagents are employed in the presence of a suitable inert solvent, such as an aliphatic, cycloaliphatic or aromatic hydrocarbon. Further suitable etherifying agents are esters of corresponding alcohols, especially those with strong inorganic or organic acids, such as mineral acids, e.g. hydrohalic acids, such as hydrochloric acid, hydrobromic acid or hydroiodic acid, and also sulphuric acid, or halosulphuric acids, for example fluorosulphuric acid, or strong organic sulphonic acids, such as lower alkanesulphonic acids which are unsubstituted or substituted e.g. by lower alkyl, such as methyl, by halogen, such as bromine, and/or by nitro, for example methanesulphonic acid, trifluoromethanesulphonic acid or p-toluenesulphonic acid. Such esters are, inter alia, optionally substituted lower alkyl, lower alkenyl or aryl-lower alkyl halides, for examples methyl iodide, allyl bromide, benzyl bromide or ethyl bromoacetate, sulphates, such as dimethyl sulphate, also fluorosulphonates, for example methyl fluorosulphonate, or unsubstituted or halogen-substituted methanesulphonates, for examples trifluormethanesulphonate. They are usually used in the presence of an inert solvent, such as an unsubstituted or halogenated, such as chlorinated, aliphatic, cycloaliphatic or aromatic hydrocarbon. In addition, it is preferred to use suitable condensing agents, such as alkali metal carbonates or bicarbonates, for example sodium or potassium carbonate or sodium or potassium bicarbonate (usually together with a sulfate), or organic bases, such as sterically hindered tri-lower alkylamines, for example N,N-diisopropyl-N-ethylamine (preferably together with fluorosulphonic acid lower alkyl esters or unsubstituted or halogen-substituted methanesulphonic acid lower alkyl esters). The above-described etherification reaction can be considerably accelerated by phase-transfer catalysis [see Dehmlow, Angewandte Chemie, vol. 86, page 187 (1974)]. As phase-transfer catalysts there may be used quaternary phosphonium salts and especially quaternary ammonium salts, such as unsubstituted or substituted tetraalkylammonium halides, for example tetrabutylammonium chloride, bromide or iodide, or also benzyltriethylammonium chloride, in catalytic or up to equimolar amounts. As the organic phase there can be used any one of the solvents that is not miscible with water, for example one of the unsubstituted or halogenated, such as chlorinated, lower aliphatic, cycloaliphatic or aromatic hydrocarbons. Where compounds that are sensitive to bases are used, the alkali metal carbonates or bicarbonates, for example potassium or sodium carbonate or potassium or sodium bicarbonate, alkali metal phosphates, for example potassium phosphate, and alkali metal hydroxides, for example sodium hydroxide, which are suitable as condensing agents, can be added to the reaction mixture titrimetrically, for example by means of an automatictitrating apparatus such that, during etherification, the pH remains in the range from about 7 to 8.5. Further etherifying agents are suitable acetal compounds, e.g. gem-di-lower alkoxy-lower alkanes,such as 2,2-dimethoxypropane, which are used in the presence of strong organic sulphonic acids such as p-toluenesulphonic acid and of a suitable solvent such as a di-lower alkylsuphoxide or lower alkylenesulphoxide or suitable orthoesters, e.g. tri-lower alkyl esters of orthoformic acid, e.g. triethyl orthoformate, which are used in the presence of a strong mineral acid, e.g. sulphuric acid, or a strong organic sulphonic acid:such as p-toluenesulphonic acid, and of a suitable solvent such as an ether.

In compounds of the formula (I), an amino or lower alkylamino group contained in a radical $R_1$, $R_2$ or A can be converted into a di-lower alkylamino group, for example, by reaction with a reactive lower alkyl ester in the presence of a basic condensation agent. Reactive lower alkyl esters are, for example, lower alkyl halides, such as lower alkyl chlorides, bromides or iodides, lower alkyl sulphonates, for example lower alkyl-loweralkanesulphonates, such as lower alkyl methanesulphonates or ethanesulphonates, lower alkyl benzenesulphonates, such as benzenesulphonates, 4-toluenesulphonates or 4-bromobenzenesulphonates, or lower alkylfluorosulphonates or di-lower alkyl sulphates. Basic condensation agents are, for example, hydroxides or carbonates of an alkali or alkaline earth metal, for example sodium, potassium or calcium hydroxide, sodium or potassium carbonate, or tertiary organic nitrogen bases, such as tri-lower alkylamines, for example triethylamine or diisopropylethylamine, or heteroaromatic nitrogen bases, for example pyridine. In an analogous manner amino groups in radicals $R_1$, $R_2$ or A can be converted into lower alkyleneamino groups by reaction with lower alkylene dihalides or disulphonates, for example 1,3-dibromopropane or 1,4-dibromobutane.

Compounds of the formula (I) in which $R_1$ represents aryl and $R_2$ represents hydrogen can be converted by reaction with isocyanates, such as lower alkyl isocyanates or optionally substituted phenyl isocyanates, or ketenes, such as di-lower alkyl ketenesor diphenyl ketene, into compounds of the formula (I) in which $R_2$ represents amidated carboxy or di-lower alkyl- or diphenylacetyl. Compounds of the formula (I) in which n is 0 can be converted into compounds of the formula (I) in which n is 1 by means of oxidising agents. Suitable oxidising agents are, for example, inorganic peracids, for example periodic or persulphuric acid, organic peracids, for example performic acid, peracetic acid, trifluoroperacetic acid,permaleic acid, perbenzoic acid, 3-chloroperbenzoic acid, monoperphthalic acid, 4-toluenepersulphonic acid or oxidising inorganic salts, for example sodium periodate, it being possible for said acids also to be produced in situ, for example from the corresponding carboxylic acid and hydrogen peroxide. Conversely, compounds of the formula (I) in which n is 1 can be converted into compounds of the formula (I) in which n is 0 by treatment with a reducing agent. There come into consideration as reducing agents, for example, reducing tin, iron, copper or manganese cations, which are used in the form of corresponding compounds or complexes of inorganic or organic nature, for example in the form of tin(II) chloride, fluoride, acetate or formate, iron (II) chloride, sulphate, oxalate or succinate, copper (I) chloride, benzoate or oxide, or manganese (II) chloride, sulphate, acetate or oxide, or in the form of complexes, for example with ethylenediaminetetraacetic acid or nitrolotriacetic acid; reducing dithionite, iodide or iron (II) cyanide anions, which are used in the form of corresponding inorganic or organic salts, such as alkali metal, for example sodium or potassium, dithionite, sodium or potassium iodide or sodium or potassium-iron(II) cyanide; reducing trivalent inorganic or organic phosphorus compounds, such as phosphines, also esters, amides and halides of phosphonous, phosphinous or phosphorous acids, and phosphorus-sulphur compounds corresponding to these phosphorus-oxygen compounds, wherein organic radicals are especially aliphatic, aromatic or araliphatic radicals, for example optionally substituted lower alkyl, phenyl or phenyllower alkyl, such as, for example, triphenylphosphine, tri-n-butylphosphine, diphenylphosphonous acid methyl ester, diphenylchlorophosphine, phenyldichlorophosphine, benzenephosphonous acid dimethyl ester, butanephosphonous acid methyl ester, phosphoric acid triphenyl ester, phosphorous acid trimethyl ester, phosphorus trichloride, phosphorus tribromide etc.; reducing halosilane compounds that contain at least one hydrogen atom bonded to the silicon atom and that may contain, apart from halogen, such as chlorine, bromine or iodine, also organic radicals, such as aliphatic or aromatic groups, for example optionally substituted lower alkyl or phenyl, such as chlorosilane, bromosilane, di- or tri-chlorosilane, di- or tri-bromosilane, diphenylchlorosilane or dimethylchlorosilane; and reducing quaternary chloromethylene iminium salts, especially the chloride or bromides, in which the iminium group is substituted by a bivalent or two monovalent organic radicals, such as optionally substituted lower alkylene or lower alkyl, such as N-chloromethylene-N,N-diethyliminium chloride or N-chloromethylene pyrrolidinium chloride.

Compounds of the formula (I) in which at least one of the radicals $R_1$, $R_2$ and A is substituted by esterified hydroxy can be obtained by treating a compound of the formula (I) in which at least one of the radicals $R_1$, $R_2$ and A is substituted by hydroxy with an acylating agent introducing the desired acyl radical. Such agent are, for example, optionally substituted lower alkanecarboxylic acids, optionally substituted benzoic acids or reactive derivatives thereof, such as anhydrides or acid halides, for example acid chlorides or bromides, or hydrohalic acids, especially in the form of reactive esters, for example thionylchloride and phosphorous tribromide. The reactions can be carried out optionally in the presence of condensation agents, when reacting with optionally substituted lower alkanecarboxylic acids, for example, in the presence of carbodiimide compounds, such as dicyclohexyl carbodiimide, or diimidazolylcarbonyl, or when using acid derivatives, for example acid halides, for example in the presence of a basic agent, for example a tri-lower alkylamine, such as triethylamine, or a heterocyclic base, for example pyridine. Conversely, compounds of the formula (I) in which at least one of the radicals $R_1$, $R_2$ and A is substituted by esterified hydroxy can be converted into compounds of the formula (I) in which at least one of the radicals $R_1$, $R_2$ and A is substituted by hydroxy. The conversion to hydroxy is carried out, for example, by alcoholysis with a lower alkanol, for example methanol or ethanol, or preferably by hydrolysis, such as base-catalysed hydrolysis, for example in the presence of sodium hydroxide.

Furthermore, compounds of the formula (I) in which the radical A represents lower alkylene substituted by a nucleofugic leaving group can be converted into compounds of the formula (I) in which the radical A is lower alkenylene. Nucleofugic leaving groups are, for example, esterified hydroxy, such as hydroxy esterified by hydrohalic acids, lower alkanecarboxylic acids, haloalkanecarboxylic acids or optionally substituted benzoic acids, such as halogen, for example chlorine or bromine, lower alkanoyloxy, for example acetoxy, halo-lower alkanoyloxy, for example trifluoroacetoxy, or optionally substituted benzoyl, for example benzoyl or 2,4-dinitrobenzoyl, etherified hydroxy, such as lower alkoxy, for example methoxy or ethoxy, optionally substituted phenyl-lower alkoxy, for example benzyloxy, or optionally substituted phenoxy, for example phenoxy, or etherified mercapto, such as lower alkylthio, for example methylthio, phenylthio or phenyl-lower alkylthio, for example benzylthio. The conversion, in which the nucleofugic leaving group is removed together with a hydrogen atom in the $\beta$-position, is carried out advantageously in the presence of a base, such as an alkali metal or alkaline earth metal hydroxide, for example sodium or potassium hydroxide, an alkali metal or alkaline earth metal carbonate, for example sodium or potassium carbonate, an alkali metal lower alkoxide, for example potassium tert.-butoxide or potassium tert.-pentoxide, an amine, especially a sterically hindered secondary amine, for example dicyclohexylamine, an aliphatic tertiary amine such as a tri-lower alkylamine, for example diisopropylethylamine or triethylamine, a bicyclic tertiary amine, for example 1,5-diazabicyclo[5.4.0]undec-5-ene, or an aromatic amine, for example pyridine.

Compounds of the formula (I) in which $R_2$ represents carboxy or in which at least one of the radicals $R_1$, $R_2$ and A contain carboxy as substituent, can be obtained from corresponding compounds in which $R_2$ represents functionally modified carboxy or thiocarboxy or $R_1$, $R_2$ and/or A contain functionally modified carboxy as substituent, by freeing the carboxy group(s). The carboxy group(s) can be freed in a manner known per se, especially by hydrolysis. Functionally modified carboxy groups suitable for hydrolysis are, for example, esterified carboxy, such as alkoxycarbonyl, amidated carboxy, such as optionally substituted carbamoyl, and also cyano. Functionally modified thiocarboxy is, for example, optionally substituted thiocarbamoyl. The hydrolysis is carried out preferably in an aqueous or aqueous-organic basic medium, such as in an aqueous or aqueous-lower alkanolic alkali hydroxide solution or also alkali carbonate solution.

Compounds of the formula (I) in which $R_2$ represents functionally modified carboxy or in which at least one of the radicals $R_1$, $R_2$ and A contains this as substituent can be obtained from corresponding compounds in which $R_1$, $R_2$ and/or A represent or contain free or differently functionally modified carboxy in a manner known per se by conversion of the latter group. Functionally modified carboxy is, for example, esterified carboxy, especially lower alkoxycarbonyl, or amidated carboxy, especially optionally substituted carbamoyl. The conversion of carboxy or reactive functional derivatives thereof, for example anhydrides, especially mixed anhydrides, such as those with hydrohalic acids or with monoesters of carbonic acid, further, activated esters, for example cyanomethyl ester or 4-nitrobenzyl ester, as well as also lower alkyl esters, into functionally modified carboxy is carried out, for example, with hydroxy compounds, such as lower alkanols, or with ammonia or primary or secondary amines. It is, however, also possible to react salts, especially alkali metal or alkaline earth metal salts, of free carboxylic acids with reactive esters of hydroxy compounds, for example of lower alkanols, such as hydrohalic acid esters or esters with organic sulphonic acids, for example lower alkanesulphonic acid or arenesulphonic acid esters, such as methanesulphonic acid or 4-toluenesulphonic acid esters, or to react free carboxylic acids also with diazo-lower alkanes to form lower alkyl esters, or with isocyanates to form N-mono-substituted amides. Further, it is also possible to convert nitriles in a manner known per se into N-unsubstituted amides or into esters, especially lower alkyl esters. The reaction of free carboxylic acids with hydroxy compounds is advantageously carried out in the presence of a water-binding condensation agent, for example carbodiimides substituted by hydrocarbon radicals, such as N,N'-dicyclohexylcarbodiimide. Halides and other mixed anhydrides are reacted, for example, in the presence of acid-binding agents, for example organic, especially tertiary, nitrogen bases, such as, for example, triethylamine, ethyldiisopropylamine or pyridine, or also inorganic bases, for example alkali metal or alkaline earth metal hydroxides or carbonates, such as sodium, potassium or calcium hydroxides or carbonates. The reaction of free carboxylic acids with ammonia or primary or secondary amines is carried out, for example, in the presence of the above-mentioned water-binding agents. It is, however, also possible to convert the ammonium salts formed from the free carboxylic acid and ammonia or amines into amides by heating in an inert solvent and removing by distillation, optionally azeotropic distillation, the water freed during the reaction. Salts of compounds of the formula (I) with salt-forming groups can be produced in a manner known per se. For example, salts of compounds of the formula (I) with acidic groups can be formed, for example, by treatment with metal compounds, such as alkali metal salts of suitable organic carboxylic acids or with inorganic alkali or alkaline earth metal salts, ammonia or a suitable organic amine, for which preferably stoechiometric amounts or only a small excess of the salt-forming agent are used. Acid addition salts of compounds of the formula (I) are obtained in customary manner, for example by treatment with an acid or a suitable anion exchange reagent. Inner salts of compounds of the formula (I) that contain, for example, a free carboxy group, can be formed, for example, by neutralisation of salts, such as acid addition salts, to the isoelectric point, for example with weak bases, or by treatment with liquid ion exchangers.

Salts can be converted into the free compounds in customary manner, metal and ammonium salts, for example, by treatment with suitable acids, and acid addition salts, for example, by treatment with a suitable basic agent.

Mixtures of isomers can be separated into the individual isomers in a manner known per se, for example by fractional crystallisation, chromatography etc.

The above-mentioned reactions are carried out according to methods known per se, in the presence or absence of diluents, preferably in diluents that are inert towards the reagents and dissolve these, catalysts, condensation or neutralising agents and/or in an inert atmosphere, while cooling, at room temperature or at elevated temperature, for example at the boiling point of the solvent used, at normal or elevated pressure.

The compounds of the formula (I), including their salts, can also be obtained in the form of their hydrates or can include the solvent used for their crystallisation.

Owing to the close relationship between the novel compounds in free form and in the form of their salts, hereinbefore and hereinafter there is to be understood by the free compounds or their salts optionally also the corresponding salts or free compounds, where appropriate with regard to meaning and purpose.

The invention relates also to those forms of the process in which a compound obtainable as intermediate at any stage of the process is used as starting material and the remaining process steps are carried out, or a starting material is formed under the reaction conditions or is used in the form of a derivative, optionally a salt.

There are used in the process of the present invention preferably those starting materials which result in the compounds described at the beginning as being especially valuable. The present invention relates also to novel starting materials and to processes for their manufacture.

The pharmaceutical preparations according to the invention contain at least one compound of the general formula I or a salt thereof as the active ingredient together with a customary pharmaceutical carrier. The type of carrier depends largely on the field of use. The pharmaceutical compositions according to the invention which contain, as active ingredients, compounds of the formula I can be administered orally or parenterally.

The dosage of active ingredient depends on the species of warm-blooded animal, the age and individual condition, and on the method of administration. In the case of oral administration, the daily dosage recommended for a warm-blooded animal is in the range from 0.1 to 250 mg, preferably from 0.5 to 50 mg, per kilogram body weight. In the case of parenteral administration, the daily dosage recommended for a warm-blooded animal is in the range from 0.01 to 100 mg, preferably from 0.1 to 25 mg, per kilogram body weight. If necessary, the daily dosage may be divided into 3 or 4 equal doses.

The new pharmaceutical preparations contain, for example, from approximately 1% to approximately 95%, preferably from approximately 1% to approximately 50%, of the active ingredient. Pharmaceutical preparations of the invention are, for example, those in unit dosage forms, such as dragees, tablets, capsules or ampoules.

The pharmaceutical preparations according to the present invention are manufactured in a manner known per se, for example by means of conventional mixing, granulating, confectioning, solubilising or lyophilising processes.

Thus, pharmaceutical preparations for oral use can be obtained by combining the active ingredient with solid carriers, optionally granulating a resulting mixture, and processing the mixture or granulate, if desired or necessary after the addition of suitable adjuncts, to form tablets or dragee cores. Suitable carriers are especially fillers, such as sugars, for example lactose, saccharose, mannitol or sorbitol, cellulose preparations and/or calcium phosphates, for example tricalcium phosphate or calcium hydrogen phosphate, also binders, such as starch pastes, gelatin, tragacanth, methylcellulose and/or polyvirylpyrrolidone, and/or, if desired, disintegrating agents, such as the above-mentioned starches, furthermore carboxymethyl starcles, transversely crosslinked polyvinylpyrrolidone, agar, alginic acid or a salt thereof, such as sodium alginate. Adjuncts are especially flow regulators and lubricants, for example silica, talc, stearic acid or salts thereof, such as magnesium or calcium stearate, and/or polyethylene glycol. Dragee cores are given suitable coatings, optionally resistant to gastric juice, there being used inter alia concentrated sugar solutions which optionally contain gum arabic, talc, polyvinylpyrrolidone, polyethylene glycol and/or titanium dioxide, lacquer solutions in suitable organic solvents or mixtures of solvents, or, for the manufacture of coatings resistant to gastric juice, solutions of suitable cellulose preparations, such as acetyl cellulose phthalate, or hydroxypropylmethylcellulose phthalate. Colourants or pigments, for example to identify the active ingredient or characterise different doses of active ingredient, may be added to the tablets or dragee coatings.

Further pharmaceutical preparations for oral administration are push-fit capsules made of gelatin and also soft sealed capsules made from gelatin and plasticiser, such as glycerin or sorbitol. The push-fit capsules can contain the active ingredient in the form of granules, for example in admixture with fillers, such as lactose, binders, such as starches, and/or lubricants, such as talc or magnesium stearate, and optionally stabilisers. In soft capsules, the active ingredient is preferably dissolved or suspended in suitable liquids, such as fatty oils, paraffin oil or liquid polyethylene glycols, to which stabilisers may optionally also be added.

For parenteral administration there are especially suitable aqueous solutions of an active ingredient in water-soluble form, for example a water-soluble salt, also suspensions of the active ingredient, such as corresponding oily injection suspensions, using suitable lipophilic solvents or vehicles, such as fatty oils, for example sesame oil, or synthetic fatty acid esters, for example ethyl oleate or triglycerides, or aqueous injection suspensions, which contain substances that increase viscosity, for example sodium carboxymethylcellulose, sorbitol and/or dextran and optionally also stabilisers.

The following Examples serve to illustrate the present invention but should not be construed as a limitation thereof. Temperatures are given in degrees Centigrade.

EXAMPLE 1

There is added to a solution of 2-trimethylsilyl-1,3-dithiane (16.2 g) in dry tetrahydrofuran (170 ml) at $-65°$ a 1.9M solution of n-butyllithium in hexane (45 ml). The reaction mixture is progressively warmed to 0° in the course of 3½ hours and cooled to $-65°$. A solution of 4-dimethylamino-benzophenone (19.2 g) in dry tetrahydrofuran (100 ml) is than slowly added. The reaction mixture is progressively warmed to room temperature overnight and poured into a mixture of water (1000 ml) and dichloromethane (200 ml). After separation of the layers, the aqueous solution is extracted with dichloromethane (3×200 ml). The combined organic solutions are washed with water (100 ml) and dried over magnesium sulphate. The solvents are evaporated in vacuo and the residue is recrystallised from ethyl acetate. The product is dried in vacuo to constant weight to yield (4-dimethylaminophenyl)(1,3-dithian-2-ylidene)-phenylmethane, m.p. 172°-174°.

EXAMPLE 2 as Example 1, but using 4,4'-difluorobenzophenone (18.4 g) instead of 4-dimethylaminobenzophenone. After recrystallisation from 1-propanol and drying in vacuo to constant weight, (1,3-dithian-2-ylidene)-bis-(4-fluorophenyl)-methane is obtained, m.p. 169°-171°.

EXAMPLE 3

As Example 1, but using α,α,α-trifluoroacetophenone (14.7 g, instead of 4-dimethylaminobenzophenone. After recrystallisation twice from n-hexane and drying in vacuo to constant weight, 1-(1,3-dithian-2-ylidene)-2,2,2-trifluoro-1-phenyl-ethane is obtained, m.p. 87°-88°.

EXAMPLE 4

A 1.3M solution of n-butyllithium in hexane (28 ml) is added at −78° to a solution of 2-diethoxyphosphoryl-1,3-dithiolane (8.1 g) in dry tetrahydrofuran (70 ml). The mixture is stirred for one hour at −78° and 4-fluoroacetophenone is added (4.3 g). The mixture is stirred for one more hour at the same temperature and slowly warmed to room temperature. After removal of the solvents, the residue is dissolved in dichloromethane (200 ml). The solution is washed with a 10% aqueous solution of ammonium chloride (3×100 ml) and with water (2×100 ml), dried over magnesium sulphate and evaporated in vacuo. The oily residue is purified by column chromatography on silica gel using hexane/toluene 1:1 as eluant. The product is dried in vacuo to constant weight to yield 1-(1,3-dithiolan-2-ylidene)-1-(4-fluorophenyl)-ethane, m.p. 27°-31°.

EXAMPLE 5

A solution of 2-diethoxyphosphoryl-1,3-dithiane (23.4 g) and 3,4-dimethoxybenzaldehyde (16.0 g) in dichloromethane (70 ml) is added to a mixture of dichloromethane (85 ml), a 50% aqueous solution of sodium hydroxide (170 ml) and triethylbenzylammonium chloride (1.4 g). The mixture is stirred for 24 hours at room temperature. The two phases are then separated. The aqueous solution is extracted with dichloromethane (100 ml) and the combined organic solutions are washed with a 10% aqueous solution of ammonium chloride (3×100 ml) and with water (2×100 ml). The dichloromethane is dried over magnesium sulphate and evaporated in vacuo. The residue is purified by column chromatography on silica gel using chloroform as eluant. The product is dried in vacuo to constant weight to yield (1,3-dithiolan-2-ylidene)-(3,4-dimethoxyphenyl)methane, m.p. 74°—75°.

EXAMPLE 6

Sodium hydride (6.5 g, 55 % dispersion in mineral oil) is washed with hexane (3×15 ml). A solution of 2-(3-trifluoromethylphenyl)-1-(4-methoxyphenyl)-ethanone (20.0 g) in dry dimethyl sulphoxide (20 ml) is than added. The mixture is stirred for two hours at room temperature and a mixture of 1,2-dibromoethane (19.2 g) and ether (40 ml) is slowly added. The mixture is stirred for 1½ hours at room temperature. Water (100 ml) is then added and the phases are separated. The aqueous phase is extracted with ether (3×150 ml) and the combined organic solutions are washed with water (5×200 ml) and dried over magnesium sulphate. After evaporation of the solvent in vacuo, the residue is recrystallised from isopropanol. The product is dried in vacuo to constant weight to yield 2-(1,3-dithiolan-2-ylidene)-2-(3-trifluoromethylphenyl)-1-(4-methoxyphenyl-ethanone, m.p. 138°-139°.

The starting material may be prepared as follows:

Anisole (32.4 g) and aluminium trichloride (36.0 g) are added to 1,2-dichloroethane (240 ml). The mixture is cooled to −5° and (3-trifluoromethylphenyl)-acetyl chloride (66.8 g) is slowly added. The mixture is stirred for 1½ hours and poured into a mixture of crushed ice (400 g) and water (150 ml). After heating to room temperature, the compound is extracted with ether (3×200 ml). The combined organic phases are washed with a 2% aqueous solution of sodium hydroxide (200 ml and with water (3×200 ml), dried over magnesium sulphate and the solvents are removed invacuo. The residue is recrystallised from hexane. The product is dried in vacuo to constant weight to yield 2-(3-trifluoromethylphenyl)-1-(4-methoxyphenyl)ethanone, m.p. 94°-95°.

EXAMPLES 7

Dry dimethyl sulphoxide (180 ml) is added to sodium hydride (9.0 g, 55% dispersioninmacraloil). After 30 minutes, isopropyl 4-fluorophenylacetate (17.7 g) and carbon disulphide (8.2 g) are added. The mixture is stirred for two hours at room temperature. 1,2-Dibromoethane (18.6 g) is then slowly added. The reaction is exothermic and the temperature is maintained below 30°. The mixture is stirred for one hour, and then ether (200 ml) is added. After cooling to 0° water (200 ml) is slowly added. The two phases are separated. The aqueous phase is extracted with ether (2×100 ml) and the combined organic solutions are washed with water (2×50 ml). After drying over magnesium sulphate, the solvent is evaporated in vacuo and the residue is recrystallised from hexane. The product is dried in vacuo to constant weight to yield isopropyl (1,3-dithiolan-2-ylidene)-(4-fluorophenyl)-acetate, m.p. 106°-107°.

The starting material may be prepared as follows:

A mixture of 4-fluorophenylacetic acid (123.0 g), 2-propanol (96.0 g), p-toluenesulphonic acid (9.6 g) and benzene (1.3 g) is refluxed for 7 hours with a Dean-Stark separator. The solution is washed with a 10% aqueous solution of sodium carbonate (2×500 ml) and with water (2×500 ml). After drying over magnesium sulphate, the solvent and the excess 2-propanol are evaporated in vacuo. The residue is distilled (51°-53°/3.10$^{-2}$ Torr) to yield isopropyl 4-fluorophenylacetate.

EXAMPLE 8

To a solution of isopropyl 4-fluorophenylacetate (98.1 g) in dimethylsulphoxide (1.2 g) there are added carbon disulphide (38.0 g) and then, slowly, a solution of potassium hydroxide (84.9 g) in water (150 ml). The mixture is stirred for 2 hours at 40° and cooled to room temperature. cis-1,2-Dichloroethylene (50 g) is added very slowly and the mixture is stirred at 45° for 2 hours. Water (1.5 l) and hexane (1 l) are added, the two phases are separated and the aqueous solution is extracted with hexane (3×1 l). The combined organic phases are washed with water (2×1 l), dried over magnesium sulphate and evaporated. The residue is crystallised from hexane. The product is dried in vacuo to constant weight to yield isopropyl (1,3-dithiol-2-ylidene)-(4-fluorophenyl)-acetate, m.p. 86°.

EXAMPLE 9

The same compound may be prepared in the following manner:

Sodium hydride (2.2 g, 55 % dispersion in mineral oil) is added to a solution of isopropyl 4-fluorophenylacetate (3.9 g) in dry tetrahydrofuran (50 ml). The mixture is stirred for two hours at room temperature. 2-Methylthio-1,3-dithiolium perchlorate (5.5 g) is then added and the mixture is heated under reflux for seven hours. After cooling to room temperature, water (300 ml) is slowly added. The solution is extracted with ether (3×200 ml). The combined organic solutions are washed with water (100 ml), dried over magnesium sulphate and the solvents are evaporated in vacuo. The residue is purified by column chromatography on silica gel using hexane/toluene 1:9 as eluant. The product is recrystallized from ligroin and dried -in vacuo to constant weight to yield isopropyl (1,3-dithiol-2-ylidene)-(4-fluorophenyl)-acetate, m.p. 86° (as Example 8).

EXAMPLE 10

As Example 7, but using n-octyl 3-trifluoromethylphenylacetate (28.5 g) instead of isopropyl 4-fluorophenylacetate. n-Octyl (1,3-dithiolan-2-ylidene)-(3-trifluoromethylphenyl)-acetate is obtained, m.p. 42°–43°.

The starting material may be prepared as follows:

A mixture of 3-trifluoromethylphenylacetic acid (150.0 g), n-octanol (130.0 g), p-toluenesulphonic acid (9.5 g) and benzene (800 ml) is refluxed for 7 hours with a Dean-Stark separator. The solution is washed with a 10% aqueous solution of sodium carbonate (3×500 ml) and with water (3×500 ml). After drying over magnesium sulphate, the solvent is evaporated in vacuo. The residue is distilled (95°–97°/2.10$^{-2}$ Torr) to yield n-octyl 3-trifluoromethylphenylacetate.

EXAMPLE 11

As Example 7, but using 1,3-dichloropropane (14.8 g) instead of 1,2-dibromoethane, and n-octyl 3-trifluoromethylphenylacetate (28.5 g) instead of isopropyl 4-fluorophenylacetate. n-Octyl (1,3-dithian-2-ylidene)-(3-trifluoromethylphenyl)-acetate is obtained, m.p. 49°.

EXAMPLE 12

The same compound may be prepared in the following manner:

To a solution of n-octyl 3-trifluoromethylphenylacetate (112.2 g) in dimethyl sulphoxide (850 ml) there are added carbon disulphide (30.4 g) and, slowly, a solution of potassium hydroxide (60.0 g) in water (100 ml). The mixture is stirred for 2 hours at 40°. 1,3-dichloropropane (40.1 g) is then added and the mixture is stirred at 50° for 3 hours. Water (800 ml) and hexane (800 ml) are added, the two phases are separated and the aqueous solution is extracted with hexane (2×500 ml). The combined organic phases are washed with water (400 ml), dried over magnesium sulphate and evaporated. The residue is crystallized from pentane. The product is dried in vacuo to constant weight to yield n-octyl (1,3-dithian-2-ylidene)-(3-trifluoromethylphenyl)-acetate, m.p. 49° (as Example 11).

EXAMPLE 13

As Example 7, but using 1,3-dichloroacetone (17.1 g) instead of 1,2-dibromoethane, and n-octyl 3-trifluoromethylphenylacetate (28.5 g) instead of isopropyl 4-fluorophenylacetate. The crude product is purified by column chromatography on silica gel using hexane/ethyl acetate 80:20 as eluant. n-Octyl (5-oxo-1,3-dithian-2-ylidene)-(3-trifluoromethylphenyl)-acetate is obtained as a liquid, b.p. 220°–225°/1.5.10$^{-2}$ torr.

EXAMPLE 14

As Example 7 but using 1,4-dibromobutane (29.2 g) instead of 1,2-dibromoethane, and n-octyl 3-trifluoromethylphenylacetate (28,5 g) instead of isopropyl 4-fluorophenylacetate. The crude product is purified by column chromatography on silicagel using hexane/toluene (3:7) as eluant. n-Octyl (3-trifluoromethylphenyl)-(1,3-dithiepan-2-ylidene)-acetate is obtained as a liquid, b.p. 241°–243°/2.5.10$^{-2}$ torr.

EXAMPLE 15

As Example 1 but using 3-acetylpyridine (10.2 g) instead of 4-dimethylaminobenzophenone. The reaction mixture is poured into water (1000 ml) and extracted with ethyl acetate (3×200 ml). The combined organic solutions are washed with water (100 ml) and dried over magnesium sulphate. The solvents are evaporated in vacuo and the residue is purified by column chromatography on silicagel using dichloromethane/ethyl acetate (1:1) as eluant. The product is dried in vacuo to constant weight to give 1-(1,3-dithian-2-ylidene)-1-(3-pyridyl)-ethane, m.p. 34°–36°.

EXAMPLE 16

As Example 15 but using 2-phenyl-1-(2-pyridyl)-ethanone (16.6 g) instead of 3-acetylpyridine. After recrystallisation from 2-propanol and drying in vacuo to constant weight 1-(1,3-dithian-2-ylidene)-2-phenyl-1-(2-pyridyl)-ethane is obtained, m.p. 96.5°–97.5°.

EXAMPLE 17

As Example 15 but using 2-dimethylamino-1-phenylethanol (13.7 g) instead of 3-acetylpyridine. The crude material is pyrified by column chromatography on aluminium oxide using dichloromethane as eluant. The product is dried in vacuo to constant weight to give 1-(1,3-dithian-2-ylidene)-2-dimethylamino-1-phenylethane as an oil at room temperature.

The product is dissolved in ethanol (150 ml) and fumaric acid (7.9 g) is added. The mixture is stirred and the solvent is evaporated in vacuo. Water (200 ml) is added to the residue, the slightly turbid solution is filtered and water is removed by freeze-drying. 1-(1,3-dithian-2-ylidene)-2-dimethylamino-1-phenyl-ethane fumarate is obtained, m.p. 136°–139°.

EXAMPLE 18

To a solution of 2-trimethylsilyl-1,3-dithiane (29.1 g) in dry tetrahydrofuran (600 ml) is added at −65° a 1.4M solution of n-butyllithium in hexane (108 ml). The reaction mixture is progressively warmed to 0° during 4 hours and cooled to −65°. A further 1.4M solution of n-butyllithium in hexane (108 ml) and a solution of 4-hydroxybenzophenone (30.0 g) in dry tetrahydrofuran (180 ml) are added, the temperature being maintained under −60°. The reaction mixture is progressively warmed to room temperature overnight. The suspension is slowly poured into water (2 l) and acidified to pH 2 with hydrochloric acid (32%). The compound is immediately extracted with ethyl acetste (4×500 ml). The combined organic solutions are washed with water (3×250 ml) and dried over magnesium sulphate. The solvent is evaporated in vacuo. The residue is washed with hexane (3×50 ml) and then recrystallized from carbon tetrachloride. The product is dried in vacuo to constant weight to give (1,3-dithian-2-ylidene)-(4-hydroxyphenyl)-phenylmethane, m.p. 135°–137°.

EXAMPLE 19

As Example 18 but using 4-benzoylbenzoic acid (34.2 g) instead of 4-hydroxybenzophenone. The crude material is purified by recrystallisation from a mixture of 2-propanol and acetone. The product is dried in vacuo to constant weight to give (4-carboxyphenyl)-(1,3-dithian-2-ylidene)-phenylmethane, m.p. 261°–262°.

The product (10.0 g) is dissolved in ethanol (1 l) and sodium hydroxide (1.2 g) is added. The mixture is stirred for 15 minutes at 50° up to solubilisation and the solvent is evaporated in vacuo. The residue is recrystallized from water. The compound is dried in vacuo to constant weight to give the sodium salt of (4-carboxyphenyl)-(1,3-dithian-2-ylidene)-phenylmethane, m.p. >300°.

EXAMPLE 20

Dry dimethylsulphoxide (130 ml) is added to sodium hydride (9.6 g, 55% dispersion in mineral oil). After 30 minutes, a solution of N,N-dimethyl-benzylsulphonamide (20.0 g) in dry dimethylsulphoxide (70 ml) and carbon disulphide (7.6 g) are added. The mixture is stirred for 30 minutes and 1,3-dichloropropane (12.3 g) is slowly added. The mixture is stirred for 4 hours at room temperature. After cooling to 0° water (300 ml) is slowly added and extracted with ethyl acetate (5×400 ml). The combined organic solutions are washed with water (2×300 ml), dried over magnesium sulfate and concentrated to 800 ml. After 1 day, the precipitate is filtered and dried in vacuo constant weight to give (1,3-dithian-2-ylidene)-(N,N-dimethylsulfonamido)-phenylmethane, m.p. 159°–160°.

EXAMPLE 21

As Example 18 but using 3-hydroxyacetophenone (20.6 g) instead of 4-hydroxybenzophenone. The crude material is purified by column chromatography on silicagel using dichloromethane as eluant. The product is dried in vacuo to constant weight to give 1-(1,3-dithian-2-ylidene)-1-(3-hydroxyphenyl)-ethane, m.p. 63°–64°.

EXAMPLE 22

To a solution of sodium hydroxide (1.3 g) in water (30 ml), (1,3-dithian-2-ylidene)-(4-hydroxyplenyl)-phenylmethane (3.0 g) and chloroacetic acid (1.4 g) are added. The mixture is refluxed for 3 hours. The water is slowly acidified with concentrated hydrochloric acid to pH 3. The aqueous phase is extracted with water (3×20 ml). The combined organic phases are washed with water (2×10 ml) and dried over magnesium sulphate. The solvent is evaporated in vacuo. The residue is purified by column chromatography on silicagel using dichloromethane/formic acid (99:1) as eluant. The fractions containing the pure product are washed with water to neutrality, dried over magnesium sulphateand evaporated. The residue is dried in vacuo to constant weight to give (4-carboxymethoxyphenyl)-(1,3-dithian-2-ylidene)-phenylmethane, m.p. 176°–177°.

EXAMPLE 23

As Example 2 but using 1-(1,3-dithian-2-ylidene)-1-(3-hydroxyphenyl)-ethane (2.4 g) instead of (1,3-dithian-2-ylidene)-(4-hydroxyphenyl)-phenylmethane. The combined ethyl acetate solutions are extracted with saturated solutions of sodium hydrogenocarbonate (4×60 ml). The combined water solutions are acidified with concentrated hydrochloric acid and extracted with dichloromethane (3×200 ml). The combined organic phases are dried over magnesium sulphate and the solvent is evaporated in vacuo. The residue is recrystallized from dichloroethylene. The product is dried in vacuo to constant weight to give 1-(3-carboxymethoxyphenyl)-1-(1,3-dithian-2-ylidene)-ethane, m.p. 133°–134°.

The product (1.0 g) is dissolved in ethanol (40 ml) and a 0,1N solution of sodium hydroxide (33.8 ml) is added. The solvents are evaporated in vacuo and the sodium salt of 1-(3-carboxymethoxyphenyl)-1-(1,3-dithian-2-ylidene)-ethane is obtained, m.p. >300°.

EXAMPLE 24

As Example 1 but using 2-acetylthiophen (10.6 g) instead of 4-dimethylaminobenzophenone. The crude material is purified by column chromatography on silicagel using hexane/dichloromethane (8:2) as eluant. 1-(1,3-dithian-2-ylidene)-1-(2-thienyl)-ethane is obtained as a liquid, b.p. 200°–205°/0.2 torr.

EXAMPLE 25

(1,3-Dithian-2-ylidene)-bis-(4-fluorophenyl)-methane (960 mg) and sodium metaperiodate are dissolved in dioxan (60 ml) and water (6 ml). The mixture is stirred at room temperature for 24 hours and then filtered. The solvents of the filtrate are removed in vacuo and the residue is purified by column chromatography on silicagel using ethyl acetate/dichloromethane (1:1) as eluant. The product is dried in vacuo to constant weight to give (1,3-dithian-1-oxide-2-ylidene)-bis-(4-fluorophenyl)-methane, m.p. 176°–177°.

EXAMPLE 26

As example 1 but using 4-(4-methylpiperazino)-acetophenone (18.3 g) instead of 4-dimethylamino-benzophenone. The crude material is recrystallized from hexane and ethyl acetate. The product is dried in vacuo to constant weight to yield 1-(1,3-dithian-2-ylidene)-1-[4-(4-methyl-piperazino)-phenyl]-ethane, m.p. 91°–92°.

The fumarate is prepared as in example 17, m.p. 185°–186°.

EXAMPLE 27

To a solution of n-octyl (1,3-dithian-2-ylidene)-(3-trifluoromethylphenyl)-acetate (15 g) in ethanol (375 ml), a 30% solution of potassium hydroxide in water (375 ml) is added. The mixture is refluxed for 2 hours. The solvents are removed in vacuo. Water (500 ml) and ether (500 ml) are added. The water solution is acidified to pH 4 with 5N sulphuric acid. The phases are separated and the water solution is extracted with ether (3×350 ml). The combined organic solutions are dried over magnesium sulphate and the solvent is evaporated in vacuo. The residue is triturated in petrol ether (b.p. 40°–65°) and dried in vacuo to constant weight to give (1,3-dithian-2-ylidene)-(3-trifluoromethylphenyl)-acetic acid, m.p. 165°–166° C.

The sodium salt is prepared as in example 23, m.p. >300°.

EXAMPLE 28

Sodium (0.37 g) is added to dry methanol (5 ml). When the sodium has reacted, 1-(1,3-dithian-2-ylidene)-1-(3-hydroxyphenyl)-ethane (3.83 g) dissolved in dry toluene (20 ml) is added. The mixture is stirred for 1½ hours and the methanol is distilled. 1-Chloro-2-dimethylaminoethane (3.44 g) dissolved in dry toluene (10 ml) is then added. The mixture is stirred at 100° for 1½ hours and cooled to room temperature. Water (150 ml) is added, the two phases are separated and the aqueous solution is extracted with ethyl acetate (3×50 ml). The combined organic solutions are washed with water (50 ml) and dried over magnesium sulphate. The solvent is evaporated in vacuo and the residue is dried in vacuo to constant weight to give 1-(1,3-dithian-2-ylidene)-1-[3-(2-dimethylaminoethoxy)-phenyl]-ethane as a liquid.

The fumarate is prepared as in example 17, m.p. 134,5°–135,5°.

EXAMPLE 29

As example 18, but using 3-carboxy-4-methoxyacetophenone (29.2 g) instead of 4-hydroxybenzophenone. The crude material is dissolved in diethylether (500 ml) and extracted with a 2-N aqueous solution of sodium hydrogen carbonate (2×300 ml). The solvent of the organic phase is evaporated in vacuo. The residue is dried in vacuo to give 1-(1,3-dithian-2-ylidene)-1-(4-methoxy-3-valerylphenyl)-ethane as a liquid, b.p. 250°–255°/0.5 Torr.

The combined aqueous phases of the extraction are acidified to pH 2 with hydrochloric acid (32%) and extracted with diethylether (3×500 ml). The combined organic phases are washed with water (2×100 ml) and dried over magnesium sulphate and the solvent is removed in vacuo. The residue is purified on column chromatography on silica gel using ethyl acetate/chloroform/formic acid 5:5:1 as eluant. The product is dried in vacuo to constant weight to give 1-(3-carboxy-4-methoxyphenyl)-1-(1,3-dithian-2-ylidene)-ethane, m.p. 130°–132°.

1-(3-Carboxy-4-methoxyphenyl)-1-(1,3-dithian-2-ylidene)-ethane (10.0 g) is dissolved in ethanol (200 ml) and a solution of sodium hydroxyde (1.3 g) in water (10 ml) is added. The solvents are evaporated in vacuo and ethanol (50 ml) is added. The suspension is stirred and the solid is filtered and dried in vacuo to constant weight. The sodium salt of 1-(3-carboxy-4-methoxyphenyl)-1-(1,3-dithian-2-ylidene)-ethane is obtained, m.p. >300°.

EXAMPLE 30

As in example 15, but using 1-(2,5-dimethoxyphenyl)-2-dimethylamino-ethanone (19.0 g) instead of 3-acetylpyridine. The crude material is purified by column chromatography on aluminium oxide using n-hexane/ethylacetate 9:1 as eluant. The product is dried in vacuo to constant weight to give 1-(1,3-dithian-2-ylidene)-1-(2,5-dimethoxyphenyl)-2-dimethylaminoethane as a light yellow liquid.

The product is dissolved in ethanol (500 ml) and oxalic acid (6.2 g) is added. The mixture is stirred and the solvent is evaporated in vacuo. The residue is added to acetone (400 ml). The mixture is stirred for 15 minutes. The solid is filtered and dried in vacuo to constant weight to give 1-(1,3-dithian-2-ylidene)-1-(2,5-dimethoxyphenyl)-2-dimethylamino-ethane oxalate, m.p. 153,5°–156,5°.

The starting material may be prepared as follows:

2-bromo-1-(2,5-dimethoxyphenyl)-ethanone (10.0 g) is added dropwise to a solution of dimethylamine (6.1 g) in toluene (450 ml). The mixture is stirred overnight at room temperature and extracted with a 1-N water solution of hydrochloric acid (3×250 ml). The mixed aqueous phases are alcalinized with a 25% water solution of sodium hydroxide (200 ml) and extracted with dichloromethane (4×250 ml). The mixed organic phases are washed with water (3×200 ml) and dried over magnesium sulphate. The solvent is distilled in vacuo and the residue is dried in vacuo to constant weight to give 1-(2,5-dimethoxyphenyl)-2-dimethylamino-ethanone which is a liquid, b.p. 250°–255°.

EXAMPLE 31

As example 15, but using 3-dimethylamino-1-phenyl-1-propanone (15.7 g) instead of 3-acetylpyridine. The crude material is purified by column chromatography on aluminium oxide using h-hexane/ethylacetate 9:1 as eluant. The product is dried in vacuo to constant weight to give 1-(1,3-dithian-2-ylidene)-3-dimethylamino-1-phenylpropane, m.p. 136°–138°.

The fumarate is prepared as in example 17, m.p. 144°–147°.

EXAMPLE 32

As example 15, but using 1-(4-fluorophenyl)-2-dimethylamino-ethanone (15.4 g) instead of 3-acetylpyridine. The crude material is purified by column chromatography on aluminium oxide using hexane/ethyl acetate 95:5 as eluant. The product is dried in vacuo to constant weight to give 1-(1,3-dithian-2-ylidene)-1-(4-fluorophenyl)-2-dimethylamino-ethane as an oil.

The fumarate is prepared as in example 17 and is recrystallized from n-propanol, m.p. 171°–172°.

EXAMPLE 33

As example 15, but using 1-(4-fluorophenyl)-2-morpholino-ethanone (19.0 g) instead of 3-acetylpyridine. The crude material is purified by recrystallisation from a mixture of hexane and ethyl acetate. The product is dried in vacuo to constant weight to give 1-(1,3-dithian-2-ylidene)-1-(4-fluorophenyl)-2-morpholino-ethane, m.p. 104,5°–106°.

Gaseous hydrochloric acid is bubbled for 30 minutes through a solution of 1-(1,3-dithian-2-ylidene)-1-(4-fluorophenyl)-2-morpholino-ethane (5.0 g) in diethylether (600 ml). After cooling to −20° for 2 hours, the precipitate is filtered and dried in vacuo to give 1-(1,3-dithian-2-ylidene)-1-(4-fluorophenyl)-2-morpholino-ethane hydrochloride, m.p. 193°–194°.

The starting material may be prepared as follow:

A solution of morpholine (16.0 g) in toluene (100 ml) is slowly added to a solution of 2-bromo-1-(4-fluorophenyl)-ethanone (20.0 g) in toluene (250 ml). The mixture is stirred overnight at room temperature and extracted with a 1-N aqueous solution of hydrochlorid acid (3×250 ml). The mixed aqueous phases are alcalinized with a 50% aqueous solution of sodium hydroxide (55 ml) and extracted with ethyl acetate (3×250 ml). The mixed organic phases are washed with water (3×100 ml) and dried over magnesium sulphate. The solvent is distilled in vacuo and the residue is dried in vacuo to constant weight to give 1-(4-fluorophenyl)-2-morpholino-ethanone which is a liquid.

EXAMPLE 34

As example 15, but using 3-aminoacetophenone (11.5 g) instead of 3-acetylpyridine. The crude material contains as a major impurity the starting 3-aminoacetophenone which is removed by crystallisation from carbontetrachloride. The mother liquor of crystallisation is evaporated in vacuo and the residue is purified by column chromatograph on aluminium oxide using hexane/ethyl acetate 8:2 as eluant. The product is dried in vacuo to constant weight to give 1-(3-aminophenyl)-1-(1,3-dithian-2-ylidene)-ethane, m.p. 99°–100°.

The hydrochloride is prepared as in example 33, m.p. 182°–185°.

EXAMPLE 35

Succinic anhydride (0.63 g) is added to a solution of 1-(3-aminophenyl)-1-(1,3-dithian-2-ylidene)-ethane (1.00 g) in dry toluene. The mixture is heated at 60° for 20 minutes with stirring. The precipitate is filtered, washed with toluene and dried in vacuo at 40° to constant weight. 1-(1,3-dithian-2-ylidene)-1(3-hemisuccinamidophenyl)ethane is obtained, m.p, 146°–148°.

The sodium salt is prepared as in example 23, m.p. >300°.

EXAMPLE 36

As example 15, but using 1-(4-fluorophenyl)-2-(1-pyrrolidinyl)-ethanone (17.6 g) instead of 3-acetypyridine. The crude material is purified by column chromatography on aluminium oxide using hexane/ethyl acetate 9:1 as eluant. The product is triturated in hexane, filtered and dried in vacuo to constant weight to give 1-(1,3-dithian-2-ylidene)-1-(4-fluorophenyl)-2-(1-pyrrolidinyl)-ethane, m.p. 69°–70°.

The hydrochloride is prepared as in example 33, m.p. 164°–165°.

The starting material may be prepared as follows:

A solution of 2-bromo-1-(4-fluorophenyl)-ethanone (32.5 g) and pyrrolidine (21.4 g) in dry diethylether (600 ml) is stirred at room temperature of 4 hours. The precipitate is filtered off and gaseous hydrochloric acid is bubbled for 30 minutes through the solution. 300 ml of ether is removed by distillation and the precipitate is filtered. It is recrystallized from a mixture of ethanol and diethylether and dried in vacuo to constant weight to give 1-(4-fluorophenyl)-2-(1-pyrrolidinyl)-ethanone hydrochloride, m.p. 204°–205°.

By the usual way 1-(4-fluorophenyl)-2-(1-pyrrolidinyl)-ethanone is obtained as a solid, m.p. 49°–50°.

EXAMPLE 37

As example 15, but using 1-(4-fluorophenyl)-2-(isopropylmethylamino)-ethanone (17.8 g) instead of 3-acetylpyridine. The crude material is purified by column chromatography on aluminium oxide using hexane/ethyl acetate 9:1 as eluant. After drying in vacuo to constant weight 1-(1,3-dithian-2-ylidane)-1-(4-fluorophenyl)-2-(isopropylmethylamino)-ethane is obtained as an oil.

The hydrochloride is prepared as in example 33, m.p. 159°–161°.

The starting material may be prepared as follows:

A solution of 2-bromo-1-(4-fluorophenyl)-ethanone (32.5 g) and isopropylmethylamine (21.9 g) in dry diethylether (600 ml) is stirred at room temperature for 20 hours. The precipitate is filtered off and gaseous hydrochloric acid is bubbled for 30 minutes through the solution. 300 ml of ether is removed by distillation and the precipitate is filtered. It is recrystallized from a mixture of ethanol and diethylether and dried in vacuo to constant weight to give 1-(4-fluorophenyl)-2-(isopropylmethylamino)-ethanone hydrochloride, m.p. 188°–190°.

By the usual way 1-(4-fluorophenyl)-2-(isopropylmethylamino)-ethanone is obtained as an oil.

EXAMPLE 38

Pharmaceutical preparations:

(a) Tablets ingredients for 100 000 tablets:

| (1) active substance, e.g. 2-(1,3-dithiolan-2-ylidene)-2-(3-trifluoromethylphenyl)-1-(4-methoxyphenyl)-ethane | 50.0 kg |
|---|---|
| (2) carboxymethyl starch | 2.0 kg |
| (3) silicon dioxide (Aerosil ®-200) | 0.5 kg |
| (4) magnesium stearate | 0.25 kg |
| (5) microcrystalline cellulose (Avicel ®-102) | 5.0 kg |
| | 57.75 kg |

The active substance is calibrated through a trellis of 1 mm mounted on an oscillating calibrator.

In a drum mixer the active substance is mixed during 20 minutes with carboxymethyl starch (2), silicon dioxide (3) and the microcrystalline cellulose (5); then the magnesium stearate (4) is added and the mixing process continued for 5 more minutes. The mixture is used for the preparation of round biconvex tablets with a weight of 577.8 mg/tablet and a diameter of 10.5 mm. The hardness of these tablets is between 130–180N (Heberlein) and the desintegration in the artificial gastric juice (pH 1.2; Pharmacopée Helv. VI) is below 15 minutes. A rotating tabletting machine is used for making these tablets.

(b) Tablets: ingredients for 100 000 tablets:

| (1) active substance, e.g. 2-(1,3-dithiolan-2-ylidene)-2-(3-trifluoromethylphenyl)-1-(4-methoxyphenyl-ethane | 50.0 kg |
|---|---|
| (2) carboxymethyl starch | 1.0 kg |
| (3) distilled water | (21.0) kg |
| (4) silicon dioxide (Aerosil ®-200) | 0.25 kg |
| (5) magnesium stearate | 0.25 kg |

The active substance is centrifuged and dried in the form of powder, mixed with carboxymethyl starch (2) in a planetary mixer during 20 minutes, humidified with distilled water and kneaded during 20 minutes. The pasty mass obtained is granulated through a trellis of 3.0 mm, mounted on an oscillating granulator, and dried in a bed of fluidising air of 70°. The granules obtained are calibrated through a trellis of 1.5 mm and mixed with silicon dioxide (4) and magnesium stearate (5) in a freefall-mixer. The mixture thus obtained is compressed with the help of a rotating tabletting machine into round tablets of 515 mg/tablet of a hardness of 120–150N (Heberlein). The desintegration rate in the artificial gastric juice (Pharm. Helv. VI) is below 15 minutes.

(c) Capsules: ingredients for 10 000 capsules:

| (1) active substance, e.g. 2-(1,3-dithiolan-2-ylidene)-2-(3-trifluoromethylphenyl)-1-(4-methoxyphenyl)-ethane | 5000 g |
|---|---|
| (2) stearic acid | 30 g |
| (3) magnesium stearate | 10 g |

The vermicellis of the active substance are calibrated through a trellis of 1 mm and mixed with the stearic acid (2) and magnesium stearate (3) during 20 minutes. The mixture is used for the preparation of the capsules of size 0 with 500 mg of active ingredient with the help of a suitable encapsulating apparatus. The desintegration of these capsules in artificial gastric juice (Pharm. Helv. VI) is below 15 minutes.

(d) Injectable preparation:

The active substance, e.g. 1-(1,3-dithian-2-ylidene)-2-dimethylamino-1-phenylethane furmarate (100 g) is dissolved in sterile pyrogen free water (10 l). Pyrogen free sodium chloride (50 g) is added. The solution is then filtered, under aseptic conditions, through a sterile membrane (Millipore OA 03-GS, 0.22 µm) and filled still under aseptic conditions into ampoules. The ampoules are sealed and checked for particulate contamination, sterility, pyrogens, osmolality, pH and content of active substance respectively. By this technique, 1000 10 ml ampoules each containing 100 mg of the active substance.

Pharmacological Tests

The liver-protecting properties of the compounds according to the present invention were evaluated by means of the following experimental methods.

I. The galactosamine hepatitis model in the rat

It is known that galactosamine induces in the rat similar hepatic lesions to those produced in man by the hepatitis virus (D. Deppler et al., Experimental molecular pathology, 9, 279 (1968)). Therefore the galactosamine hepatitis model is widely used to evaluate hepatoprotective compounds.

Male rats (RA 25, CIBA-GEIGY breedings, Basle) with a body weight of 300 g were used. Eight rats were included per experimental group. Liver injury was produced by subcutaneous injection of a dose of 500 mg/kg of galactosamine hydrochloride. Compounds to be tested were administered by intraperitoneal route as a suspension in polyethyleneglycol 300, 50% in water. Control animals received the solvent alone. The compounds were administered at several dosage rates 24 hours before, and at the same time as, the galactosamine injection. The animals were fasted after the galactosamine injection and were sacrificed 24 hours later. Blood was taken for determination of the glutamate oxaloacetate transaminase (GOT) as a biochemical index of liver injury.

Galactosamine induces a very high increase of blood transaminase (GOT) which is correlated with liver necrosis. In animals treated by the test compound and galactosamine, the blood transaminase level is significantly reduced. The percentage modification of blood transaminase in animals treated with galactosamine and the compound as compared with animals treated with galactosamine alone is calculated. Each compound is characterised by the dosage (in µmoles/kg) which results in a 50% decrease of blood transaminase of galactosamine-intoxicated rats.

II. Pentobarbital sleeping time in mice intoxicated with carbon tetrachloride The duration of pentobarbital sleeping time reflects the metabolic activity of the liver. Therefore, this test can be used to estimate the extent of liver injury and also the efficacy of a hepatoprotective compound (J. A. Castro et al., Toxicology and applied Pharmacology, 41,305 (1977)).

Male mice (MA 01, Ciba-Geigy breeding, Basle) with a body weight of about 25 g were used for this test. Compounds were administered by i.p. route as a solution in 10% propyleneglycol. Control animals received the solvent alone. Ten mice were included per group. After 30 minutes, liver injury was produced by i.p. administration of $CCl_4$ (0.17 ml/kg) as a solution in liquid paraffin. Animals were fasted after the injection of $CCl_4$. 24 hours later, pentobarbital sodium salt (20 mg/kg) was administered i.p. and the duration of sleeping time was recorded.

The mean value of the duration of sleeping time in each group ($CCl_4$-treated animals and animals treated with $CCl_4$ and test compound) is calculated. In liver-protected mice the duration of sleeping time is reduced as compared with the duration of sleeping time in $CCl_4$-treated mice. Results are expressed by the percentage modification of the duration of sleeping time in mice treated with $CCl_4$ and test compound as compared with the duration of sleeping time in mice treated with $CCl_4$ alone, for a given dosage rate.

The test results of a number of compounds according to the invention used in the galactosamine model and in the $CCl_4$ model are reported in Table 1.

TABLE 1

| compound | galactosamine model $DE_{50}$ µmole/kg | $CCl_4$ model % modification sleeping time |
| --- | --- | --- |
| (4-dimethylaminophenyl)-(1,3-dithian-2-ylidene)-phenylmethane | 10 | −40 (100 mg/kg) |
| (1,3-dithian-2-ylidene)-bis-(4-fluorophenyl)-methane | 5 | −19 (100 mg/kg) |
| 1-(1,3-dithian-2-ylidene)-2,2,2-trifluoro-1-phenyl-ethane | 23 | |
| 1-(1,3-dithiolan-2-ylidene)-1-(4-fluorophenyl)-ethane | 31 | −60 (100 mg/kg) |
| 1,3-dithiolan-2-ylidene)-(3,4-dimethoxyphenyl)-methane | 98 | −6 (100 mg/kg) |
| 2-(1,3-dithiolan-2-ylidene)-2-(3-trifluoromethylphenyl)-1-(4-methoxyphenyl)-ethanone | 26 | −57 (25 mg/kg) |
| isopropyl (1,3-dithiolan-2-ylidene)-(4-fluorophenyl)-acetate | 156 | −75 (100 mg/kg) |
| isopropyl (1,3-dithiol-2-ylidene)-(4-fluorophenyl)-acetate | 95 | −39 (100 mg/kg) |
| n-octyl (1,3-dithiolan-2-ylidene)-(3-trifluoromethylphenyl)-acetate | 72 | −46 (100 mg/kg) |
| n-octyl (1,3-dithian-2-ylidene)-(3-trifluoromethylphenyl)-acetate | 17 | −45 (100 mg/kg) |

TABLE 1-continued

| compound | galactosamine model DE$_{50}$ μmole/kg) | CCl$_4$ model % modification sleeping time |
|---|---|---|
| n-octyl-(3-trifluoromethylphenyl)-(5-oxo-1,3-dithian-2-ylidene)-acetate | 11 | |
| n-octyl (1,3-dithiepan-2-ylidene)-3-trifluoromethylphenyl)-acetate | 76 | −26 (100 mg/kg) |
| 1-(1,3-dithian-2-ylidene)-1-(3-pyridyl)-ethane | 500 | |
| 1-(1,3-dithian-2-ylidene)-2-phenyl-1-(2-pyridyl)-ethane | 137 | −34 (100 mg/kg) |
| 1-(1,3-dithian-2-ylidene)-2-dimethylamino-1-phenyl-ethane fumarate | 33 | |
| (1,3-dithian-2-ylidene)-N,N-dimethylsulphonamido-phenylmethane | 187 | |
| (4-carboxyphenyl)-(1,3-dithian-2-ylidene)-phenyl-methane, sodium salt | 286 | |
| 1-(1,3-dithian-2-ylidene)-1-(3-hydroxyphenyl)-ethane | 115 | — |
| 1-(3-carboxymethoxyphenyl)-1-(1,3-dithian-2-ylidene)-ethane sodium salt | 406 | — |
| (1,3-dithian-1-oxide-2-ylidene)-bis-(4-fluorophenyl)-methane | 77 | −100 (75 mg/kg) |
| 1-(1,3-dithian-2-ylidene)-1-[4-(4-methylpiperazino)-phenyl]-ethane fumarate | 95 | — |
| (1,3-dithian-2-ylidene)-(3-trifluoromethylphenyl)-acetic acid sodium salt | — | −17 (100 mg/kg) |
| 1-(1,3-dithian-2-ylidene)-1-[3-(2-dimethylaminoethoxy)-phenyl]-ethane fumarate | 269 | — |
| 1-(3-carboxy-4-methoxyphenyl)-1-(1,3-dithian-2-ylidene)-ethane sodium salt | — | — |
| 1-(1,3-dithian-2-ylidene)-1-(2,5-dimethoxyphenyl)-2-dimethylamino-ethane oxalate | 101 | — |
| 1-(1,3-dithian-2-ylidene)-3-dimethylamino-1-phenyl-propane fumarate | 122 | — |
| 1-(1,3-dithian-2-ylidene)-1-(4-fluorophenyl)-2-dimethylamino-ethane fumarate | 36 | — |
| 1-(1,3-dithian-2-ylidene)-1-(4-fluorophenyl)-2-morpholino-ethane hydrochloride | 205 | — |
| 1-(3-aminophenyl)-1-(1,3-dithian-2-ylidene)-ethane hydrochloride | 197 | −73 (10 mg/kg) |
| (1,3-dithian-2-ylidene)phenylacetonitrile* | 65 | — |

*Known compound: K. A. Jensen and L. Henriksen, Acta Chem. Scand. 22, 1107–1128 (1968).

What is claimed is:

1. A compound of the formula

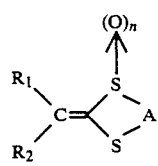

(Ic)

wherein (I)

R$_1$ is phenyl which is unsubstituted or substituted by a substituent selected from hydroxy, lower alkoxy, carboxy-lower alkoxy, HO$_3$S-lower alkoxy, di-lower alkylamino-lower alkoxy, halogen, lower alkanoyl, lower alkyl, halo-lower alkyl, carboxy, amino, di-lower alkylamino, lower alkanoylamino, and carboxy-lower alkanoylamino;

R$_2$ is (a) phenyl substituted by a substituent selected from carboxy-lower, alkoxy, halogen, halo-lower alkyl, carboxy, and di-lower alkylamino; or is (b) selected from the group consisting of lower alkyl, phenyl-lower alkyl, halo-lower alkyl, carboxy-lower alkyl, lower alkoxycarbonyl-lower alkylamino-lower alkyl, hycarbonyl-lower di-lower alkylamino-lower alkyl, hydroxybenzoyl, lower alkoxybenzoyl, carboxy, alkoxycarbonyl having up to 9 carbon atoms, and di-lower alkylamino-SO$_2$—;

A is 1,3-propylene which is unsubstituted or monosubstituted by oxo or hydroxy; and n is zero or 1;

(II)

R$_1$ is di-lower alkoxypheny;

R$_2$ is hydrogen; and

A and n are as defined above; or a pharmaceutically acceptable salt of such a compound having a salt-forming group.

2. The compound of claim 1 wherein (I)

R$_1$ is a phenyl substituted by halogen or halo-lower alkyl;

R$_2$ is phenyl substituted by halogen, or is lower alkyl, phenyl-lower alkoxybenzoyl, or alkoxycarbonyl having up to 9 carbon atoms;

A is 1,3-propylene; and n is zero; or (II)

R$_1$ is is di-lower alkoxyphenyl;

R$_2$ is hydrogen; and

A and n are as defined above; a pharmaceutically acceptable salt of such a compound having a salt-forming group.

3. A compound of claim 1 being (4-dimethylaminophenyl)-(1,3-dithian-2-ylidene)-phenylmethane.

4. A compound of claim 1 being (1,3-dithian-2-ylidene)-bis-(4-fluorophenyl)-methane.

5. A compound of claim 1 being (1,3-dithian-2-ylidene)-2,2,2-trifluoro-1-phenyl-ethane.

6. A compound of claim 1 being n-octyl (1,3-dithian-2-ylidene)-(3-trifluoromethylphenyl)-acetate.

7. A compound of claim 1 being n-octyl (5-oxo-1,3-dithian-2-ylidene)-(3-trifluoromethylphenyl)-acetate.

8. A compound of claim 1 being 1-(1,3-dithian-2-ylidene)-2-dimethylamino-1-phenylethane.

9. A compound of claim 1 being (4-carboxyphenyl)-(1,3-dithian-2-ylidene)-phenyl)phenylmethane.

10. A compound of claim 1 being (1,3-dithian-2-ylidene)-(N,N-dimethylsulfonamino)-phenylmethane.

11. A compound of claim 1 being 1-(1,3-dithian-2-ylidene)-1-(3-hydroxyphenyl)-ethane.

12. A compound of claim 1 being (4-carboxymethoxyphenyl)-(1,3-dithian-2-ylidene)-phenylmethane.

13. A compound of claim 1 being 1-(3 carboxymethoxyphenyl)1-(1,3-dithian-2-ylidene)-ethane.

14. A compound of claim 1 being 1-(1,3-dithian-1-oxide-2-ylidene)-bis-(4-fluorophenyl)-methane.

15. A compound of claim 1 being (1,3-dithian-2-ylidene)-(3-trifluoromethylphenyl)-acetate acid.

16. A compound of claim 1 being 1-(1,3-dithian-2-ylidene)-1-[3-(2-dimethylaminomethoxy)-phenyl]-ethane.

17. A compound of claim 1 being 1-(3-carboxy-4-methoxyphenyl)-1-(1,3-dithian-2-ylidene)-ethane.

18. A compound of claim 1 being 1-(1,3-dithain-2-ylidene)-1-(2,5-dimethoxyphenyl)-2-dimethylamino-ethane.

19. A compound of claim 1 being 1-(1,3-dithian-2-ylidene)-3-dimethylamino-1-phenylpropane.

20. A compound of claim 1 being 1-(1,3-dithian-2-ylidene)-1-(4-fluorophenyl)-2-dimethylamino-ethane.

21. A compound of claim 1 being 1-(3-aminophenyl)-1-(1,3-dithian-2-ylidene)-ethane.

22. A compound of claim 1 being 1-(1,3-dithian-2-ylidene)-1-(3-hemisuccinaminophenyl)-ethane.

23. A compound of claim 1 being 1-(1,3-dithian-2-ylidene)-1-(4-fluorophenyl)-2-(isopropylmethylamino)-ethane 24. A pharmaceutical composition for the treatment of hepatic fibrosis comprising a therapeutically effective amount of a compound of formula Ib, or a pharmaceutcially acceptable salt thereof, together with a pharmaceutically acceptable carrier; said formula Ib being

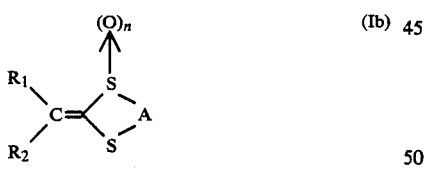

wherein
$R_1$ is phenyl which is unsubstituted or substituted by a substituent selected from hydroxy, lower alkoxy, carboxy-lower alkoxy, $HO_3S$-lower alkoxy di-lower alkylamino-lower alkoxy, halogen, lower alkanoyl, lower alkyl, halo-lower alkyl, carboxy, amino, di-lower-alkylamino, lower alkanoylamino, and carboxy-lower alkanoylamino; and
$R_2$ is
(a) phenyl which is unsubstituted or substituted by hydroxy, lower alkoxy, halogen, or di-lower alkylamino; or
(b) hydrogen, lower alkyl, halo-lower alkyl, carboxy-lower alkyl, alkoxycarbonyl-lower alkyl, di-lower alkylamino-lower alkyl, phenyl-lower alkyl, lower alkanoyl, hydroxy benzoyl, lower alkoxy benzoyl, alkoxycarbonyl having up to 9 carbon atoms, cyano, or di-lower alkylamino-$SO_2$—; and A is 1,3-propylene which is unsubstituted or monosubstituted by oxo or hydroxy; and n is zero or 1; with the proviso that $R_2$ is other than phenyl, hydroxyphenyl and lower alkoxyphenyl when $R_1$ is phenyl, hydroxyphenyl, lower alkoxyphenyl or di-lower alkylamino-lower alkoxy.

25. The composition of claim 24 wherein
$R_1$ is phenyl substituted by halogen, di-lower alkylamino, lower alkoxy, halo-lower alkyl; and
$R_2$ is
(a) hydrogen, lower alkyl; or
(b) phenyl which is unsubstituted or substituted by halogen; or
(c) lower alkoxy benzoyl, or lower alkoxycarbonyl having up to 9 carbon atoms; and
A is 1,3-propylene; and
n is zero.

26. A method of bearing hepatic fibrosis in a mammal comprising administering to a mammal in need of such treatment a therapeutically effective amount of a compound formula formula ia or of a pharmaceutically acceptable salt thereof wherein said formula Ia is

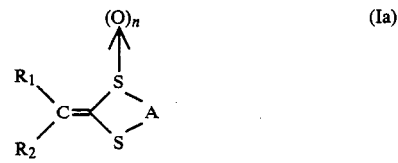

wherein
$R_1$ is phenyl which is unsubstituted or substituted by hydroxy, lower-alkoxy, carboxy-lower alkoxy, $HO_3S$-lower alkoxy, di-lower alkylamino-lower-alkoxy, halogen, lower alkanoyl, lower alkyl, halo-lower alkyl, carboxy, amino, di-lower alkylamino, lower alkanoylamino, or carboxy-lower-alkanoylamino;
$R_2$ is
(a) hydrogen;
(b) phenyl which is unsubstituted or substituted by hydroxy, lower alkoxy, halogen, halo-lower alkyl, or di-lower alkylamino; or
(c) lower alkyl, halo-lower alkyl, carboxy-lower alkyl, lower alkoxycarbonyl-lower alkyl, di-lower alkylamino-lower alkyl, phenyl lower alkanoyl, hydroxy benzoyl, lower alkoxy benzoyl, carboxy, alkoxycarbonyl having up to 9 carbon atoms, cyano, or di-lower alkylamino-$SO_2$—;
A is 1,3-propylene which is unsubstituted or monosubstituted by oxo or hydroxy; and
n is zero or 1.

27. The method of claim 26 wherein
$R_1$ is phenyl substituted by halogen, di-lower alkylamino, lower alkoxy, or halo-lower alkyl;
$R_2$ is
(a) hydrogen;
(b) phenyl which is unsubstituted or substituted by halogen; or
(c) lower alkyl, lower alkoxy benzoyl, or alkoxycarbonyl having up to 9 carbon atoms;
A is 1,3-propylene; and
n is zero.

28. The method of claim 26 wherein the compound of formula Ia is (1,3-dithian-2-ylidene)-(4-hydroxyphenyl)-phenylmethane.

* * * * *

UNITED STATES PATENT AND TRADEMARK OFFICE
CERTIFICATE OF CORRECTION

PATENT NO. : 4,946,861
DATED     : Aug. 7, 1990
INVENTOR(S) : Weith et al.

It is certified that error appears in the above-identified patent and that said Letters Patent is hereby corrected as shown below:

On the title page, inventors should read--

[75] Inventors: Andre J. Weith, Signy; Philippe M. Narbel, Prangins, both of Switzerland.--

Signed and Sealed this

Fourteenth Day of January, 1992

Attest:

HARRY F. MANBECK, JR.

*Attesting Officer*   Commissioner of Patents and Trademarks